(12) United States Patent
Blackwell et al.

(10) Patent No.: US 10,292,390 B2
(45) Date of Patent: May 21, 2019

(54) INHIBITION AND DISPERSION OF BACTERIAL BIOFILMS WITH 2-AMINOBENZIMIDAZOLE DERIVATIVES

(71) Applicant: WISCONSIN ALUMNI RESEARCH FOUNDATION, Madison, WI (US)

(72) Inventors: Helen Blackwell, Middleton, WI (US); Reto Frei, Ecublens (CH); Anthony Breitbach, Madison, WI (US); David M. Lynn, Middleton, WI (US); Adam H. Broderick, Midland, MI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 885 days.

(21) Appl. No.: 13/669,368

(22) Filed: Nov. 5, 2012

(65) Prior Publication Data

US 2013/0136782 A1    May 30, 2013

Related U.S. Application Data

(60) Provisional application No. 61/555,646, filed on Nov. 4, 2011.

(51) Int. Cl.
| | | |
|---|---|---|
| A01N 43/52 | (2006.01) | |
| C07D 235/30 | (2006.01) | |
| A61K 31/416 | (2006.01) | |
| A61K 45/00 | (2006.01) | |
| C07D 235/02 | (2006.01) | |
| A61K 31/4184 | (2006.01) | |

(52) U.S. Cl.
CPC ............ *A01N 43/52* (2013.01); *A61K 31/416* (2013.01); *A61K 31/4184* (2013.01); *A61K 45/00* (2013.01); *C07D 235/02* (2013.01); *C07D 235/30* (2013.01)

(58) Field of Classification Search
None
See application file for complete search history.

(56) References Cited

U.S. PATENT DOCUMENTS

| | | | |
|---|---|---|---|
| 4,434,288 | A | 2/1984 | Wikel |
| 5,248,672 | A | 9/1993 | Townsend |
| 5,665,709 | A | 9/1997 | Townsend |
| 5,705,490 | A | 1/1998 | Townsend |
| 5,712,255 | A | 1/1998 | Townsend |
| 6,251,689 | B1 | 6/2001 | Laborde |
| 6,380,180 | B1 | 4/2002 | Jensen et al. |
| 7,820,665 | B2 | 10/2010 | Otton |
| 7,883,720 | B2 | 2/2011 | Lynn et al. |
| 7,906,544 | B2 | 3/2011 | Melander et al. |
| 8,071,210 | B2 | 12/2011 | Lynn et al. |
| 2008/0181923 | A1 | 7/2008 | Melander et al. |
| 2008/0286345 | A1 | 11/2008 | Lynn et al. |
| 2008/0293796 | A1* | 11/2008 | Chow ............... A61K 9/0019 514/395 |
| 2009/0105375 | A1 | 4/2009 | Lynn et al. |
| 2011/0294668 | A1 | 12/2011 | Melander et al. |
| 2012/0171129 | A1 | 7/2012 | Melander et al. |

FOREIGN PATENT DOCUMENTS

| | | |
|---|---|---|
| CN | 1834090 | 9/2006 |
| WO | WO2004/047769 | 6/2004 |
| WO | WO2010/077603 | 7/2010 |
| WO | WO2010/144686 | 12/2010 |
| WO | WO2011099832 | 8/2011 |
| WO | WO2012006276 | 1/2012 |
| WO | WO2012030986 | 3/2012 |
| WO | WO2012/058531 | 5/2012 |

OTHER PUBLICATIONS

Podunavac et al (QSAR Analysis of 2-Amino or 2-Methyl-1-Substituted Benzimidazoles Against Pseudomonas aeruginosa. Int J Mol Sci. Apr. 2009; 10(4): 1670-1682).*
Rogers et al (A 2-Aminobenzimidazole That Inhibits and Disperses Gram-Positive Biofilms through a Zinc-Dependent Mechanism. J. Am. Chem. Soc., 2009, 131 (29), pp. 9868-9869).*
Tamm (Certain benximidazoles, benzenes, ribofuranosylpurines as inhibitors of influenza B virus multiplication. J Bacteriol. Jul. 1956; 72(1): 59-64).*
Budesinsky et al (5-Styryl-2-benzimidazolylurethanes as potential anthelminthics. Collect. Czech. Chem. Commun. 1975, 40, 1089-1094).*
Ohemeng et al (Receptor-based design of novel dihydrofolate reductase inhibitors: benzimidazole and indole derivatives. J. Med. Chem., 1991, 34 (4), pp. 1383-1394).*
Barrett, O.J.; Childs, J.L.; Disney, M.D. (2006) "Chemical microarrays to identify ligands that bind pathogenic cells," ChemBioChem, 7(12), 1882-1885.
Breitbach et al. (Sep. 2011), "Surface-mediated release of a synthetic small-molecule modulator of bacterial quorum sensing: Gradual release enhances activity," Chem. Commun., 47, 370-372.
Chen, Y.S.; Zhang, K.; Zhao, S.Q. (2009) "2-Amino-6-nitro-1H-benzoimidazol-3-ium chloride," Acta Crystallographica, Section E: Structure Reports Online, E65(8), o1926.

(Continued)

*Primary Examiner* — Jake M Vu
(74) *Attorney, Agent, or Firm* — Leydig, Voit & Mayer, Ltd.

(57) ABSTRACT

Compounds described herein inhibit biofilm formation or disperse pre-formed biofilms of Gram-negative bacteria. Biofilm-inhibitory compounds can be encapsulated or contained in a polymer matrix for controlled release. Coatings, films, multilayer films, hydrogels, microspheres and nanospheres as well as pharmaceutical compositions and disinfecting compositions containing biofilm-inhibitory compounds are also provided. Methods for inhibiting formation of biofilms or dispersing already formed biofilms are provided. Methods for treating infections of gram-negative bacteria which form biofilms, particularly those of *Pseudomonas* and more particularly *P. aeruginosa*.

9 Claims, 22 Drawing Sheets

(56) References Cited

OTHER PUBLICATIONS

Davies et al. (1998), "The Involvement of Cell-to-Cell Signals in the Development of a Bacterial Biofilm", Science, 280(5361):295-298.
El Ashry, E.S.H. et al. (2008) "Corrosion inhibitors part V: QSAR of benzimidazole and 2-substituted derivatives as corrosion inhibitors by using the quantum chemical parameters," Progress in Organic Coatings 61(1), 11-20. Abstract.
Ermolat'ev et al. (2008), "A Divergent Synthesis of Substituted 2-Aminoimidazoles from 2-Aminopyrimidines", J. Org. Chem., 73 (17):6691-6697.
Frei et al. (Feb. 2010), "Small Molecule Macroarray Construction via Palladium-Mediated CarbonCarbon Bond-Forming Reactions: Highly Efficient Synthesis and Screening of Stilbene Arrays," Chem.-Eur. J., 16, 2692-2695.
Frei et al. (Apr. 2012), "2-Aminobenzimidazole Derivatives Strongly Inhibit and Disperse *Pseudomonas aeruginosa* Biofilms," Angew. Chem., Int. Ed., 51(21): 5226-5229.
Fulghesu et al. (2007) "Evaluation of different compounds as quorum sensing inhibitors in Pseudomonas aeruginosa," Chemotherapy, 19(4):388-91.
Geske et al. (2005), "Small molecule inhibitors of bacterial quorum sensing and biofilm formation", J. Am. Chem. Soc., 127(37):12762-3.
Geske et al. (2008) "Expanding dialogues: from natural autoinducers to non-natural analogues that modulate quorum sensing in Gram-negative bacteria," Chem. Soc. Rev., 37(7):1432-47.
Glansdorp et al. (2004) "Synthesis and stability of small molecule probes for Pseudomonas aeruginosa quorum sensing modulation," Org. Biomol. Chem., 2, 3329-3336.
Graubaum, H. et al. (1984) "Acylation of heterocycles. 9. Preparation and rearrangement of 1-acetyl-2-aminobenzimidazoles," Zeitschrift fur Chemie, 24(2), 57-8. Abstract.
Grimmett, M. R. (2002) "Product class 4: benzimidazoles," Science of Synthesis, 12, 529-612. Abstract.
Hamley, P.; Tinker, A.C. (1995) "1,2-Diaminobenzimidazoles: selective inhibitors of nitric oxide synthase derived from aminoguanidine," Bioorganic & Medicinal Chemistry Letters, 5(15), 1573-6.
Hentzer et al. (2002) "Inhibition of quorum sensing in Pseudomonas aeruginosa biofilm bacteria by a halogenated furanone compound," Microbiology, 148(Pt 1):87-102.
Hranjec, M. et al.(Mar. 2011) "Synthesis, spectroscopic characterization and antiproliferative evaluation in vitro of novel Schiff bases related to benzimidazoles," European Journal of Medicinal Chemistry,, 46(6), 2274-2279 Abstract.
Huigens et al, (Dec. 2009), "The chemical synthesis and antibiotic activity of a diverse library of 2-aminobenzimidazole small molecules against MRSA and multidrug-resistant *A. baumannii*," Bioorganic & Medicinal Chemistry, 18(2), 663-674.
Joseph, L. (1963) "Substituted 2-aminobenzimidazoles,"J. Medicinal Chemistry (1963), 6(5), 601 Abstract.
Junker et al. (2007) "High-Throughput Screens for Small-Molecule Inhibitors of Pseudomonas aeruginosa Biofilm Development," Antimicrob. Agents Chemother. 2007, 51, 3582-3590.
Kim et al. (2008), "Furanone derivatives as quorum-sensing antagonists of Pseudomonas aeruginosa." Appl. Microbiol. Biotechnol. 2008, 80, 37-47.
Kuznetsov, Yu. I.; Podgornova, L. P. (2006) "Inhibition of copper and zinc dissolution with 5(6)-nitrobenzoimidazoles in phosphate electrolytes." Protection of Metals, 42(1), 69-74. Abstract.
Lee et al. (Jul. 2010) "3-indolylacetonitrile decreases *Escherichia coli* O157:H7 biofilm formation and *Pseudomonas aeruginosa* virulence," Environ. Microbiol., 13(1):62-73.
Li et al. (2003) "Palladium-catalyzed regioselective arylation of imidazo[1,2-a]pyrimidine," Org. Lett., 5(25):4835-4837.
Li, Y-F et al. (2007) "Identification of 1-isopropylsulfonyl-2-amine benzimidazoles as a new class of inhibitors of hepatitis B virus," European J. Medicinal Chemistry, 42(11-12), 1358-1364.
Liu et al. (Mar. 2011) "A New Small Molecule Specifically Inhibits the Cariogenic Bacterium *Streptococcus mutans* in Multispecies Biofilms," Antimicrob. Agents Chemother., 55(6): 2679-2687.

Lopez-Vallejo, F. et al. (2007) "Molecular modeling of some 1H-benzimidazole derivatives with biological activity against *Entamoeba histolytica*: A comparative molecular field analysis study," Bioorganic & Medicinal Chemistry, 15(2), 1117-1126. Abstract.
Lopyrev, V. A et al. (1985) "Investigation of benzimidazoles. 5—Transmission of the substituent effects in 2-substituted 5(6)-nitrobenzimidazoles studied by proton, carbon-13 and nitrogen-15 NMR spectroscopy," Magnetic Resonance in Chemistry, 23(5), 301-4.
Lopyrev, V. A. et al. (1985) "Investigation of benzimidazoles. 6—Transmission of substituent effects in dianion radicals of 2-substituted 5(6)-nitrobenzimidazoles studied by ESR spectroscopy," Magnetic Resonance in Chemistry, 23(5), 305-10. Abstract.
Madden,J. et al.(Jun. 2010) "Fragment-based discovery and optimization of BACE1 inhibitors," Bioorganic & Medicinal Chemistry Letters, 20(17), 5329-5333. Abstract.
Mani et al. (2006), "In Vitro Characterization of the Antibacterial Spectrum of Novel Bacterial Type II Topoisomerase Inhibitors of the Aminobenzimidazole Class," Antimicrob. Agents Chemother., 50(4):1228-1237. Abstract.
Mohanazadeh, F. et al. (May 2011) "Efficient synthesis of 2-arylamino-2-imidazolines and 2-aminobenzimidazoles with aminoiminomethane sulfonic acid derivatives," Chinese Journal of Chemistry (2011), 29(5), 1055-1058.
Mpamhanga, C. P. et al. (2009) "One Scaffold, Three Binding Modes: Novel and Selective Pteridine Reductase 1 Inhibitors Derived from Fragment Hits Discovered by Virtual Screening," J. Medicinal Chemistry, 52(14), 4454-4465. Abstract.
Musk et al. (2005) "Iron Salts Perturb Biofilm Formation and Disrupt Existing Biofilms of *Pseudomonas aeruginosa*," Chemistry & Biology, 12:789-796.
Ogretir, C.; Demirayak, S. (1986) "Benzimidazole studies. IV. Investigation of the nitration kinetics of some benzimidazole derivatives and Hammett relationships," Chimica Acta Turcica, 14(2), 199-211. Abstract.
Palmer, A. G.; Streng, E.; Blackwell, H. E. (Oct. 2011) "Attenuation of virulence in pathogenic bacteria using synthetic quorum-sensing modulators under native conditiond on plant hosts," ACS Chem. Biol., 6(12) 1348-1356.
Perez-Villanueva, J. et al. (May 2011) "Comparative molecular field analysis (CoMFA) and comparative molecular similarity indices analysis (CoMSIA) of some benzimidazole derivatives with trichomonicidal activity," European Journal of Medicinal Chemistry, 46(8), 3499-3508.
Perisic-Janjic, N. et al. (1999) "Physicochemical properties and antibacterial activity of Cu(II) complexes with some benzimidazole derivatives," Acta Periodica Technologica, 29-30, 173-181. Abstract.
Powers, J. P. et al. (2006) "Discovery and initial SAR of inhibitors of interleukin-1 receptor-associated kinase-4," Bioorganic & Medicinal Chemistry Letters, 16(11), 2842-2845.
Richards et al. (2009), "Small molecule approaches toward the non-microbicidal modulation of bacterial biofilm growth and maintenance," Anti-Infective Agents Med. Chem., 8: 295-314.
Rogers et al. (2009) "A 2-aminobenzimidazole that inhibits and disperses gram-positive biofilms through a zinc-dependent mechanism," J. Am. Chem. Soc., 131(29):9868-9.
Sambanthamoorthy et al. (Jun. 2011) "Identification of a novel benzimidazole that inhibits bacterial biofilm formation in a broad-spectrum manner," Antimicrob. Agents Chemother., 55(9):4369-78.
Simonov, A. M.; Pozharskii, A. F.; Marianovskii, V. M. (1967) "Some new 1-substituted 2-amino-5,6-dimethylbenzimidazoles," Indian Journal of Chemistry 5(2), 81-2.
Sintim et al. (Jun. 2010) "Paradigm shift in discovering next-generation anti-infective agents: targeting quorum sensing, c-di-GMP signaling and biofilm formation in bacteria with small molecules," Future Med. Chem., 2(6):1005-1035.
Valdez et al. (2002) "Synthesis and antiparasitic activity of 1H-benzimidazole derivatives," Bioorg. Med. Chem. Lett., 12(16):2221-4.
Yang et al. (2007) "Meta conjugation effect on the torsional motion of aminostilbenes in the photoinduced intramolecular charge-transfer state," J. Am. Chem. Soc., 129(43):13183-92.

\* cited by examiner

INHIBITION AND DISPERSION OF BACTERIAL BIOFILMS WITH 2-AMINOBENZIMIDAZOLE DERIVATIVES

CROSS-REFERENCE TO RELATED APPLICATIONS

This application claims the benefit of U.S. provisional application 61/555,646, filed Nov. 4, 2011 which is incorporated by reference herein in its entirety.

STATEMENT REGARDING GOVERNMENT SUPPORT

This invention was made with government support under AI063326 awarded by the National Institutes of Health and N00014-07-1-0255 awarded by the NAVY/ONR. The government has certain rights in the invention.

BACKGROUND OF THE INVENTION

Bacteria can grow into surface-associated communities termed biofilms that are pervasive virtually everywhere on earth. [1] This mode of growth poses a significant obstacle to the successful treatment of infectious disease, with an estimated 80% of human infections in the biofilm state. [2] Biofilms are particularly problematic to clear due to their encasement in a protective and impermeable extracellular matrix, [3] which render biofilm-associated bacteria resistant to both host immune responses and standard antibiotic agents. Indeed, treatment with ~10-1000-fold higher doses of antibiotic is often required for biofilm clearance relative to planktonic bacteria. [2] Biofilm growth by the Gram-negative bacterium *Pseudomonas aeruginosa* has attracted particular attention, as biofilms of this pathogen are the origin of the fatal chronic lung infections in most cystic fibrosis patients. [4] *P. aeruginosa* biofilm infections also plague burn victims, AIDS patients, and are endemic on the medical implants and devices universal in healthcare today. [5]

As such, the development of new methods to attenuate bacterial biofilm growth is of significant importance and represents a major research area. [6] Small molecules capable of inhibiting the growth of biofilm and particularly those capable of removing (i.e., dispersing) preformed biofilms would be extremely useful to combat bacterial infection in a range of applications in industry, agriculture, and the environment. [7]

Molecules exhibiting these properties however, remain rare. [5-14] This invention relates to a chemical approach for the inhibition and dispersion of bacterial biofilm, particularly those of Gram negative bacterial, more particularly those of *Pseudomonas* species and specifically those of *P. aeruginosa*, which is based on 2-aminobenzimidazoles.

Biofilm growth only occurs after a critical bacterial cell density is achieved, and in many bacteria is under the direct control of the cell-cell signaling pathway termed quorum sensing (QS). [6,7,15] Notably, *P. aeruginosa* mutants lacking a functional QS system are unable to grow into mature biofilms and are largely avirulent. [16,17] It has been shown, that non-native analogs of natural N-acylated L-homoserine lactone (AHL) QS signals can strongly modulate QS in Gram-negative bacteria, [18] and several of these AHLs also attenuate biofilm growth in *P. aeruginosa*. [11] One challenge to the application of AHLs as biofilm or QS inhibitors, however, is the hydrolytic instability of the lactone head group. [19] Hydrolyzed AHLs are biologically inactive, and therefore additional measures (e.g., multiple dosing, controlled delivery, etc.) are required for sustained activity of AHLs. [20, 21] Furthermore, and of particular relevance to biofilms, many AHL-derived biofilm inhibitors failed to disperse preformed biofilms, similar to most antibiotics. [11] In this context, there is a significant need in the art to identify hydrolytically stable molecular scaffolds for QS and/or biofilm modulation with enhanced activities.

Bacterial quorum sensing systems comprise small molecules, e.g., certain acyl-homoserine lactones, to regulate, in a cell-density dependent manner, a wide variety of physiological processes unique to the life-cycle of each microbe. These processes, which are collective designated "symbiotic behavior" herein, include: swarming, motility, sporulation, biofilm formation, conjugation, bioluminescence and/or production of pigments, antibiotics and enzymes.

A few natural products have been reported to inhibit bacterial QS or biofilm growth. The halogenated furanones from the macroalga *Delisea pulchra* have seen the most intensive study in this regard. [9] Three other notable examples include bromoageliferin, 3-indolylacetonitrile, and resveratrol (Scheme 1). Bromoageliferin displays anti-biofilm activity in the Gram-negative bacterium *Rhodospirillum salexigens*, and recently Melander and co-workers have reported simplified analogs of this marine natural product with anti-biofilm activities, most notably, certain 2-aminoimidazole (2-AI) derivatives in Gram-negative bacteria [8] and 5-amido or 5-imido 2-aminobenzimidazole (2-ABI) derivatives in Gram-positive bacteria. [22] The plant auxin 3-indolylacetonitrile was reported to inhibit the formation of *P. aeruginosa* biofilms via a QS-dependent mechanism, [23] and the phytoalexin resveratrol [24] and related stilbene derivatives [25] have recently been reported to inhibit the LuxR-type QS receptors in Gram-negative bacteria.

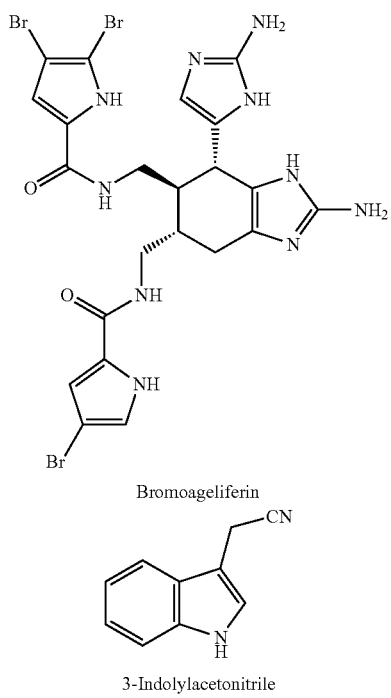

Scheme 1

Bromoageliferin

3-Indolylacetonitrile

-continued

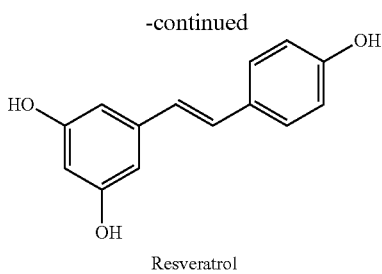

Resveratrol

Published PCT application, WO 2010/144686 (Melander et al.) reports the inhibition of *P. aeruginosa* and *Acinetobacter baumannii* biofilm formation by certain 2-aminobenzimidazole (2-ABI) derivatives. Specifically tested compounds are listed in Scheme 1 therein (compounds 2-16, all of which carry a substituent bonded to the benzimidazole ring with a C—N bond. This PCT application is incorporated by reference herein. These 2-ABI derivatives are reported not to inhibit biofilm formation of the tested Gram negative bacteria at 100 microM concentration. In contrast, these 2-ABI derivatives are reported to inhibit biofilm development at a concentration of 100 microM of at least two of the Gram-positive bacteria: MRSA (presumably Methicillin-resistant *Staphylococcus aureus*), vancomycin-resistant *Enterococcus faecium* (VRE), or *Staphylococcus epidermidis*. In Table 1, therein, $IC_{50}$ and $EC_{50}$ values are provided corresponding to the concentration of compound that inhibits 50% biofilm development and the concentration that disperses 50%, respectively, of a pre-formed biofilm of one of the listed Gram-positive bacteria. The data in Table 1 therein are incorporated by reference herein. Compound 3 therein is reported to exhibit the best activity profile. The representative biofilm inhibitor, compound 3, is also asserted to operate via a Zn(II)-dependent mechanism. The application further reports that two control compounds (17 and 18, therein) did not inhibit MRSA, VRE or *S. epidermidis* biofilm formation at 100 microM.

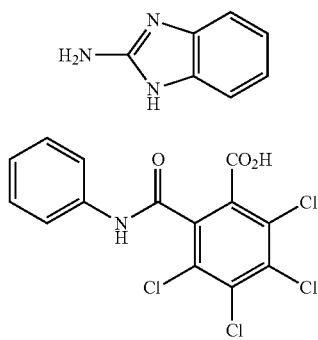

The 2-AB1 molecules (presumably of Table 1) are asserted to be "some of the most potent anti-biofilm agents identified to date that do not operate through a microbiocidal mechanism." This reference is incorporated by reference herein in its entirety for descriptions of experiments performed and materials employed in such experiments.

US published application 2008/0181923 (Melander et al.) relates to various imidazole based compounds. Specifically tested compounds, listed at least in part in Table 1, therein, are reported to inhibit biofilm formation of listed bacteria, including *Pseudomonas aeruginosa*. This reference is incorporated by reference herein in its entirety for descriptions of experiments performed and materials employed in such experiments.

Published PCT application 2004/047769 relates to certain benzimidazoles and analogs thereof which are reported to possess antibacterial activity. Compounds were reported evaluated for in vitro antibacterial activity against *S. aureus* and *E. coli* (see Tables, therein). This reference is incorporated by reference herein in its entirety for descriptions of compounds prepared, methods of synthesis, antibacterial activity experiments performed and materials employed in such experiments.

SUMMARY OF THE INVENTION

The present invention relates to compounds which inhibit biofilm formation or disperse pre-formed biofilms of Gram-negative bacteria, and which have formula I:

I and salts thereof,
where:
each $R_1$, independently, is selected from hydrogen, a halogen, an optionally-substituted alkyl group; an —O—$R_{10}$, a —$COR_{10}$, a —$OCOR_{10}$, —$CH_2COR_{10}$, or a —$COOR_{10}$ group;
$R_2$ and $R_3$, independently, are selected from hydrogen; a halogen; an optionally substituted alkyl group; a cycloalkyl group, a haloalkyl group; a nitro group; a cyano group; a vinyl group substituted with an alkyl, a cycloalkyl, an alicyclic, a heterocyclic, an aryl, an arylalkyl, a heteroaryl, or a heteroarylalkyl group, each of which group is optionally substituted; an —O—$R_{10}$, a —$COR_{10}$, a —$OCOR_{10}$, —$CH_2COR_{10}$, or a —$COOR_{10}$ group, where $R_{10}$ is hydrogen, an alkyl, a cycloalkyl, an alicyclic group, a heterocyclic, an aryl, or a heteroaryl group, each of which groups is optionally substituted; or $R_2$ and $R_3$ optionally together form a 5-, 6- or 7-member alicyclic, heterocyclic, aryl or heteroaryl ring, any of which rings is optionally substituted;
$R_4$ is selected from hydrogen, an alkyl group, an aryl group, an arylaklyl group, an alicyclic group, a heteroaryl group, or a heteroarylalkyl group, each of which is optionally substituted; and
$R_5$ and $R_6$, independently, are selected from hydrogen, an optionally substituted alkyl group, or optionally together form a 5-, 6- or 7-member alicyclic or heterocyclic ring which ring is optionally substituted,
where optional substitution is substitution of an indicated group by 1-10 substituents, dependent upon group valence, selected from a halogen; an unsubstituted alkyl group; a nitro group; a cyano group; a —$OR^{11}$ group, a —$COR_{11}$ group, a —$CH_2$—$COR_{11}$ group, a —$OCOR_{11}$ group; a —$CO_2R_{11}$ group; or a substituted alkyl group or substituted phenyl group, each of which is substituted with 1-6 substituents selected from halogen, a hydroxyl group, a nitro group, a cyano group, an unsubstituted alkyl group, an unsubstituted phenyl group, an unsubstituted phenalkyl group, a —COR$_{12}$ group, a —CH$_2$—COR$_{11}$ group, a —OCO—R$_{12}$ group, a —COOR$_{12}$ group, and where:

R$_{10}$ is hydrogen, an alkyl, an aryl, or a heteroaryl group, each of which groups is optionally substituted;

R$_{11}$ is selected from hydrogen, an unsubstituted alkyl, an unsubstituted phenyl group, an alkyl group substituted with an unsubstituted phenyl group (i.e., an unsubstituted phenalkyl group), a halogen-substituted alkyl group, or a halogen-substituted phenyl group; and R$_{12}$ is hydrogen, or an unsubstituted alkyl group.

In specific embodiments, optional substitution is substitution with 1-10 substituents selected from halogen; a hydroxyl group; a nitro group; a cyano group; an unsubstituted alkyl group; an unsubstituted alkoxy group; an unsubstituted phenyl group; a halo-substituted phenyl group; an alkyl group substituted with an unsubstituted phenyl group (an unsubstituted phenalkyl group); an alkyl group substituted with a halogen-substituted phenyl group (a halogen-substituted phenalkyl group); a —COH group; a —COOH group; a —OCOR$_{12}$ group, a —COR$_{12}$ or —COOR$_{12}$ group, where R$_{12}$ is an unsubstituted alkyl, an unsubstituted phenyl, an alkyl group substituted with a phenyl group, an alkyl group substituted with a halo-substituted phenyl group, halo-substituted phenyl group, or alkyl-substituted phenyl group. In specific embodiments, alkyl groups of substituents are C1-C3 alkyl groups. In specific embodiments, alkyl groups of R$_{12}$ groups are C1-C6 alkyl group or C1-C3 alkyl groups.

In specific embodiments, optionally substitution is substitution by 1-10 substituents selected from halogen, a hydroxyl group, a nitro group, a cyano group, an unsubstituted alkyl group, an unsubstituted alloy group, an unsubstituted phenyl group, an unsubstituted benzyl group, a —CF$_3$ group, a —COH group, an acetyl group, or a —COOH group.

In specific embodiments, optional substitution is substitution by 1-10 substituents selected from halogens or unsubstituted C1-C3 alkyl groups.

In specific embodiments, phenyl rings are substituted with 1-10 substituents selected from halogen, a hydroxyl group, a nitro group, a cyano group, a halogen-substituted alkyl group, an unsubstituted alkyl group, an unsubstituted alloy group, a —COH group, a —COOH group, or a —COR$_{12}$ or —COOR$_{12}$ group as defined above. In specific embodiments, alkyl and alloy group substituents of phenyl rings are C1-C3 alkyl groups.

In specific embodiments, phenyl rings are substituted with 1-10 substituents selected from fluorine, bromine, chlorine, a nitro group, a cyano group, a —CF$_3$ group, a methyl group, or an ethyl group.

In specific embodiments, alicyclic groups have 3-15 carbon atoms, contain at least one 3-10 member ring, where 1 or 2 ring carbons are optionally replaced with —CO—, which optionally contain 1 or 2 double bonds and which optionally contain 1-3 heteroatom ring atoms selected from N, O or S where valency requirements may be satisfied by substitution as described herein. In more specific embodiments, alicyclic groups contain 1, 2 or 3 rings which optionally contain 1-3 heteroatoms selected from N, S or O, which optionally contain 1 or 2 double bonds, where 1 or 2 ring carbons are replaced with —CO— and where valency requirements may be satisfied by substitution as described herein. In specific embodiments, alicylic groups do not contain N atoms.

In specific embodiments, heterocyclic groups have 5-15 carbon atoms, contain at least one 5- or 6-member ring having 1, 2 or 3 heteroatoms, where 1 or 2 ring carbons are optionally replaced with —CO— and where valency requirements may be satisfied by optional substitution as described herein. In specific embodiments, heterocyclic groups have one 5- or 6-member ring, with 1-3 heteroatoms selected from N, O or S, optionally have one or two double bonds, and optionally have one carbon replaced with —CO—. In specific embodiments, heterocyclic groups do not contain N atoms.

In specific embodiments, heteroaryl groups have one or two heteroaromatic rings having 1-6 heteroatoms or 1-3 heteroatoms. In specific embodiments, heteroaryl groups, have one 5- or 6-member ring having 1-3 heteroatoms selected from O, S, or N.

In specific embodiments, R$_2$ and R$_3$ together form a 5- or 6-member alicyclic, heterocyclic, aryl or heteroaryl ring, any of which rings is optionally substituted. In specific embodiments, R$_2$ and R$_3$ together form and unsubstituted 5- or 6-member alicyclic or heterocyclic ring, where one carbon of the noted ring is optionally replaced with —CO—, where the noted ring optionally contains 1 or 2 double bonds. In an embodiment the heterocyclic ring formed can specifically contain 1 or 2 heteroatoms. Heteroatoms in the heterocyclic ring can be N, O or S.

In specific embodiments, R$_5$ and R$_6$ together form a 5- or 6-member alicyclic, heterocyclic, aryl or heteroaryl ring, any of which rings is optionally substituted. In specific embodiments, R$_2$ and R$_3$ together form and unsubstituted 5- or 6-member alicyclic or heterocyclic ring, where one carbon of the noted ring is optionally replaced with —CO—, where the noted ring optionally contains 1 or 2 double bonds. In an embodiment the heterocyclic ring formed can specifically contain 1 or 2 heteroatoms. Heteroatoms in the heterocyclic ring can be N, O or S.

In specific embodiments, optional substitution is substitution by 1-6 or by 1-3 substituents as defined herein.

In specific embodiments, alkyl groups of R$_1$-R$_3$ are C1-C3 alkyl groups. In specific embodiments, alkyl groups of R$_4$-R$_6$ are C1-C6 alkyl groups or C1-C3 alkyl groups. In specific embodiments, alkyl groups of R$_1$-R$_3$ are unsubstituted C1-C3 alkyl groups. In specific embodiments, alkyl groups of R$_4$-R$_6$ are unsubstituted C1-C6 alkyl groups or unsubstituted C1-C3 alkyl groups. In specific embodiments, alkyl groups of R$_1$-R$_6$ are substituted with one or more halogens, particularly fluorine or chlorine, or one or more hydroxyl groups.

In specific embodiments, R$_2$ or R$_3$ is a R$_7$HC=C— group, where R$_7$ is hydrogen, an alkyl, an aryl, an arylalkyl, a heteroaryl, or a heteroarylalkyl group, each of which groups is optionally substituted. In specific embodiments, R$_7$ is a group other than hydrogen. More specifically R$_7$ is an optionally substituted alkyl group or an unsubstituted alkyl group. In specific embodiments R$_2$ or R$_3$, when R$_7$ is not hydrogen, is a trans-R$_7$HC=C—. In specific embodiments, R$_7$ is an aryl, or an arylalkyl group.

In specific embodiments, none of R$_1$-R$_7$ contains a nitrogen. In specific embodiments, none of R$_1$-R$_7$ is or contains a —COOH group. In specific embodiments, none of R$_1$-R$_7$ is or contains a nitro group.

In specific embodiments, at least one of R$_1$-R$_6$ is an atom or group other than hydrogen.

In specific embodiments, when R$_1$, and R$_4$-R$_6$ are hydrogen, neither of R$_2$ or R$_3$ is —COOH.

In specific embodiments, each R$_1$ is independently selected from hydrogen, halogen, an unsubstituted C1-C3 alkyl group, or a halogen-substituted C1-C3 alkyl group. More specifically, each R$_1$ is independently hydrogen, fluorine, bromine, chlorine, a methyl group, an ethyl group or a —CF$_3$ group. In other specific embodiments, both R$_1$ are hydrogen.

In specific embodiments, R$_4$ is hydrogen or an unsubstituted C1-C3 alkyl group.

In specific embodiments, R$_5$ and R$_6$ are selected from hydrogen or an unsubstituted C1-C3 alkyl group. In specific embodiments, R$_5$ and R$_6$ are both hydrogen. In specific embodiments, R$_5$ and R$_6$ together with N form a 5- or 6-member heterocyclic ring, having one nitrogen, two nitrogens, or a nitrogen and an oxygen in the ring. In specific embodiments, —NR$_5$R$_6$ is selected from optionally substituted piperidinyl, piperazinyl, morpholinyl, pyrrolidinyl, pyrazolidinyl, or imidazolidinyl groups. In specific embodiments, optional substitution of such —NR$_5$R$_6$ groups is on one or more ring carbon atoms or on the second N in the ring as described above. In specific embodiments, optional substitution of such —NR$_5$R$_6$ groups includes ring carbon substitution with one or more optionally substituted C1-C3 alkyl groups and substitution of the second N in the ring with an optionally substituted C1-C3 alkyl group.

In specific embodiments, R$_2$ and R$_3$, independently, are selected from a hydrogen, a halogen, an optionally substituted C1-C3 alkyl group, a C1-C3 alkoxyl group, a C1-C3 haloalkyl group, a nitro group, a cyano group, or a —COR$_{10}$ or a —COOR$_{10}$ group, where R$_{10}$ is hydrogen, a C1-C6 alkyl, an aryl, or a heteroaryl group, each of which R$_{10}$ groups is optionally substituted, where at least one of R$_1$ or R$_2$ is not hydrogen.

In specific embodiments, one of R$_2$ or R$_3$ is a vinyl group substituted with an alkyl, an aryl, an arylalkyl, a heteroaryl, or a heteroarylalkyl group, each of which group is optionally substituted. In specific embodiments, one of R$_2$ or R$_3$ is a vinyl group substituted with an aryl, an arylalkyl, a heteroaryl, or a heteroarylalkyl group, each of which group is optionally substituted. In specific embodiments, one of R$_2$ or R$_3$ is a vinyl group substituted with an aryl, or an arylalkyl group, each of which group is optionally substituted. In specific embodiments, one of R$_2$ or R$_3$ is a vinyl group substituted with phenyl group or a benzyl group, each of which group is optionally substituted. In specific embodiments, one of R$_2$ or R$_3$ is a vinyl group substituted with an optionally substituted phenyl group. In specific embodiments, one of R$_2$ or R$_3$ is a vinyl group substituted with a phenyl group which is optionally substituted with 1-6 substituents selected from halogen, a hydroxyl group, unsubstituted C1-C3 alkyl, unsubstituted C1-C3 alkoxy, halogen-substituted C1-C3 alkyl, a nitro group, or a cyano group. In more specific embodiments of the foregoing embodiments, the other or R$_2$ or R$_3$ is hydrogen, a methyl group, an ethyl group or a —CF$_3$ group.

In a specific embodiment, salts of the biofilm inhibitors of this invention are pharmaceutically acceptable salts.

In more specific embodiments of the foregoing embodiments, the group substituted on the vinyl group is substituted on the vinyl group in the trans configuration with respect to the benzimiazole ring, as illustrated in formulas IA1 and 1A2,

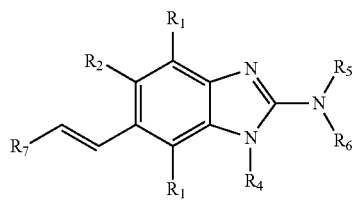

-continued

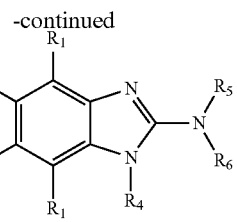

and salts thereof
where R$_1$-R$_6$ are as defined above and R$_7$ is an alkyl, an aryl, an arylalkyl, a heteroaryl, or a heteroarylalkyl group, each of which groups is optionally substituted. In specific embodiments of formulas IA1 and IA2, R$_5$ and R$_6$ are independently hydrogen or unsubstituted C1-C3 alkyl. In specific embodiments of formulas IA1 and IA2, R$_5$ and R$_6$ together with N form a 5- or 6-member heterocyclic ring, having one nitrogen, two nitrogens, or a nitrogen and an oxygen in the ring. In more specific embodiments, —NR$_5$R$_6$ is selected from optionally substituted piperidinyl, piperazinyl, morpholinyl, pyrrolidinyl, pyrazolidinyl, or imidazolidinyl groups. In specific embodiments of formulas IA1 and IA2, all of R$_1$-R$_4$ are hydrogens or unsubstituted C1-C3 alkyl groups. In other specific embodiments, R$_1$, and R$_2$ or R$^3$ are all hydrogens. In specific embodiments, R$_4$ is hydrogen.

In specific embodiments, R$_7$ groups are optionally substituted with 1-6 substituents selected from a halogen; a hydroxyl group; a nitro group; a cyano group; an unsubstituted alkyl group; an unsubstituted alkoxy group; an unsubstituted phenyl group; a halo-substituted phenyl group; an alkyl group substituted with an unsubstituted phenyl group (an unsubstituted phenalkyl group); a alkyl group substituted with a halogen-substituted phenyl group (a halogen-substituted phenalkyl group); a —COH group; a —COOH group; a —COR$_{12}$ or —COOR$_{12}$ group, where R$_{12}$ is an unsubstituted alkyl, an unsubstituted phenyl, an alkyl group substituted with a phenyl group, a alkyl group substituted with a halo-substituted phenyl group, halo-substituted phenyl group, or alkyl-substituted phenyl group. In more specific embodiments, R$_7$ groups are optionally substituted with one or more halogens, C1-C3 alkyl groups, nitro groups, cyano groups, —COH groups, one or more —COR$_{12}$ groups where R$_{12}$ is a C1-C3 alkyl or a phenyl group, C1-C3 alkoxy group, or a haloalkyl group.

In specific embodiments, R$_7$ is an aryl group, particularly a phenyl group, or an arylalkyl group, particularly a benzyl group. In a specific embodiment, R$_7$ is a halogen-substituted phenyl group.

In specific embodiments, one of R$_2$ or R$_3$ are a methyl group, an ethyl group, a propyl group, a methoxy group, a phenoxy group, a benzyloxy, an ethoxy group, a propoxy group, fluorine, chlorine, bromine, iodine, an acetyl group, an acetoxy group, a benzoyl group, a benzoyloxy group, a methoxycarbonyl group, a phenoxycarbonyl group, or a phenacyl group. In specific embodiments, one or both of R$_2$ and R$_3$ are fluorine, chlorine, bromine, iodine, an unsubstituted C1-C3 alkyl groups, or a halogen-substituted C1-C3 alkyl group, and the other of R$_2$ or R$_3$ is hydrogen.

In additional specific embodiments, the invention relates to compounds of formula IB:

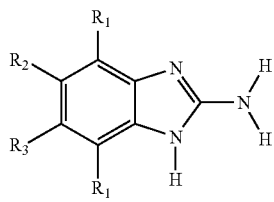

and salts thereof
where $R_1$-$R_3$ are as defined above.

The invention provides methods for inhibiting biofilm formation of a Gram-negative bacterium, particularly of a bacterium of the species *Pseudomonas* and more particularly of *Pseudomonas aeruginosa*. In this method the bacteria or biofilm thereof is contacted with an effective amount of one or more compounds of formula I, formula IA1, formula IA2 or formula IB or a salt thereof.

The invention additionally provides a method for dispersing an already formed biofilm of a Gram-negative bacterium, particularly of a bacterium of the species *Pseudomonas* and more particularly of *Pseudomonas aeruginosa*. In this method, the pre-formed biofilm is contacted with an effective amount of one or more compounds of formula I, formula IA1, formula IA2 or formula IB or a salt thereof.

Biofilm inhibition or dispersement can be in vivo or in vitro.

The invention thus also provides a method for treating infections of Gram-negative bacteria in an individual in need of such treatment wherein a therapeutically effective amount of one or more compounds of formula I or a pharmaceutically acceptable salt thereof are administered to said individual.

The invention also provides therapeutic compositions for treating infections of Gram-negative bacteria comprising a therapeutically effective amount of one or more compounds of formula I or a pharmaceutically acceptable salt thereof and a pharmaceutically acceptable carrier. In a specific embodiment, such therapeutic compositions comprise one or more compounds of formulas 1A1, 1A2 or IB or a pharmaceutically acceptable salt thereof.

In an additional embodiment, the invention provides compounds of formulas herein and methods for reducing bacterial virulence and increasing susceptibility of quorum sensing bacterial to biocides and/or antibiotics.

In an additional embodiment, the invention provides compounds of formulas herein and methods for modulation of quorum sensing of bacteria, particularly quorum sensing bacteria which are Gram-negative bacteria and more particularly bacteria of the species *Pseudomonas*, including *P. aeruginosa*. In an embodiment, the compounds of the present invention are able to act as replacements for naturally occurring bacterial quorum sensing ligands in a ligand-protein binding system; that is, they imitate the effect of natural ligands and produce an agonistic effect. In another embodiment, the compounds of the present invention are able to act in a manner which disturbs or inhibits the naturally occurring ligand-protein binding system in quorum sensing bacteria; that is, they produce an antagonistic effect.

In another embodiment, the invention provides methods of reducing the virulence of quorum sensing bacteria, particularly quorum sensing bacteria which are Gram-negative bacteria and more particularly bacteria of the species *Pseudomonas*, including *P. aeruginosa*. In one aspect, the method comprises contacting a bacterium with an effective amount of a compound of the present invention. In another aspect, the method comprises contacting a bacterium with a therapeutically effective amount of a pharmaceutically acceptable salt of one or more compounds of the present invention. In yet another aspect, the method comprises contacting a bacterium with a precursor which can form an effective amount of a compound of the present invention. In an embodiment, the methods of the present invention can be used for inhibiting or diminishing the symbiotic behavior of a quorum sensing bacteria. In another embodiment, the methods of the present invention can be used for stimulating, initiating, or enhancing a symbiotic behavior of quorum sensing bacteria. In another embodiment, the methods of the present invention can be used for stimulating, initiating, or enhancing a symbiotic behavior, other than biofilm formation, of quorum sensing bacteria.

Methods of this invention can be implemented employing thin films, multilayers, coatings, hydrogels, encapsulation and related delivery methods where the biofilm-inhibitory compounds are loaded in the films, coatings, hydrogels or are encapsulated for delivery over time to an environment having existing biofilms or which is susceptible to biofilm formation. Encapsulation can be in various forms including among others microspheres or nanospheres. The use of such delivery methods can provide for release of one or more biofilm-inhibitory compounds over time extending from days to week to months dependent upon the methods and specific materials employed. In specific embodiments, a surface is protected from biofilm formation by application of a thin film, a multilayer, a coating or the like to at least a portion of the surface. In a related embodiment, surfaces are protected from biofilm formation or cleaned of biofilms by application of a thin film, a multilayer, a coating or the like to a surface in the vicinity of the surfaces to be protected in order to release an effective amount of biofilm-inhibitory compound of the invention into the vicinity of the surfaces to be protected. In specific embodiments, films, multilayers, coatings or encapsulation methods provide a level of the biofilm-inhibitory compound to the surface or to the vicinity of a surface to be protected which ranges from the $IC_{50}$ of the compound for biofilm inhibition to less than the toxicity level of the compound for mammalian cells. In specific embodiments, the concentration of biofilm-inhibitory compounds provided by such films, multilayers, coatings or encapsulation methods to the environment to be protected ranges from the IC50 of the compound to less than 0.25 mM. More specifically, the concentration provided to the environment to be protected ranges from 10-100 micromolar.

In specific embodiments, films, multilayers and coatings generated using one or more polymers and which contain from about 0.001 to 1 mg or more preferably from 0.01 to 1 mg/gram of biofilm-inhibitory compound/gram of polymer are useful for biofilm inhibition or dispersion. In a specific embodiment, biofilm-inhibitory compounds of the invention are provided to a surface or a portion of a surface in film formed from a poly(lactide-co-glycolide).

In additional embodiments, this invention provides novel compounds of formula I or salts thereof, particularly pharmaceutically acceptable salts thereof. In more specific embodiments, the invention provides compounds of formulas IA1 or IA2 or IB or salts thereof or pharmaceutically acceptable salts thereof.

DETAILED DESCRIPTION OF THE INVENTION

Figures 1A, 1B:
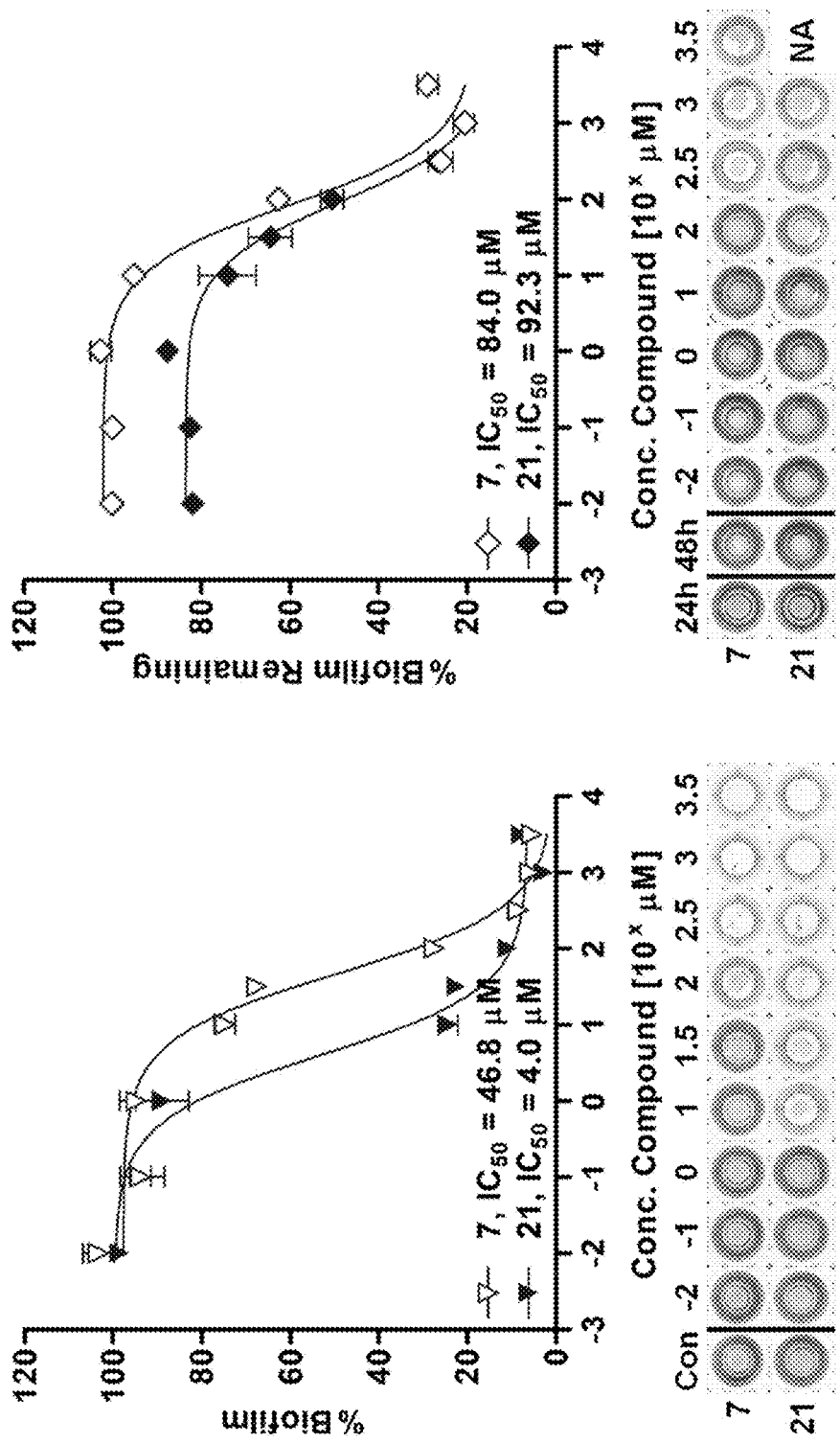
FIG. 1A-D illustrates dose-response curves and images of crystal violet biofilm inhibitory (A), dispersion (B) assays for compounds 7 (open triangles) and 21 (closed triangles) in *P. aeruginosa* (PA01). NA=not available. Dose-response curves for compounds 7 and 21 in *P. aeruginosa* PAO1/plasI-LVgfp (c) and PAO1/pRhl-LVAgfp (D) reporter strains.

As part of the work leading to this invention, stilbene derivatives containing 2-AI (2-aminoimidazole) or indole moieties (Scheme 2) were synthesized. The 2-ABI-stilbene derivative 1 was synthesized by initial formation of the stilbene framework via the Heck reaction, and then a tin (II) dichloride reduction to form the diamine intermediate. Condensation with cyanogen bromide afforded stilbene 1. 2-AI-stilbene 2 was generated in good yield via the palladium-catalyzed regioselective arylation of imidazo[1,2-a]pyrimidine [26] followed by hydrazine-mediated pyrimidine ring cleavage. [27] Indole-stilbenes 4a-b were synthesized via Heck reactions according to published methods. [28]

Scheme 2: Synthesis of stilbene derivatives.

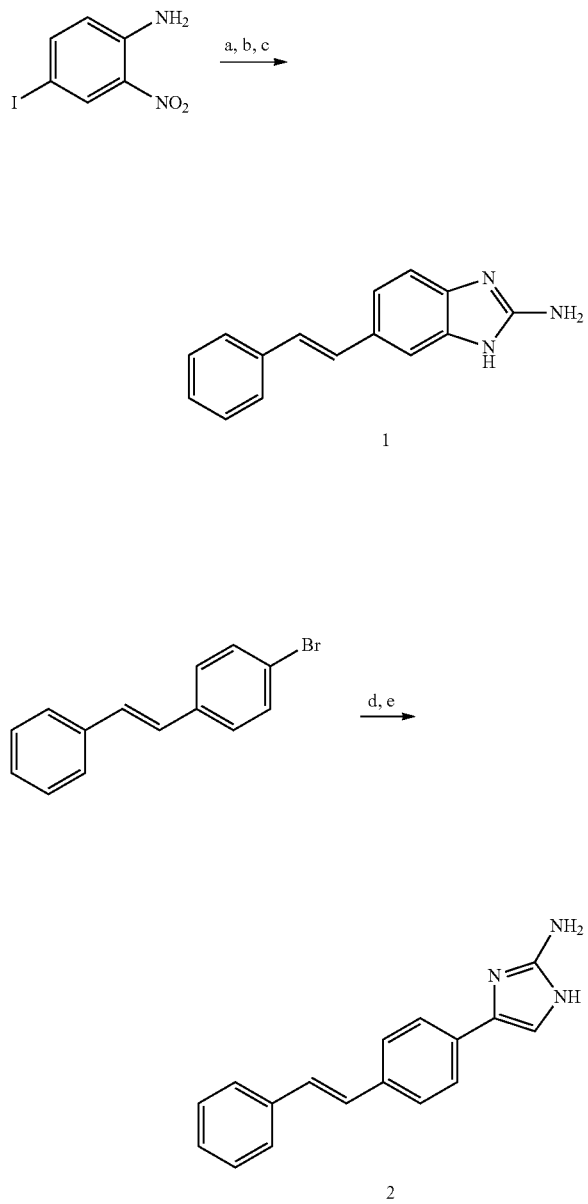

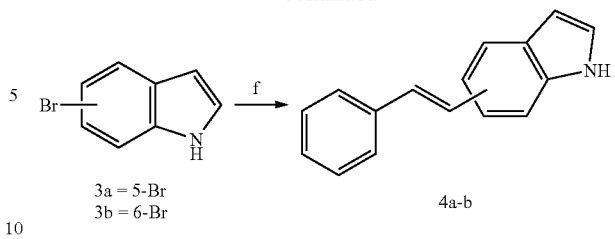

Reaction conditions: (a) Styrene, $Pd(OAc)_2$, $CH_3CN$, DIPEA, 80° C., 76%; (b) $SnCl_2.2H_2O$, EtOAc, 80° C.; (c) CNBr, $MeOH:H_2O$ 1:1, 50° C., 91% (over two steps); (d) Imidazo[1,2-a]pyrimidine hydrobromide, $Pd(OAc)_2$, $PPh_3$, $Cs_2CO_3$, 1,4-dioxane, 100° C., 82%; (e) 20% $N_2H_4$/EtOH, 105° C., 84%; (f) Styrene, $Pd(OAc)_2$, P(o-tolyl)$_3$, $NEt_3$, 100° C., 73-76%. DIPEA=N,N-diisopropylethylamine.

Stilbenes 1, 2, and 4a-b were tested for inhibition of biofilm formation in a wild-type *P. aeruginosa* strain (PAO1) at 500 μM using standard static biofilm growth assays.

Biofilms were grown in a modified M9 minimal media in 96-well microtiter plates, and crystal violet staining of the surface-associated biomass was used to quantify biofilm growth at 12 and 24 h (see The Examples). This preliminary screen and subsequent dose-response analyses revealed that 1 and 2 were able to inhibit biofilm growth at 24 h in *P. aeruginosa* by 56% and 48%, respectively, at 100 micro M. Neither indole, derivative (4a-b), however, showed appreciable anti-biofilm activity.

2-ABI-stilbene 1 was selected as the most promising lead compound, and attempts were made to identify potential structural motifs within 1 that were responsible for the observed anti-biofilm activity in order to further improve its inhibitory properties. Five simple sub-structures were identified (compounds 5-9, outlined in Scheme 3), and each of these compounds was tested in analogous *P. aeruginosa* biofilm assays. Removing the amino-group or 2-AI unit, affording 5 and 6, led to complete loss of inhibitory activity. However, removal of the styrene moiety (to yield 2-ABI 7) revealed a sub-structure that exhibited greater activity than lead compound 1, almost completely inhibiting biofilm formation at 24 h (94% inhibition, $IC_{50}$=47 microM). Structurally-related 2-thiobenzamidazole (2-TBI) derivatives were recently reported to display anti-biofilm activity in *P. aeruginosa*. However, 2-TBI and 5-OMe-2-TBI were significantly less active than 2-ABI derivatives in our biofilm assay. [29] It is interest to note that in PCT published application WO 2010/144686 [30] compound 7 is reported to exhibit no inhibition of biofilm formation in certain Gram-positive bacteria. The aryl component of 2-ABI (7) was essential for anti-biofilm activity, as neither 2-AI (8) nor guanidine (9) was found to display significant inhibitory activity in *P. aeruginosa*.

Scheme 3: Compounds studied (5-9) to dissect the structural features necessary for the activity of initial lead stilbene 1.

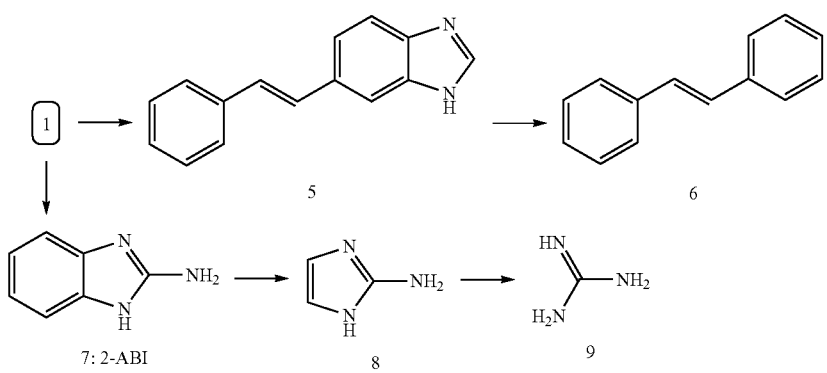

Continuing based on the activity of compound 7, a library of 2-ABI derivatives were synthesized to further probe the activity of this compound class in *P. aeruginosa*. Fifteen 2-ABIs (10-24) were readily generated in one-step via condensation of various functionalized o-diaminobenzenes with cyanogen bromide (Table 1). [31] The biofilm inhibitory activities of these compounds in *P. aeruginosa* was studied and 2-ABI derivatives capable of inhibiting biofilm growth were identified, including certain compounds which inhibited biofilm growth by ~90%, but with improved potencies (i.e., lower $IC_{50}$ values) relative to 7. An increase in potency was achieved, for example, either by halide (10-13) or methyl substitutions (19-21) on the 2-ABI aryl group. In turn, aryl-substitutions containing hydrogen bond donors or acceptors led to either a total loss (16) or significant reductions in biofilm inhibitory activity (Table 1). The most potent biofilm inhibitor identified overall was the 5,6-dimethyl 2-ABI (21, $IC_{50}$=4.0 microM), which was ~10-fold more active than the parent compound 7. Amongst the few biofilm inhibitors for which $IC_{50}$ data has been reported, [8, 10, 12, 14] 21 constitutes one of the most active *P. aeruginosa* biofilm inhibitors known. Dose-response curves and images of crystal violet-stained biofilms in the presence of 7 and 21 are shown in FIG. 1A.

TABLE 1

*P. aeruginosa* PAO1 biofilm inhibition data for 2-ABI derivatives.

| Compound | R | $IC_{50}$ ($\mu M$)[a] |
|---|---|---|
| 7 | H | 47 |
| 10 | 5-I | 20 |
| 11 | 5-Br | 22 |
| 12 | 5-Cl | 28 |
| 13 | 5-F | 35 |

TABLE 1-continued

*P. aeruginosa* PAO1 biofilm inhibition data for 2-ABI derivatives.

| Compound | R | $IC_{50}$ ($\mu M$)[a] |
|---|---|---|
| 14 | 5-COPh | ND |
| 15 | 5-CO$_2$Me | 140 |
| 16 | 5-CO$_2$H | ND |
| 17 | 5-CN | 180 |
| 18 | 5-NO$_2$ | 63 |
| 19 | 4-Me | 39 |
| 20 | 5-Me | 25 |
| 21 | 5,6-Me | 4.0 |
| 22 | 5-OMe | 80 |
| 23 | 5-NH$_2$ | ND |
| 24 | Fused 5,6-Ph[b] | 48 |

[a]$IC_{50}$ values were only obtained for 2-ABI derivatives exhibiting >60% biofilm inhibition after 24 h; ND = not determined. See The Examples for 95% confidence intervals for $IC_{50}$ values.
[b]Full name: 2-amino-1H-naphtho[2,3-d]imidazole.

Compounds capable of not only inhibiting biofilm growth, but also dispersing preformed biofilms, are of particular value for a range of clinical and other applications. The ability of compounds 7 and 21 to disperse 24 h-old *P. aeruginosa* biofilms was tested using the crystal violet staining assay (FIG. 1B). Biofilms were allowed to develop in the absence of compound for 24 h, after which non-biofilm material was removed by washing with buffer and fresh media with compound was added. Biofilm was quantified after an additional 24 h, and the amount of dispersed biofilm was determined via comparison of the amount of biofilm at 48 h in the presence of compound versus the amount of biofilm at 24 h in the absence of compound. 2-ABIs 7 and 21 were capable of strongly dispersing *P. aeruginosa* biofilms (~80%), with half maximal dispersion $DC_{50}$ values of 84 μM and 92 μM, respectively (FIG. 1B).

Little is known about the actual mechanisms of action of most small molecule biofilm inhibitors. As such, the mechanism by which the 2-ABI scaffold elicits its biofilm inhibitory and dispersive activity in *P. aeruginosa* was investigated. Planktonic growth curve analyses (under conditions identical to biofilm growth) demonstrated that the observed activities were not a result of a bactericidal mechanism. Melander and co-workers have reported that 2-ABI derivatives bearing 5-amido substituents inhibit and disperse biofilms through a zinc-dependent mechanism, albeit in Gram-positive as opposed to Gram-negative bacteria (see above). [22, 30] We screened a wide range of metals, including zinc, in a dose-dependent manner for mitigating effects on the biofilm inhibitory activity of 7 in *P. aeruginosa*, but observed no change in activity.

Figure 1D:
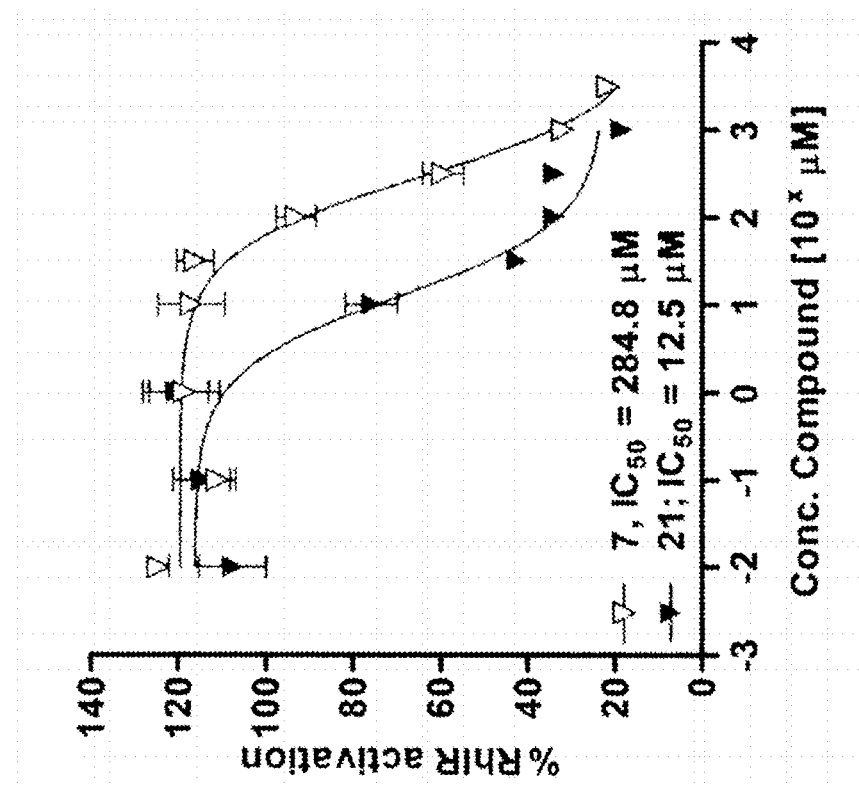
Figure 1C:
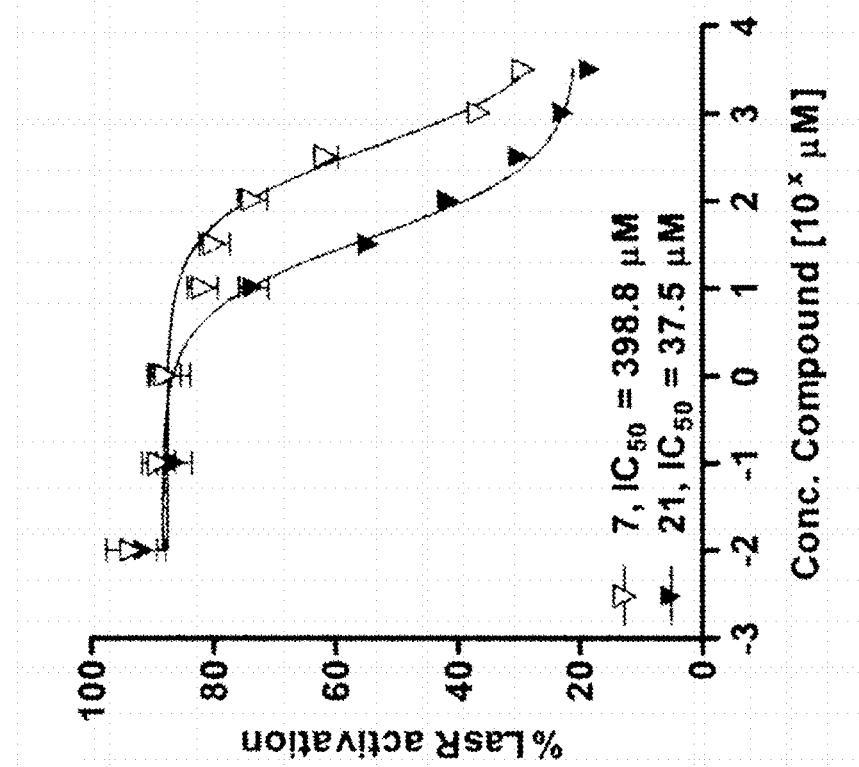

As introduced above, the role of QS in biofilm formation is well documented [6-8,15] and therefore the abilities of 7 and 21 to inhibit QS in *P. aeruginosa* were evaluated. For this purpose, two wild-type *P. aeruginosa* QS reporter strains were prepared that contain the plasmids plasI-LVAgfp and prhII-LVAgfp. (see: The Examples) These strains report the activity of two intracellular QS receptors in *P. aeruginosa* (LasR and RhlR) by the production of green fluorescent protein (gfp), allowing for LasR and RhlR activities, and thus QS levels, to be quantified by fluorescence. A significant reduction in both LasR and RhlR activities were observed in the presence of 7 and 21 at 1-10× their $IC_{50}$ values for biofilm inhibition (FIGS. 1C-D). Studies of related 2-ABI derivatives have shown that this class of molecules is bacterial cell permeable, allowing us to surmise that 7 and 21 could act on the Las and Rhl systems intracellularly. [32, 33] Further, we utilized a *P. aeruginosa* strain that constitutively-expresses genomic-gfp to demonstrate that 7 and 21 do not simply globally affect protein synthesis (see the Examples). The precise targets of 7 and 21 that result in QS disruption are not yet known. While not wishing to be bound by any particular theory, these findings suggest that biofilm modulation by 2-ABI derivatives is occurring, at least in part, through interference with the *P. aeruginosa* Las and Rhl QS circuits.

2-ABI derivatives are potent anti-biofilm agents in *P. aeruginosa*. Several of these 2-ABI derivatives are among the most active *P. aeruginosa* biofilm modulators to be reported. Moreover, these compounds are capable of both inhibiting the growth of and dispersing preformed biofilms. The present results are surprising in light of previous data on related 2-ABI derivatives that indicated they were inactive in *P. aeruginosa*, [22] and support the continued study of this structurally simple, chemically robust compound class in Gram-negative bacteria. Recently, 2-ABI derivative 18 was reported to be a biofilm inhibitor in Gram-positive bacteria. [34] The present studies further demonstrate that 2-ABIs, for example, compounds 7 and 21, are also capable of QS inhibition in *P. aeruginosa*, suggesting a possible mechanism for biofilm inhibition. A link between 2-ABI-type anti-biofilm agents and QS, to our knowledge, is previously undocumented.

Additional details related to this invention are reported by Frei et al. [64] and the supplemental materials available on-line related to this publication, all of which is incorporated by reference herein.

Gram-negative bacteria represent numerous relevant pathogens. Besides *P. aeruginosa*, other Gram-negative bacteria include: *Aeromonas hydrophila, A. salmonicida, Agrobacterium tumefaciens, Burkholderia cepacia, Chromobacterium violaceum, Enterobacter agglomeran, Erwinia carotovora, E. chrysanthemi, Escherichia coli, Nitrosomas europaea, Obesumbacterium proteus, Pantoea stewartii, Pseudomonas aureofaciens, P. syringae, Ralstonia solanacearum, Rhisobium etli, R. leguminosarum, Rhodobacter sphaeroides, Serratia liguefaciens, S. marcescens, Vibrio anguillarum, V. fischeri, V. cholerae, Xenorhabdus nematophilus, Yersinia enterocolitica, Y. pestis, Y. pseudotuberculosis, Y. medievalis*, and *Y. ruckeri*.

Unless defined otherwise, all technical and scientific terms used herein have the broadest meanings as commonly understood by one of ordinary skill in the art to which this invention pertains. In addition, hereinafter, the following definitions apply:

As defined herein, "contacting" means that a compound of the present invention is provided such that it is capable of making physical contact with another element, such as a microorganism, a microbial culture, a biofilm, or a substrate. In another embodiment, the term "contacting" means that a compound of the present invention is introduced into an individual receiving treatment, and the compound is allowed to come in contact in vivo. The term "administering" is also used for providing a compound or pharmaceutical composition to an individual in need of treatment. Various administration methods can be employed as will be appreciated by one of ordinary skill in the art.

In specific embodiments herein, contracting is achieved by release of one or more biofilm-inhibitory compounds of the invention (e.g., a compound of formulas I, IA1, IA2 or IB herein) from a polymer film, multilayer film, hydrogel, or coating that contains the one or more biofilm-inhibitory compounds of the invention. In general, any art-known type of film, hydrogel or coating can be employed for containing and thereafter releasing one or more biofilm-inhibitory compounds of the invention. It will be appreciated that the film or coating (e.g., polymer) must be chemically compatible with and not inactivate the biofilm-inhibitory compound. In other specific embodiments, contacting is achieved by encapsulation of and later release of one or more biofilm-inhibitory compounds of the invention into the environment to be. Encapsulation can be by any art known method and can be in the form of micro- or nanoencapsulation.

Alkyl groups include straight-chain, branched and cyclic alkyl groups. Alkyl groups include those having from 1 to 20 carbon atoms. Alkyl groups include small alkyl groups having 1 to 3 carbon atoms. Alkyl groups include medium size alkyl groups having from 4-7 carbon atoms. Alkyl groups include larger alkyl groups having 8 or more carbon atoms. Cyclic alkyl groups include those having one or more rings. Cyclic alkyl groups include those which have 1, 2 or 3 rings. Cyclic alkyl groups also include those having 3-10 carbon atoms. Cyclic alkyl groups include those having a 3-, 4-, 5-, 6-, 7-, 8-, 9- or 10-member carbon ring and particularly those having a 3-, 4-, 5-, 6-, 7-, or 8-member ring. The carbon rings in cyclic alkyl groups can also carry straight-chain or branched alkyl group substituents. Cyclic alkyl groups can include bicyclic and tricyclic alkyl groups. Alkyl groups are optionally substituted with one or more non-hydrogen substituents as described herein. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, cyclohexyl, decalinyl, and norbornyl all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl. Such groups are optionally substituted as described herein above.

An alicyclic group is a group having one or more saturated or unsaturated carbon rings and optionally contains one to three heteroatoms (e.g., N, O or S) per ring. Alicyclic groups, for example, contain one or two double bonds. To satisfy valence requirement, a ring atom may be substituted as described herein. One or more carbons in an alicyclic ring can be —CO— groups. Alicyclic groups include those having 3-12 carbon atoms, 1-6, heteroatoms, and optionally replacing 1 or 2 carbon atoms with a —CO— group and optionally having 1, 2 or 3 double bonds. Alicyclic groups include those having 3-12 or 3-10 ring atoms of which up to three can be heteroatoms other than carbon. Alicyclic groups can contain one or more rings each of which is saturated or unsaturated. Alicyclic groups include bicyclic and tricyclic groups. Preferred alicyclic groups have 5- or 6-member rings. Alicyclic groups are optionally substituted as described herein. Specifically, alicyclic groups can be substituted with one or more alkyl groups. Carbocyclic groups are alicyclic groups as described above in which all the ring atoms are carbon (this group includes among others cycloalkyl and cycloalkenyl groups). Heterocyclic groups are alicyclic groups as described above that contain at least one heteroatom (non-carbon atom), specific heteroatoms are N, O or S.

Carbocyclic groups include among others cycloalkyl groups, cycloalkenyl groups, cyclopropyl, cyclobutyl, cyclopentyl groups, cyclopentadienyl groups, cyclohexyl, and cyclohexenyl. Heterocyclic groups include those having 5-12 ring atoms, with 1, 2 or 3 heteroatoms and 1, 2 or 3 double bonds. Heterocyclic groups include those having 5- and 6-member rings with one or two nitrogens and one or two double bonds. Heterocyclic groups include those having 5- and 6-member rings with an oxygen or a sulfur and one or two double bonds. Heterocyclic grouse include those having 5- or 6-member rings and two different heteroatom, e.g., N and O, O and S or N and S. Specific heterocyclic groups include among others among others, pyrrolidinyl, piperidyl, piperazinyl, pyrrolyl, pyrrolinyl, furyl, thienyl, morpholinyl, oxazolyl, oxazolinyl, oxazolidinyl, indolyl, triazoly, and triazinyl groups.

In embodiments herein alicyclic rings can be formed between certain substitution sites on the molecules of formula I. Such alicyclic rings include the atom(s) of or between the sites of substitution and are defined with respect to the optional presence of heteroatoms, the optional presence of —CO— moieties and the optional presence of double bonds as are alicylic groups. In embodiments herein heterocyclic rings can be formed between certain substitution sites on the molecules of formula I. Such heterocyclic rings include the atom(s) of or between the sites of substitution and are defined with respect to the number and type of heteroatoms, the optional presence of —CO— moieties and the optional presence of double bonds as are heterocyclic groups Aryl groups include groups having one or more 5- or 6-member aromatic rings. Aryl groups can contain one, two or three, 6-member aromatic rings. Aryl groups can contain two or more fused aromatic rings. Aryl groups can contain two or three fused aromatic rings. Aryl groups are optionally substituted with one or more non-hydrogen substituents. Substituted aryl groups include among others those which are substituted with alkyl or alkenyl groups, which groups in turn can be optionally substituted. Specific aryl groups include phenyl groups, biphenyl groups, pyridinyl groups, and naphthyl groups, all of which are optionally substituted as described herein. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms.

Heteroaryl groups include groups having one or more aromatic rings in which at least one ring contains a heteroatom (a non-carbon ring atom). Heteroaryl groups include those having one or two heteroaromatic rings carrying 1, 2 or 3 heteroatoms and optionally have one 6-member aromatic ring. Heteroaryl groups can contain 5-20, 5-12 or 5-10 ring atoms. Heteroaryl groups include those having one aromatic ring contains a heteroatom and one aromatic ring containing carbon ring atoms. Heteroaryl groups include those having one or more 5- or 6-member aromatic heteroaromatic rings and one or more 6-member carbon aromatic rings. Heteroaromatic rings can include one or more N, O, or S atoms in the ring. Heteroaromatic rings can include those with one, two or three N, those with one or two O, and those with one or two S, or combinations of one or two or three N, O or S. Specific heteroaryl groups include pyridinyl, pyrazinyl, pyrimidinyl, quinolinyl, and purinyl groups.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups.

Heteroarylalkyl groups are alkyl groups substituted with one or more heteroaryl groups wherein the alkyl groups optionally carry additional substituents and the aryl groups are optionally substituted.

Alkylaryl groups are aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl having one or more hydrogens replaced with one or more fluorine atoms, chlorine atoms, bromine atoms and/or iodine atoms.

Alkylheteroaryl groups are aryl groups substituted with one or more alkyl groups wherein the alkyl groups optionally carry additional substituents and the aryl groups are optionally substituted.

An alkoxy group is an alkyl group (including cycloalkyl), as broadly discussed above, linked to oxygen. An aryloxy group is an aryl group, as discussed above, linked to an oxygen. A heteroaryl group is a heteroaryl group as discussed above linked to an oxygen.

An acyl group is an R'—CO group where R' in general is an alkyl, aryl, or heteroaryl group as described above. An acetyl group is a $CH_3$—CO— group.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

As to any of the above groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

The term "effective amount" is used generically herein to refer to the amount of a given compound or in case of a mixture the combined amount of mixture components that provides a measurable effect for a listed function. For example, in certain aspects of the invention, a compound of the invention is contacted with an element in order to disrupt a biofilm and in this case, the effective amount or combined effective amount of the compound or compounds is that amount that shows a measurable disruption of a biofilm. The effective amount will vary dependent upon the stated function, the environment or element being contacted, the organism forming the biofilm or which is to be contacted, the state of development of the biofilm, among other conditions of the use of the compound. It will be understood by one of ordinary skill in the art, that for a given application, the effective amount can be determined by application of routine experimentation and without undue experimentation by methods that are described herein or that are known in the art.

The term "therapeutically effective amount" is used generically herein to refer to the amount of a given compound or in case of a mixture the combined amount of mixture components when administered to the individual (including a human, or non-human animal) that provides a measurable therapeutic effect for a listed disease, disorder or condition to at least partially ameliorate a symptom of such disease, disorder or condition. The present invention provides methods of treating disorders, diseases conditions and symptoms in a human or non-human animal and particularly in a human, by administering to an individual in need of treatment or prophylaxis, a therapeutically effective amount of one or more compounds of this invention to the individual in need thereof. The result of treatment can be partially or completely alleviating, inhibiting, preventing, ameliorating and/or relieving the disorder, condition or one or more symptoms thereof. As is understood in the art, the therapeutically effective amount of a given compound will depend at least in part upon, the mode of administration, any carrier or vehicle (e.g., solution, emulsion, etc.) employed, the extent of damage and the specific individual (human or non-human) to whom the compound is to be administered (age, weight, condition, sex, etc.). The dosage requirements needed to achieve the "therapeutically effective amount" vary with the particular compositions employed, the route of administration, the severity of the symptoms presented and the particular individual being treated. Based on the results obtained in standard pharmacological test procedures, projected daily dosages of active compound can be determined as is understood in the art.

Administration is intended to encompass administration of a compound, pharmaceutically acceptable salt, solvate or ester thereof alone or in a pharmaceutically acceptable carrier thereof or administration of a prodrug derivative or analog of a compound of this invention which will form an equivalent amount of the active compound or substance within the body. An individual in need of treatment or prophylaxis includes those who have been diagnosed to have a given disorder or condition and to those who are suspected, for example, as a consequence of the display of certain symptoms, of having such disorders or conditions.

Compounds of this invention can be employed in unit dosage form, e.g. as tablets or capsules. In such form, the active compound or more typically a pharmaceutical composition containing the active compound is sub-divided in unit dose containing appropriate quantities of the active compound; the unit dosage forms can be packaged compositions, for example, packaged powders, vials, ampules, pre-filled syringes or sachets containing liquids. The unit dosage form can be, for example, a capsule or tablet itself, or it can be the appropriate number of any such compositions in package form.

The dosage can vary within wide limits and as is understood in the art will have to be adjusted to the individual requirements in each particular case. By way of general guidance, the daily oral dosage can vary from about 0.01 mg to 1000 mg, 0.1 mg to 100 mg, or 10 mg to 500 mg per day of a compound of formulas herein or of the corresponding amount of a pharmaceutically acceptable salt thereof. The daily dose may be administered as single dose or in divided doses and, in addition, the upper limit can also be exceeded when this is found to be indicated.

Any suitable form of administration can be employed in the method herein. The compounds of this invention can, for example, be administered in oral dosage forms including tablets, capsules, pills, powders, granules, elixirs, tinctures, suspensions, syrups and emulsions. Oral dosage forms may include sustained release or timed release formulations. The compounds of this invention may also be administered topically, intravenously, intraperitoneally, subcutaneously, or intramuscularly, all using dosage forms well known to those of ordinary skill in the pharmaceutical arts. Topical application can include those in which the biofilm-inhibitory compound is formulated in a hydrogel or encapsulated in microspheres or nanospheres, for example.

Compounds of this invention can also be administered in intranasal form by topical use of suitable intranasal vehicles. For intranasal or intrabronchial inhalation or insulation, the compounds of this invention may be formulated into an aqueous or partially aqueous solution, which can then be utilized in the form of an aerosol. Administration includes any form of administration that is known in the art and is intended to encompass administration in any appropriate dosage form and further is intended to encompass administration of a compound, alone or in a pharmaceutically acceptable carrier. Pharmaceutical carriers are selected as is known in the art based on the chosen route of administration and standard pharmaceutical practice.

The compounds of this invention can also be administered to the eye, preferably as a topical ophthalmic formulation. The compounds of this invention can also be combined with a preservative and an appropriate vehicle such as mineral oil or liquid lanolin to provide an ophthalmic ointment. The compounds of this invention may be administered rectally or vaginally in the form of a conventional suppository. The compounds of this invention may also be administered transdermally through the use of a transdermal patch containing the active compound and a carrier that is inert to the active compound, is non-toxic to the skin, and allows delivery of the agent for systemic absorption into the blood stream via the skin.

The compounds of the invention may be administered employing an occlusive device. A variety of occlusive devices can be used to release an ingredient into the blood stream such as a semipermeable membrane covering a reservoir containing the active ingredient with or without a carrier, or a matrix containing the active ingredient. Other occlusive devices are known in the literature.

Pharmaceutical compositions and medicaments of this invention comprise one or more compounds in combination with a pharmaceutically acceptable carrier, excipient, or diluent. Such compositions and medicaments are prepared in accordance with acceptable pharmaceutical procedures, such as, for example, those described in Remington's Pharmaceutical Sciences, 17th edition, ed. Alfonoso R. Gennaro, Mack Publishing Company, Easton, Pa. (1985), which is incorporated herein by reference in its entirety. The invention also encompasses method for making a medicament employing one or more compounds of this invention which exhibit a therapeutic effect.

Pharmaceutically acceptable carriers are those carriers that are compatible with the other ingredients in the formulation and are biologically acceptable. Carriers can be solid or liquid. Solid carriers can include one or more substances that can also act as flavoring agents, lubricants, solubilizers, suspending agents, fillers, glidants, compression aids, binders, tablet-disintegrating agents, or encapsulating materials. Liquid carriers can be used in preparing solutions, suspensions, emulsions, syrups and elixirs. The active ingredient can be dissolved or suspended in a pharmaceutically acceptable liquid carrier such as water (of appropriate purity, e.g., pyrogen-free, sterile, etc.), an organic solvent, a mixture of both, or a pharmaceutically acceptable oil or fat. The liquid carrier can contain other suitable pharmaceutical additives such as, for example, solubilizers, emulsifiers, buffers, preservatives, sweeteners, flavoring agents, suspending agents, thickening agents, colors, viscosity regulators, stabilizers or osmo-regulators. Compositions for oral administration can be in either liquid or solid form.

Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins. Suitable examples of liquid carriers for oral and parenteral administration include water of appropriate purity, aqueous solutions (particularly containing additives, e.g. cellulose derivatives, sodium carboxymethyl cellulose solution), alcohols (including monohydric alcohols and polyhydric alcohols e.g. glycols) and their derivatives, and oils. For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant. Liquid pharmaceutical compositions that are sterile solutions or suspensions can be administered by, for example, intramuscular, intraperitoneal or subcutaneous injection. Sterile solutions can also be administered intravenously. Compositions for oral administration can be in either liquid or solid form. The carrier can also be in the form of creams and ointments, pastes, and gels. The creams and ointments can be viscous liquid or semisolid emulsions of either the oil-in-water or water-in-oil type. Pastes comprised of absorptive powders dispersed in petroleum or hydrophilic petroleum containing the active ingredient can also be suitable.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like.

In addition these salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. Compounds of formula I can also be present in the form of zwitterions.

Compounds of the invention can be in the form of salts which in specific embodiments are non-toxic and more specifically pharmaceutically-acceptable. Pharmaceutically acceptable salts comprise pharmaceutically-acceptable anions and/or cations. Pharmaceutically-acceptable cations include among others, alkali metal cations (e.g., $Li^+$, $Na^+$, $K^+$), alkaline earth metal cations (e.g., $Ca^{2+}$, $Mg^{2+}$), non-toxic heavy metal cations and ammonium ($NH_4^+$) and substituted ammonium ($N(R')_4^+$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include among other halides (e.g., $Cl^-$, Bo, sulfate, acetates (e.g., acetate, trifluoroacetate), ascorbates, aspartates, benzoates, citrates, and lactate.

Compounds of the invention can have prodrug forms. Prodrugs of the compounds of the invention are useful in the methods of this invention. Any compound that will be converted in vivo to provide a biologically, pharmaceutically or therapeutically active form of a compound of the invention is a prodrug. Various examples and forms of prodrugs are well known in the art. Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392).

The invention expressly includes pharmaceutically usable solvates of compounds according to formulas herein. The compounds of formula I can be solvated, e.g. hydrated. The solvation can occur in the course of the manufacturing process or can take place, e.g. as a consequence of hygroscopic properties of an initially anhydrous compound of formulas herein (hydration).

Well-known methods for assessment of drugability can be used to further assess active compounds of the invention for application to given therapeutic application. The term "drugability" relates to pharmaceutical properties of a prospective drug for administration, distribution, metabolism and excretion. Drugability is assessed in various ways in the art. For example, the "Lipinski Rule of 5" for determining drug-like characteristics in a molecule related to in vivo absorption and permeability can be applied (C. A. Lipinski, F. Lombardo, B. W. Dominy, P. J. Feeney, *Experimental and computational approaches to estimate solubility and permeability in drug discovery and development settings*, Adv. Drug Del. Rev., 2001, 46, 3-26 and Arup K. Ghose, Vellarkad N. Viswanadhan, and John J. Wendoloski, A *Knowledge-Based Approach in Designing Combinatorial or Medicinal Chemistry Libraries for Drug Discovery*, J. Combin. Chem., 1999, 1, 55-68.) In general a preferred drug for oral administration exhibits no more than one violation of the following rules:
(1) Not more than 5 hydrogen bond donors (e.g., nitrogen or oxygen atoms with one or more hydrogens);
(2) Not more than 10 hydrogen bond acceptors (e.g., nitrogen or oxygen atoms);
(3) Molecular weight under 500 g/mol and more preferably between 160 and 480; and
(4) log P less than 5 and more preferably between −0.4 to +5.6 and yet more preferably −1<log P<2.

Compounds of this invention preferred for therapeutic application include those that do not violate one or more of 1-4 above.

Compounds of this invention preferred for therapeutic application include those having log P less than 5 and more preferably between −0.4 to +5.6 and yet more preferably −1<log P<2.

The compounds of this invention may contain one or more chiral centers. Accordingly, this invention is intended to include racemic mixtures, diastereomers, enantiomers and mixture enriched in one or more stereoisomer. The scope of the invention as described and claimed encompasses the racemic forms of the compounds as well as the individual enantiomers and non-racemic mixtures thereof.

Before the present methods are described, it is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein.

As used herein, the term "treating" includes preventative as well as disorder remittent treatment. As used herein, the terms "reducing", "suppressing" and "inhibiting" have their commonly understood meaning of lessening or decreasing.

In certain embodiments, the present invention encompasses administering the compounds useful in the present invention to a patient or individual. A "patient" or "individual", used equivalently herein, refers to an animal. In particular, an animal refers to a mammal, preferably a human. The patient either: (1) has (is diagnosed to have or is believed to have) a condition remediable or treatable by administration of a compound of the invention; or (2) is susceptible to a condition that is preventable by administering a compound of this invention.

Additional embodiments of the invention include the following.

In an embodiment, the present invention provides a surface coating or polymer having incorporated therein a compound of the present invention. The amount of compound or polymer in the surface coating is that sufficient to provide antifouling effect. In an embodiment, the compounds of the present invention are useful as an antifouling agent. In specific embodiments, the compounds of this invention exhibit no substantial antimicrobial effect. Compounds of the present invention are further useful in a medical, scientific, and/or biological application.

In one aspect, the present invention provides a composition comprising one or more compounds of the present invention and a carrier or diluent. In a preferred embodiment, the carrier or diluent comprises a liquid. Such a liquid may comprises an aqueous solvent or a non-aqueous solvent. An exemplary solvent comprises one or more organic solvents. The carrier or diluent may also comprise an ionic liquid. In an embodiment of this aspect, the composition comprises an organic or inorganic polymeric substance. The polymeric substance may comprise one or more compounds of the present invention, admixed with a polymer, bound to a polymer, or adsorbed on to a polymer. In an exemplary embodiment of this aspect, the composition is in the form of a solution or suspension of said at least one compounds of the present invention, preferably in an aerosol or powder formulation.

In an embodiment of this aspect, the composition is formulated as a disinfectant or cleaning formulation. In another embodiment, the composition is in the form of a powder, a solution, a suspension, a dispersion, an emulsion, or a gel. In an exemplary embodiment, the composition is in the form of a pharmaceutical composition comprising a pharmaceutically acceptable carrier, diluent, and/or excipient and one or more compounds of the present invention. The composition may be in a form suitable for parenteral or non-parenteral administration. A preferred composition may be formulated for topical, intradermal, intramuscular, intraperitoneal, intravenous, subcutaneous, intranasal, epidural, ophthalmic, or oral administration. In an embodiment of this aspect the composition is formulated for administration by infusion or bolus injection, absorption through epithelial or mucocutaneous linings and may be administered together with other biologically active agents. In an embodiment, the composition may further be formulated for use in an inhaler or nebulizer.

In another aspect, the present invention provides a method of treating an infection in a human or animal, the method comprising administration to the individual (human or animal) of a therapeutically effective amount of one or more compounds of the present invention. In an embodiment, the treatment is therapeutic or prophylactic.

In a related embodiment, the present invention provides a method of treating an infection or condition in an individual that is characterized by biofilm formation, the method comprising administering one or more compounds of the present invention. In an embodiment, the condition is cystic fibrosis. In an embodiment, the condition is dental caries, periodontitis, otitis media, muscular skeletal infections, necrotizing fasciitis, biliary tract infection, osteomyelitis, bacterial prostatitis, native valve endocarditis, cystic fibrosis pneumonia, or meloidosis. In an embodiment, the condition is a nosocomial infection; preferably the infection is ICU pneumonia or an infection associated with sutures, exit sites, arteriovenous sites, scleral buckles, contact lenses, urinary catheter cystitis, peritoneal dialysis (CAPD) peritonitis, IUDs, endotracheal tubes, Hickman catheters, central venous catheters, mechanical heart valves, vascular grafts, biliary stent blockage, orthopedic devices, or penile prostheses. In an embodiment, the infection is a skin infection, a burn infection, or a wound infection. According to this aspect, the individual may preferably be an immune-compromised individual.

The present invention further provides a method for treating or preventing biofilm formation on a surface, the method comprising contacting said surface with one or more compounds in an amount effective for affecting biofilm formation of the present invention. In an embodiment, the surface is a non-biological surface. In an embodiment, the surface is a natural surface. In an embodiment, the surface is a surface of a plant, seed, wood, fiber or hair. In an embodiment, the surface is a biological surface; preferably the surface is a surface of a tissue, membrane, or skin. In an embodiment, the surface is a hard surface; preferably the surface comprises a metal, an organic polymer, an inorganic polymer, a natural elastomer, a synthetic elastomer, glass, wood, paper, concrete, rock, marble, gypsum, or ceramic. In an embodiment, the said surface is coated or wherein the surface is a coating; in a preferred embodiment, the coating comprises enamel, varnish, or paint.

In an embodiment of this aspect, the surface is a soft surface, and may be the surface of a fiber comprising a yarn, a textile, a vegetable fiber, or rock wool. In another embodiment, the surface is a porous surface. In an embodiment, the surface is a surface of process equipment or components of cooling equipment. In a preferred embodiment, the process equipment is or is a component of a cooling tower, a water treatment plant, a dairy processing plant, a food processing plant, a chemical process plant, or a pharmaceutical process plant. In a preferred embodiment the surface is that of a filter or a membrane filter.

In an embodiment of this aspect, the surface is a surface of a toilet bowl, a bathtub, a drain, a high-chair, a counter top, a vegetable, a meat processing room, a butcher shop, food preparation areas, an air duct, an air-conditioner, a carpet, paper or woven product treatment, a diaper, personal hygiene products and a washing machine. In another embodiment, the surface is an industrial surface or a medical surface; preferably the surface is a surface in a hospital, a veterinary hospital, a mortuary, or a funeral parlor.

In another aspect, the compounds of the present invention are useful as a component of a dentifrice, a mouthwash, or a composition for the treatment of dental caries; for treatment of acne; or for cleaning and/or disinfecting contact lenses. The compounds of the present invention are further useful for incorporation into the surface of a medical device or an implant device. Preferably the implant device is an artificial heart valve, hip joint, an indwelling catheter, pacemaker, or surgical pin. The compounds of the present invention are further useful as an antifouling coating. The present invention further provides an optical lens, wherein at least a part of a surface of the lens is associated with one or more compounds of the present invention. Preferably, the optical lens is a contact lens.

In another aspect, the present invention provides a biofilm removing or inhibiting composition comprising one or more compounds of the present invention in an amount effective for removing or inhibiting biofilm formation and a vehicle or carrier, wherein the amount of the mixture is effective to remove or disrupt a bacterial biofilm or inhibit normal biofilm formation. An embodiment of this aspect may further comprise a surfactant selected from the group consisting of an anionic surfactant, a nonionic surfactant, an amphoteric surfactant, a biological surfactant, and any combination of these; or a compound selected from the group consisting of a biocide, a fungicide, an antibiotic, and any combination of these.

The term antibacterial agent refers generically to chemical species that exhibit bacteriostatic or bactericidal effect. Of particular interest are antibacterial agents effective against one or more Gram-negative bacteria and particularly those that are effective against *Pseudomonas*, and more particularly against *P. aeruginosa*. Antibacterial agents include disinfectants such as chlorine, bromine and chlorine dioxide and quaternary ammonium compounds as well as antibiotics. A variety of antibiotics are known in the art and one of ordinary skill in the art can select one or more antibiotics appropriate for use against a given species or strain of Gram-negative bacteria. Antibiotics useful in the method of this invention include among others gentamicin, kanamycin neomycin, streptomycin and other aminoglycoside antibiotics which are of particular use against *P. aeruginosa* infections.

Additional exemplary classes of antibiotics include among others Penicillins, Cephalosporins, Carbapenems, Tetracyclines, Macrolides, Quinolones and Sulfonamides. One of ordinary skill in the art can readily chose amongst known antibiotics of these classes for use in the methods herein.

In another embodiment, the invention provides a film, multilayer film, hydrogel or coating, for application to a surface or in the vicinity of a surface, to inhibit or prevent biofilm formation on the surface.

In another embodiment, the invention provides a coating for application to a surface to regulate a symbiotic behavior other than biofilm formation of quorum sensing bacteria. Other symbiotic behaviors that may be regulated include swarming, motility, sporulation, conjugation, bioluminescence and/or production of pigments, antibiotics and enzymes. Quorum sensing molecules of the formulas of this invention may in one embodiment stimulate, initiate or enhance a symbiotic behavior (other than biofilm formation) of quorum sensing bacteria, particularly Gram-negative quorum sensing bacteria, particularly *Pseudomonas* and more particularly *P. aeruginosa*. Compounds of the formulas of this invention may in another embodiment inhibit, decrease or attenuate a symbiotic behavior (other than biofilm formation) of quorum sensing bacteria, particularly Gram-negative quorum sensing bacteria, particularly *Pseudomonas* and more particularly *P. aeruginosa*.

The coating can be applied to a variety of surfaces using methods that are well-known in the art. The coating may be in the form of a film, including a multi-layer film, or a gel, particularly a hydrogel, comprising one or more of the compounds of this invention. Coatings can be employed in medical and non-medical applications. Specific applications include coated medical devices (e.g., stents, catheters, and feminine hygiene products) and industrial coatings (e.g., ship hulls and heat exchangers). The coating may be applied to the surfaces of interest using a variety of known methods. In specific embodiments, the coating loaded with one or more biofilm inhibitory compounds of this invention is formed by solvent casting. In other embodiments, the loaded coating is formed by spin coating. In other embodiments, the loaded coating is formed by dip coating. In other embodiments, one or more of solvent casting, spin coating or dip coating is employed to form surfaces carrying biofilm inhibitory loaded films of this invention.

In an embodiment, biofilm inhibitory compounds of the invention can be encapsulated in thin bulk films of conventional polymers, such as PLA, or PLGA by known methods such as dip-coating or solvent casting. Such films can be applied to surfaces as desired where the encapsulated biofilm inhibitor is released to inhibit or prevent biofilm formation on the surface. In an embodiment, biofilm inhibitors of this invention can be loaded into nanostructured polymer multilayers, for example, PEMs and other cross-linked multilayers, for example, using a layer-by-layer approach. Multilayers can be applied to or formed on surfaces to release biofilm inhibitor to inhibit or prevent biofilm formation on the surface. Sustained release of the inhibitors can be obtained using such methods. Methods useful for making films or coatings including multilayer films are described, for example, in Lynn and co-workers: Adv. Mater. 2007; Biomacromolecules 2009; Adv. Mater. 2010; Langmuir 2010; ACS App. Mater. Inter. 2010; Langmuir 2010; Chem. Mater. 2010; J. Mater. Chem. 2011; Adv. Biomat. 2011; Biomacromolecules 2011 and in U.S. Pat. Nos. 7,883,720; 8,071,210 and published US applications US20080286345 and US20090105375, each of which is incorporated by reference herein for descriptions of methods and materials, particularly polymers and co-polymers, useful for forming films, multilayer films and the like.

In specific embodiments, the invention provides films, coatings or hydrogels containing one or more biofilm-inhibitory compounds. In specific embodiments, films, coatings and/or hydrogels or the like of this invention provide a concentration of a biofilm-inhibitory compound into the environment to be protected (e.g., a surface) that is effective for inhibiting formation of a biofilm or dispersing an already formed biofilm. In specific embodiments, films, coatings and/or hydrogels or the like of this invention provide a concentration of a biofilm-inhibitory compound into the environment to be protected that ranges from the $IC_{50}$ of the biofilm-inhibitory compound (which can be measured by methods as described herein) to the level of the compound that is cytotoxic to mammalian cells (which can be measured by methods as described herein). In specific embodiments, films, coatings and/or hydrogels or the like of this invention provide a concentration of a biofilm-inhibitory compound into the environment to be protected that ranges from the $IC_{50}$ of the biofilm-inhibitory compound (which can be measured by methods as described herein) to 0.250 mM. In more specific embodiments, the concentration of biofilm-inhibitory compound provided to the environment to be protected ranges from 4 microM to 200 microM. In yet more specific embodiment, the concentration ranges from 2-10 time the $IC_{50}$ of the biofilm-inhibitory compound to 200 microM. In additional embodiments, the concentration ranges from 10-200 microM, 10-100 microM, 20-100 microM, 40-200 microM, or 40 to 100 microM.

In specific embodiments, the loading of the film, coating or hydrogel with the biofilm-inhibitory compound ranges from 0.001 to 1 mg of compound/gram of polymer in the film, coating or hydrogel. In more specific embodiments, the loading of the film, coating or hydrogel with the biofilm-inhibitory compound ranges from 0.005 to 1 mg, 0.01 to 1 mg, 0.05 to 1 mg, 0.1 to 1 mg, 0.5 to 1 mg, 0.01 to 0.5 mg of compound/gram of polymer in the film, coating or hydrogel.

Biofilm formation on a surface or in the vicinity of a surface is inhibited by controlled release of the one or more biofilm-inhibitory compounds of the invention from a film formed on the surface to be protected or on a surface in the vicinity of the surface to be protected. Similar release can be used to disperse already-formed biofilms. Release from the film provides for spatially localized release at or near the surface to be protected or cleaned of biofilm enhancing the effectiveness of biofilm-inhibition. The rate of release can be controlled by changing the composition of film, coating or hydrogel as is known in the art. The release profile from the film can also be affected by varying the thickness of the films and the concentration of the one or more biofilm-inhibitory compounds in the film. The concentration of biofilm-inhibitory compounds in the film can be generally uniform throughout the film or the concentration may be non-uniform in the film.

The film, coating or hydrogel may be formed on the surface of a selected substrate by any known method. For example, the film may be formed by contacting of the surface with a solution of the polymer and active ingredient (e.g., one or more biofilm-inhibitory compounds), allowing a film to form on the surface and repeating the contacting step until a film of desired thickness is formed. The concentration of active ingredient(s) can be the same or different in the contacting steps. For example, the solution in one or more steps may contain polymer, but no active ingredient.

The films of this invention may also be formed by dip-coating, spin coating, or solvent casting using methods known in the art.

In specific embodiments, the invention provides (lactic-co-glycolic acid) films containing one or more biofilm-inhibitory compounds of this invention. The rate of release can be controlled by changing the composition of the polymers employed in the film, particularly by changing the lactide:glycolide ratio of the polymers.

In specific embodiments of either aspect of the invention, the lactide:glycolide ratio in the poly(lactic-co-glycolic acid) polymer used to prepare the film can range most generally from 1:99 to 99:1. In additional embodiments, the lactide:glycolide ratio in the poly(lactic-co-glycolic acid) polymers can range from 95:5 to 5:95 or from 75:25 to 25:75. In other embodiments, this ratio ranges from 40:60 to 85:15. In further embodiments, this ratio ranges from 50:50 to 75:25. In a further specific embodiment, this ratio ranges from 45:50 to 50:45. The films may be formed from a combination of poly(lactic-co-glycolic acid) polymers having different lactide:glycolide ratios. The molecular weight of the polymers employed is not particularly limited. In specific embodiments, the poly(lactic-co-glycolic acid) polymers can range in molecular weight from about 10,000 to 200,000. The end groups of poly(lactic-co-glycolic acid) polymers employed in this invention can be varied as is known in the art. For example, polymers with acidic end groups may be employed or polymers with hydroxyl-functionalized end groups may be employed. Alternatively, polymers with ester-functionalized end groups may be employed.

When prepared by dip-coating methods, PLGA films of this invention can generally be prepared by sequential dipping cycles ranging from 1 to several thousand iterations dependent upon the application. More specifically, the number of dipping cycles can range from 1-1000, from 1-100, from 5-100, or from 5-20. The concentration of inhibitor or activator in the polymer solutions depends upon the concentration that is desired to be released, and is application dependent.

Biofilm inhibitory coatings or films of this invention may be uniform polymer coatings or films that cover the entire surface of an object to be protected. Alternatively, as demonstrated herein, protection can be obtained of a surface by use of strategically-placed deposits of loaded film, by the application of partial or non-uniform coatings, and the use of removable inserts that disseminate the biofilm inhibitory compound more broadly and exert inhibitory effects over larger area. Such applications are particularly useful in cases where the design, function, scale, or surface properties of a device or object prohibit the direct application of uniform polymer coatings.

In additional embodiments, biofilm-inhibitory compounds of the invention can be provided in encapsulated form, such as in polymer-based microspheres or nan-spheres which are formed by methods that are well-known in the art, for example by solvent-evaporation-based methods.

Films, multilayer films and coating of this invention can be formed from degradable or non-degradable polymers and co-polymers. In a specific embodiment, polymers or co-polymers employed can be selectively degradable by a change in environment, such as a change in temperature or a change in pH. Degradable polymers include for example, polyester- and polyanhydride-based polymers and copolymers. Examples of useful polyesters include, among others, PLA, PLGA, polycaprolactones. Examples of useful polyanhydrides include, among others, polymers or copolymers of polysebacic acid. Films, multilayer films and coating of this invention can be formed from mixtures or blends of polymers or co-polymers. non-degradable polymers and co-polymers In specific embodiments, release of the one or more biofilm-inhibitory compounds of the invention or composition containing them is promoted by the degradation of the polymer matrix, diffusion of the molecule from the matrix, or a combination of both.

In a specific embodiment, covalently-crosslinked multilayers based on layer-by-layer assembly of azlactone-containing polymers as described in U.S. Pat. No. 8,071,210 can be employed in the methods of this invention to release one or more biofilm-inhibitory compounds of the invention. This patent is incorporated by reference herein in its entirety for descriptions and lists of polymers, co-polymers and other materials for forming covalently cross-linked multilayers useful in this invention as well as for method for making such multilayers and incorporating active ingredients such as the compounds of this invention therein.

In other specific embodiments, polyelectrolyte multilayers such as those described in U.S. Pat. No. 7,883,720 and U.S. published application 2009/0105375 can be employed in the methods of this invention to release one or more biofilm-inhibitory compounds of the invention. Each of these patent documents is incorporated by reference herein in its entirety for descriptions and lists of polymers, co-polymers and other materials for forming polyelectrolyte multilayers useful in this invention as well as for method for making such multilayers and incorporating active ingredients such as the compounds of this invention therein. Polyelectrolyte multilayers typically include two or more bilayers wherein each bilayer comprises a cationic or anionic polymer and an anion and a cation, respectively.

In additional embodiments, the biofilm-inhibitory compounds of the invention be provided in bulk objects and optionally released from such objects. Bulk objects include disks, slabs and other substrates and other structural elements that can be implanted, incorporated or used in other ways in biomedical or non-biomedical application. For example, one or more of biofilm-inhibitory compounds of the invention can be incorporated into such objects, e.g., by absorption. In a specific embodiment, one or more biofilm-inhibitory compounds of the invention can be introduced into porous matrix of an object to provide for biofilm protection.

In specific embodiments, the biofilm inhibitory compounds of this invention are non-bactericidal or can be employed at levels which are biofilm inhibitory without being bactericidal. In such embodiments, concerns associated with evolved resistance currently faced by approaches based on the use of conventional microbiocidal agents (e.g., antibiotics) are lessened.

The invention also provides compositions comprising a biofilm inhibitory compound of the invention in combination with other bioactive agents that inhibit biofilm formation or attenuate other bacterial behaviors (e.g., virulence, motility, etc.). The invention provides compositions comprising a biofilm inhibitory compound of the invention in combination with bacteriocidal and/or bacteriostatic agents, for examples one or more antibiotics. In a specific embodiment, such compositions comprise an amount of the one or more components effective for biofilm inhibition, attenuation of a selected bacterial behavior, bacterial growth inhibition or bacteriocidal effect.

In another aspect, the present invention provides a method of removing a biofilm from a surface, the method comprising the step of administering a cleaning-effective amount of one or more compounds of the present invention to a biofilm-containing surface. A preferred method of this aspect comprises the step of administering an effective amount of one or more compounds of the present invention to the surface, wherein the amount is effective to prevent biofilm formation. Such a surface may be a hard or rigid surface or a surface selected from the group consisting of glazed ceramic, porcelain, glass, metal, wood, chrome, plastic, vinyl, Formica, and the surface of a drainpipe. In an embodiment, the surface is a soft or flexible surface, or the surface is selected from the group consisting of a shower curtain or liner, upholstery, laundry, clothing, and carpeting. The compounds of the present invention are useful for removing or disrupting a biofilm is produced by a bacterium of the species *Pseudomonas*, a bacterium is of the species *Pseudomonas aeuroginosa*, or an organism selected from the group consisting of bacteria, algae, fungi and protozoa.

In various methods of the invention, one or more biofilm-inhibitory compounds can be combined as described herein with other bioactive ingredients, including among others one or more quorum sensing compounds, one or more antimicrobial agents or one or more antibiotics.

In another aspect, the invention provides a medicament for treating an infection or for disruption of a biofilm which comprises one or more of the compounds of this invention e.g., those of formulas I, IA1, IA2 and/or IB, and a method for making a medicament which comprises one or more of the compounds of this invention. In particular, the method comprises the step of combining one or more compounds of this invention with a pharmaceutically acceptable carrier to form a pharmaceutical composition for treatment of infection and/or biofilm formation.

One of ordinary skill in the art will recognize additional applications for the biofilm inhibitory compounds of this invention.

All references throughout this application, for example patent documents including issued or granted patents or equivalents; patent application publications; and non-patent literature documents or other source material; are hereby incorporated by reference herein in their entireties, as though individually incorporated by reference.

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups, including any isomers and enantiomers of the group members, and classes of compounds that can be formed using the substituents are disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

THE EXAMPLES

Example 1: Compound Synthesis and Characterization Data

A. 2-Nitro-4-styrylaniline

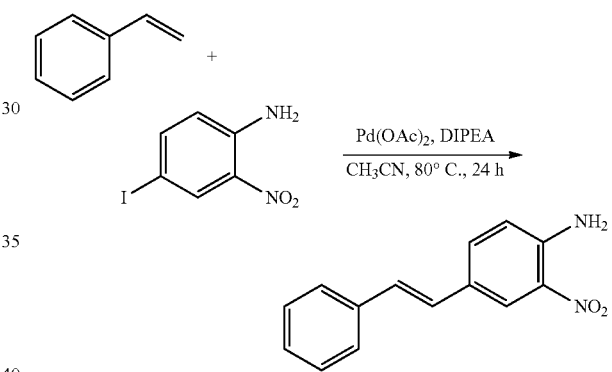

2-Nitro-4-styrylaniline was synthesized according to a modified version of a reported procedure. [35] In brief, 4-iodo-2-nitroaniline (500 mg, 1.89 mmol, 1.0 eq.) and palladium (II) acetate ($Pd(OAc)_2$, 21.3 mg, 0.095 mmol, 0.05 eq.) were added to an oven-dried Pyrex tube equipped with a magnetic stir bar at room temperature (rt). The tube was purged three times via three sequential vacuum/$N_2$ back-fill cycles. Next, freshly distilled styrene (260 µL, 2.27 mmol, 1.2 eq.), N,N-diisopropylethylamine (DIPEA, 825 µL, 4.74 mmol, 2.5 eq.), and acetonitrile ($CH_3CN$, 5 mL) were added under an $N_2$ atmosphere, and the reaction mixture was heated at 80° C. for 24 h. Upon cooling to rt, the solvent was removed in vacuo, and the resulting crude solid was adsorbed onto Florisil gel from a tetrahydrofuran (THF) solution. The resulting powder was dry-loaded on top of a silica gel column that was slurry-packed with ethyl acetate (EtOAc):hexanes (1:8). The column was eluted with a mixture of EtOAc:hexanes (1:8→1:7→1:6) to afford 2-nitro-4-styrylaniline as a bright red solid (346 mg, 1.44 mmol, 76% yield).

$^1$H NMR (300 MHz, Acetone-d6) δ 7.19 (m, 6H), 7.36 (m, 2H), 7.57 (m, 2H), 7.78 (dd, 1H, J=8.8, 2.0 Hz), 8.18 (d, 1H, J=2.0 Hz); $^{13}$C NMR (75 MHz, Acetone-d6) δ 120.7, 124.7, 127.1, 127.3, 127.8, 127.9, 128.3, 129.6, 133.9, 138.6, 146.4; EI-MS: calculated m/z [M]$^+$ 240.0894, observed m/z 240.0902.

B. 6-Styryl-2-aminobenzimidazole (1)

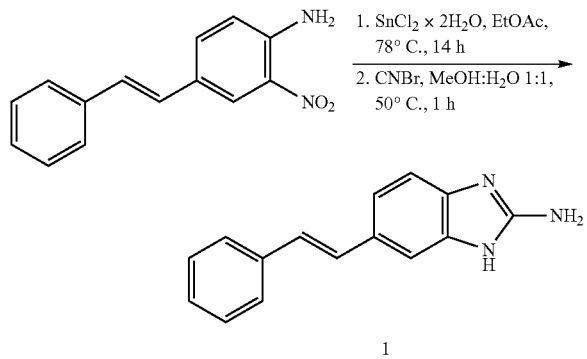

2-Nitro-4-styrylaniline (250 mg, 1.04 mmol, 1.0 eq.) was dissolved in EtOAc (30 mL) in a 100 mL round bottom flask equipped with a magnetic stir bar at rt, and the resulting clear red solution was treated with tin (II) dichloride dihydrate (SnCl$_2$.2H$_2$O, 1.17 g, 5.19 mmol, 5.0 eq.) The reaction mixture was stirred at reflux overnight (14 h), and upon cooling to rt, saturated aq. NaHCO$_3$ (50 mL) and an additional portion of EtOAc (20 mL) was added. The organic phase was washed with saturated aq. NaHCO$_3$ (2×30 mL), and the combined aqueous layers were washed with EtOAc (2×30 mL). The combined organic layers were dried over MgSO$_4$, and the solvent was removed in vacuo. The orange oil was dissolved in a 1:1 mixture of methanol (MeOH): water (40 mL), and cyanogen bromide (CNBr, 331 mg, 3.12 mmol, 3.0 eq.) was added. The reaction mixture was stirred at 50° C. for 1 h, after which the MeOH was removed in vacuo. The aqueous mixture was basified (pH~8) using 1.0 N aq. NaOH and extracted with EtOAc (3×30 mL). The combined organic layers were dried over MgSO$_4$, and the solvent was removed in vacuo. The crude solid was adsorbed onto Florisil gel from a THF solution. The resulting powder was dry-loaded on top of a silica gel column that was slurry-packed with acetone:hexanes (1:1). The column was then eluted with a mixture of acetone:hexanes (1:1) →acetone:MeOH (95:5) to afford 6-styryl-2-aminobenzimidazole (1) as a beige solid (223 mg, 0.95 mmol, 91% yield).

The corresponding HCl salt of 1 was prepared for biological testing by dissolving 6-styryl-2-aminobenzimidazole (100 mg, 0.42 mmol, 1.0 eq.) in 1,4-dioxane (5 mL) and adding 4.0 M HCl in 1,4-dioxane (532 µL, 2.13 mmol, 5.0 eq.) The resulting precipitate was filtered and dried in vacuo at 50° C. to give a white crystalline solid.

$^1$H NMR (300 MHz, DMSO-d6) δ 7.19 (d, 1H, J=16.5 Hz), 7.32 (m, 5H), 7.49 (dd, 1H, J=8.4, 1.3 Hz), 7.60 (m, 3H), 8.57 (s, 2H), 12.69 (bs, 2H); $^{13}$C NMR (75 MHz, DMSO-d6) δ 108.9, 111.5, 121.9, 126.4, 127.5, 127.6, 128.3, 128.7, 129.3, 130.3, 132.5, 137.0, 150.9; ESI-MS: calculated m/z [M+H]$^+$ 236.1183, observed m/z 236.1178.

C. Imidazo[1,2-a]pyrimidine Hydrobromide

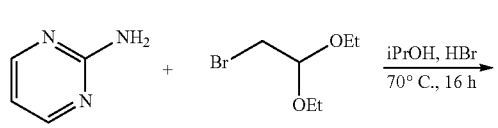

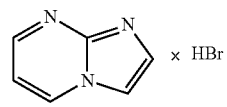

Imidazo[1,2-a]pyrimidine hydrobromide was synthesized according to a modified version of a reported procedure. [36] In brief, bromoacetaldehyde diethyl acetal (1.6 mL, 10.1 mmol, 1.5 eq.) was diluted with isopropyl alcohol (iPrOH, 20 mL) and hydrobromic acid (48% HBr, 414 µL, 8.11 mmol, 1.2 eq.) in a 50 mL round bottom flask equipped with a magnetic stir bar at rt. Next, 2-aminopyrimidine (644 mg, 6.77 mmol, 1.0 eq.) was added in three portions at rt yielding a white suspension. The reaction mixture was stirred overnight at 70° C. for 16 h (the white suspension turned into a clear solution after 15 min). Upon cooling to 0° C., a light beige suspension formed, which was filtered and washed with cold iPrOH (2×5 mL). The beige solid was dried in vacuo at 50° C. to afford imidazo[1,2-a]pyrimidine hydrobromide (882 mg, 4.41 mmol, 65% yield).

$^1$H NMR (300 MHz, DMSO-d6) δ 7.69 (dd, 1H, J=6.8, 4.4 Hz), 8.33 (d, 1H, J=2.2 Hz), 8.37 (d, 1H, J=2.3 Hz), 9.07 (dd, 1H, J=4.4, 1.8 Hz), 9.39 (dd, 1H, J=6.8, 1.8 Hz); $^{13}$C NMR (75 MHz, DMSO-d6) δ 113.8, 113.9, 123.2, 138.2, 143.3, 157.7; ESI-MS: calculated m/z [2M+H]$^+$ 239.1040, observed m/z 239.1049.

D. Triethylbenzylphosphonium bromide

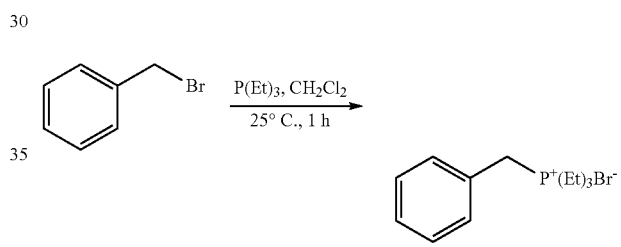

Triethylbenzylphosphonium bromide was synthesized according to a modified version of a reported procedure. [37] Triethylphosphine (P(Et)$_3$, 1.63 g, 13.9 mmol, 1.0 eq.) was added to an oven dried, 100 mL round bottom flask equipped with a magnetic stir bar in a glove box. The flask was sealed, removed from the glove box, cooled to 0° C., and CH$_2$Cl$_2$ (20 mL) and benzyl bromide (1.7 mL, 13.9 mmol, 1.0 eq.) were added via syringe. The solution was stirred and allowed to come to rt over 1 h. The solvent was removed in vacuo at 50° C. to afford triethylbenzylphosphonium bromide as a white crystalline solid (265 mg, 13.6 mmol, 98% yield).

$^1$H NMR (300 MHz, CDCl$_3$) δ 1.21 (m, 9H), 2.50 (m, 6H), 4.25 (d, 2H, J=15.1 Hz), 7.32 (m, 3H), 7.47 (m, 2H); $^{13}$C NMR (75 MHz, CDCl$_3$) δ 6.2, 12.3 (d, J=48 Hz), 26.3 (d, J=46 Hz), 128.6, 129.6, 130.3; ESI-MS: calculated m/z [M]$^+$ 209.1454, observed m/z 209.1461.

E. (E)-4-Bromostilbene

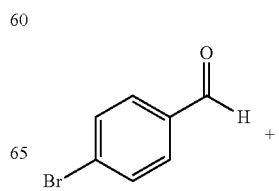

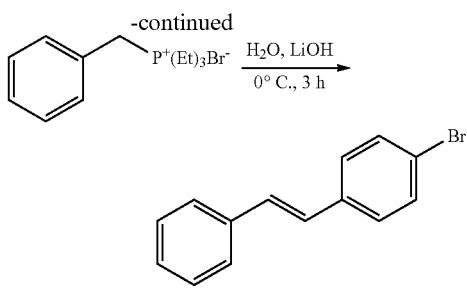

(E)-4-Bromostilbene was synthesized according to a modified version of a reported procedure. [37] Triethylphosphonium bromide (577 mg, 2.0 mmol, 1.05 eq.) and 18 MΩ water (0.8 mL) were added to a 25 mL round bottom flask equipped with a magnetic stir bar. The reaction mixture was stirred for 15 min at rt, after which lithium hydroxide (LiOH, 192 mg, 8.00 mmol, 4.2 eq.) was added slowly. After 2 min, 4-bromobenzaldehyde (352 mg, 1.9 mmol, 1.0 eq.) was added, and the white suspension was stirred in an oil bath at 70° C. for 3 h. The oil bath was removed, and the reaction was allowed to come to rt. Next, H$_2$O (10 mL) was added to the reaction mixture, and the mixture was stirred at rt for an additional 10 min. The suspension was filtered, and the isolated crystals were washed with cold H$_2$O (5 mL) and dried in vacuo. The crude stilbene product (E:Z=94:6 by $^1$H NMR) was adsorbed onto Florisil gel from a THF solution. The resulting powder was dry-loaded on top of a silica gel column that was slurry-packed with hexanes. The column was eluted with hexanes to afford pure (E)-4-bromostilbene as a white crystalline solid (414 mg, 1.60 mmol, 84% yield).

$^1$H NMR (300 MHz, CDCl$_3$) δ 7.02 (d, 1H, J=16.3 Hz), 7.10 (d, 1H, J=16.3 Hz), 7.27 (m, 1H), 7.36 (m, 4H), 7.49 (m, 4H); $^{13}$C NMR (75 MHz, CDCl$_3$) δ 121.5, 126.8, 127.6, 128.1, 128.2, 129.0, 129.6, 132.0, 136.5, 137.2; EI-MS: calculated m/z [M]$^+$ 258.0039, observed m/z 258.0051.

F. 3-(E)-Stilbene imidazo[1,2-a]pyrimidine

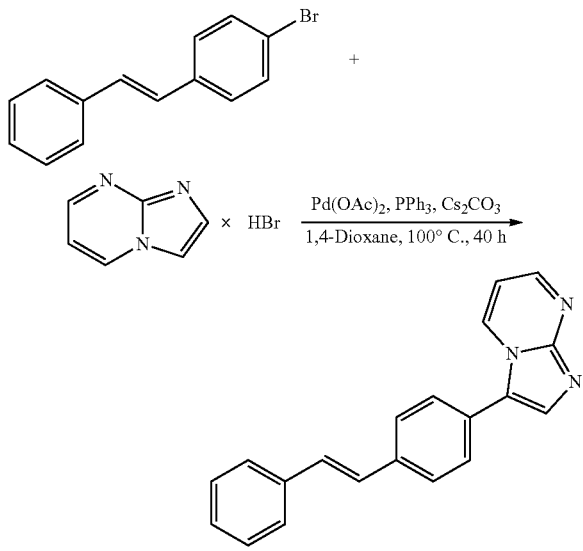

3-(E)-Stilbene imidazo[1,2-a]pyrimidine was synthesized according to a modified version of a reported procedure. [26] A mixture of (E)-4-bromostilbene (220 mg, 0.85 mmol, 1.2 eq.), imidazo[1,2-a]pyrimidine hydrobromide (142 mg, 0.71 mmol, 1.0 eq.), Pd(OAc)$_2$ (9.53 mg, 0.042 mmol, 0.05 eq.), triphenylphosphine (22.3 mg, 0.085 mmol, 0.1 eq.), and cesium carbonate (Cs$_2$CO$_3$, 463 mg, 1.42 mmol, 2.0 eq.) in 1,4-dioxane (2.0 mL) was added to a Schlenk tube equipped with a magnetic stir bar. The mixture was degassed using three vacuum/N$_2$ back-fill cycles, and the tube was placed in an oil bath at 100° C. and stirred for 40 h. Upon cooling to rt, the mixture was filtered through a plug of silica/sand/celite using acetone as the eluent. The acetone was removed in vacuo, and the crude product was adsorbed onto Florisil gel from a THF solution. The resulting powder was dry-loaded on top of a silica gel column that was slurry-packed with acetone:hexanes (1:3). The column was eluted with a mixture of acetone:hexanes (1:3→1:2→1:1) to afford 3-(E)-stilbene imidazo[1,2-a]pyrimidine as a light yellow solid (169 mg, 0.57 mmol, 82% yield).

$^1$H NMR (300 MHz, DMSO-d6) δ 7.38 (m, 5H), 7.60 (dd, 1H, J=7.0, 4.2 Hz), 7.66 (d, 2H, J=7.4 Hz), 7.76 (d, 2H, J=8.1 Hz), 7.87 (d, 2H, J=8.5 Hz), 8.54 (s, 1H), 9.03 (dd, 1H, J=4.2, 1.5 Hz), 9.33 (dd, 1H, J=7.0, 1.5 Hz); $^{13}$C NMR (75 MHz, DMSO-d6) δ 113.3, 127.3, 127.4, 128.0, 128.8, 130.0, 135.7, 136.7, 138.5, 143.3, 144.2, 156.2; ESI-MS: calculated m/z [M+H]$^+$ 298.1339, observed m/z 298.1337.

G. 4-(E)-Stilbene-2-aminoimidazole (2)

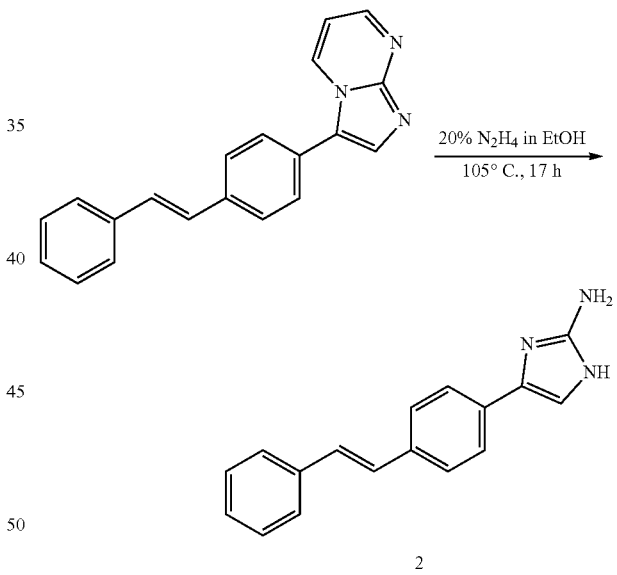

4-(E)-Stilbene-2-aminoimidazole (2) was synthesized according to a modified version of a reported procedure. [27] In brief, 3-(E)-stilbeneimidazo[1,2-a]pyrimidine (100 mg, 0.34 mmol, 1.0 eq.) was suspended in a 20% hydrazine solution (N$_2$H$_4$ in EtOH, 4.1 mL) in an oven dried Schlenk tube equipped with a magnetic stir bar. The tube was sealed, and the reaction mixture was stirred at 105° C. for 17 h. The resulting yellow solution was concentrated in vacuo, and the crude product was adsorbed onto Florisil gel from a THF solution. This powder was dry-loaded on top of a silica gel column that was slurry-packed with acetone:hexanes (1:2). The column was eluted with a mixture of acetone:hexanes (1:2→1:1) to afford 4-(E)-stilbene-2-aminoimidazole (2) as a light yellow solid (74 mg, 0.28 mmol, 84% yield).

The corresponding HCl salt was prepared for biological testing by dissolving 4-(E)-stilbene-2-aminoimidazole (50 mg, 0.19 mmol, 1.0 eq) in 1,4-dioxane (4 mL) and adding 4.0 M HCl in 1,4-dioxane (240 µL, 0.96 mmol, 5.0 eq.) The resulting precipitate was filtered and dried in vacuo at 50° C. to yield a light yellow crystalline solid.

$^1$H NMR (300 MHz, DMSO-d6) δ 7.27 (m, 3H), 7.39 (m, 2H), 7.45 (s, 1H), 7.47 (bs, 2H), 7.61 (m, 2H), 7.68 (m, 4H), 12.23 (bs, 1H), 13.05 (bs, 1H); $^{13}$C NMR (75 MHz, DMSO-d6) δ 109.5, 124.3, 126.1, 126.5, 126.8, 127.0, 127.7, 128.7, 128.8, 136.5, 136.9, 147.9; ESI-MS: calculated m/z [M+H]$^+$ 262.1339, observed m/z 262.134.

H. 5-Styryl-1H-indole (4a)

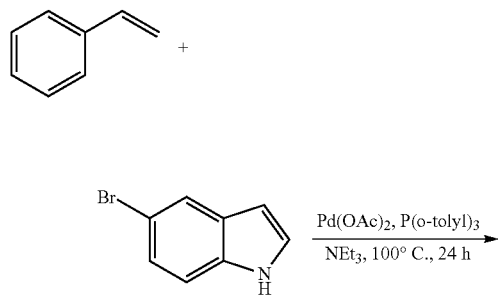

4a

5-Styryl-1H-indole (4a) was synthesized according to a slightly modified version of a reported procedure. [28] To an oven dried Schlenk tube charged with a magnetic stir bar was added Pd(OAc)$_2$ (22.5 mg, 0.10 mmol, 0.05 eq.), tri(o-tolyl)phosphine (P(o-tolyl)$_3$, 60.9 mg, 0.20 mmol, 0.10 eq.), 5-bromo-1H-indole (393 mg, 2.0 mmol, 1.0 eq.), styrene (287 µL, 2.5 mmol, 1.25 eq.), and triethylamine (NEt$_3$, 2.0 mL). The mixture was degassed using three vacuum/N$_2$ back-fill cycles, and heated at 100° C. for 24 h. Upon cooling to room temperature, the mixture was filtered through a plug of silica/sand/celite using acetone as the eluent. The acetone was concentrated in vacuo, and the crude product was adsorbed onto Florisil gel from a THF solution. The resulting powder was dry-loaded on top of a silica gel column that was slurry-packed with EtOAc: hexanes (1:8). The column was eluted with a mixture of EtOAc:hexanes (1:8→1:5) to afford 5-styryl-1H-indole (4a) as a white solid (332 mg, 1.51 mmol, 76% yield).

$^1$H NMR (300 MHz, Acetone-d6) δ 6.51 (t, 1H, J=2.3 Hz), 7.16 (d, 1H, J=16.3 Hz), 7.22 (m, 1H), 7.35 (m, 4H), 7.46 (m, 2H), 7.59 (d, 2H, J=7.4 Hz) 7.78 (s, 1H), 10.28 (bs, 1H); $^{13}$C NMR (75 MHz, Acetone-d6) δ 102.9, 112.5, 120.3, 120.9, 126.2, 126.4, 127.0, 127.7, 129.5, 129.9, 131.3, 137.2, 139.2; ESI-MS: calculated m/z [M+H]$^+$219.1043, observed m/z 219.1049.

I. 6-Styryl-1H-indole (4b)

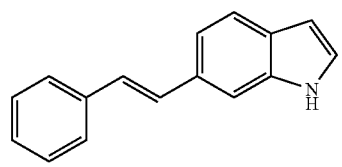

6-Styryl-1H-indole (4b) was synthesized according to the procedure above for 5-styryl-1 H-indole (4a). The crude product was purified by flash silica gel chromatography via dry loading on top of a silica gel column that was slurry-packed with acetone:hexanes (1:9). The column was eluted with a mixture of acetone:hexanes (1:9→1:7) to afford 6-styryl-1H-indole (4b) as a white solid (322 mg, 1.47 mmol, 73% yield).

$^1$H NMR (300 MHz, Acetone-d6) δ 6.47 (m, 1H), 7.18 (d, 1H, J=16.4 Hz), 7.23 (m, 1H), 7.35 (m, 5H), 7.59 (m, 4H), 10.29 (bs, 1H); $^{13}$C NMR (75 MHz, Acetone-d6) δ 102.7, 110.7, 111.1, 118.9, 121.3, 126.7, 126.9, 127.1, 127.9, 129.2, 129.6, 131.2, 132.0, 137.7, 139.1; ESI-MS: calculated m/z [M+H]$^+$ 219.1043, observed m/z 219.1043.

J. 6-Chloro-1-(N,N-dimethylsulfamoyl)-benzimidazole

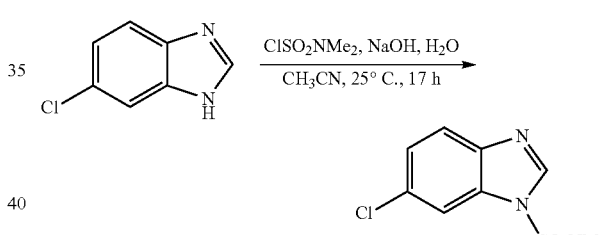

A solution of sodium hydroxide pellets (1.05 g, 26.3 mmol, 2.0 eq.) in a mixture of water (3.6 mL) and CH$_3$CN (50 mL) was prepared in a 100 mL round bottom flask equipped with a stir bar. 5-Chlorobenzimidazole (2.0 g, 13.1 mmol, 1.0 eq.) was added to this solution in four portions. N,N-Dimethylsulfamoyl chloride (ClSO$_2$NMe$_2$, 1.4 mL, 15.0 mmol, 1.0 eq.) was then added drop-wise, and the resulting mixture was stirred at 25° C. for 17 h. The solvent was removed in vacuo, and the remaining suspension was poured onto an ice/water slurry (100 mL) and stirred for an additional 30 min. The precipitate was filtered, washed with water (3×10 mL), and dried in vacuo at 50° C. to obtain a 1:1 mixture (according to $^1$H NMR) of 5- and 6-chloro-1-(N,N-dimethylsulfamoyl)-benzimidazole as a white solid (3.22 g, 12.4 mmol, 95% yield). The isomers were separated by flash silica gel chromatography using a mixture of acetone: hexanes (1:2→1:1) to afford pure 6-chloro-1-(N,N-dimethylsulfamoyl)-benzimidazole as a white solid.

$^1$H NMR (300 MHz, Acetone-d6) δ 3.03 (s, 6H), 7.41 (dd, 1H, J=8.6, 2.1 Hz), 7.77 (d, 1H, J=8.5 Hz), 7.91 (d, 2H, J=2.0 Hz), 8.47 (s, 1H); $^{13}$C NMR (75 MHz, Acetone-d6) δ 38.7, 113.8, 122.8, 125.6, 131.2, 133.6, 143.4, 143.9; ESI-MS: calculated m/z [M+H]$^+$ 260.0256, observed m/z 260.0246.

K. 6-Styryl-1-(N,N-dimethylsulfamoyl)-benzimidazole

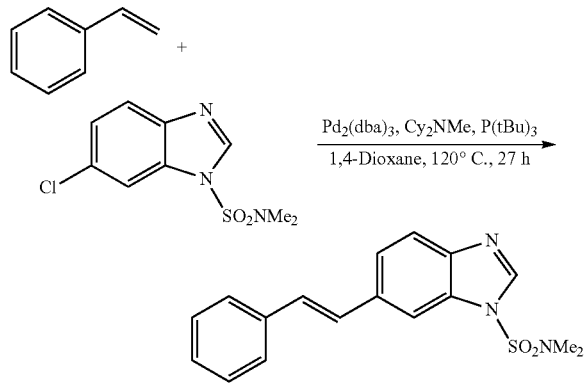

6-Styryl-1-(N,N-dimethylsulfamoyl)-benzimidazole was synthesized according to a modified version of a reported procedure. [38] Tris(dibenzylideneacetone)-dipalladium (0) (Pd$_2$(dba)$_3$, 34.7 mg, 0.038 mmol, 0.05 eq.), tri-tert-butyl-phosphine (P(tBu)$_3$, 35.1 mg, 0.17 mmol, 0.22 eq.), and distilled 1,4-dioxane (1.86 g) was added to an oven dried Schlenk tube charged with a magnetic stir bar in a glove box. The Schlenk tube was capped with a glass stopper and removed from the glove box. Next, 6-chloro-1-(N,N-dimethylsulfamoyl)-benzimidazole (200 mg, 0.77 mmol, 1.0 eq.), N,N-dicyclohexylmethylamine (Cy$_2$NMe, 205 µL, 0.92 mmol, 1.2 eq.), and freshly distilled styrene (106 µL, 0.92 mmol, 1.2 eq.) were added to the Schlenk tube under N$_2$. The tube was heated to 120° C. and stirred for 27 h. The mixture was allowed to come to room temperature, and then filtered through a plug of silica/sand/celite with acetone. The solvent was removed in vacuo, and the crude product was purified by flash silica gel chromatography using a mixture of acetone:hexanes (9:1→4:1) to afford 6-styryl-1-(N,N-dimethylsulfamoyl)-benzimidazole as a white solid (225 mg, 0.69 mmol, 89% yield).

$^1$H NMR (300 MHz, Acetone-d6) δ 3.02 (s, 6H), 7.30 (m, 1H), 7.39 (m, 3H), 7.47 (d, 1H, J=16.4 Hz), 7.65 (m, 2H), 7.74 (m, 2H) 8.08 (s, 1H), 8.41, (s, 1H); $^{13}$C NMR (75 MHz, Acetone-d6) δ 38.7, 112.1, 121.7, 123.5, 127.6, 128.6, 129.5, 129.6, 130.0, 133.6, 136.0, 138.4, 143.5; ESI-MS: calculated m/z [M+H]$^+$ 328.1115, observed m/z 328.1104.

L. 6-Styryl-1H-benzimidazole (5)

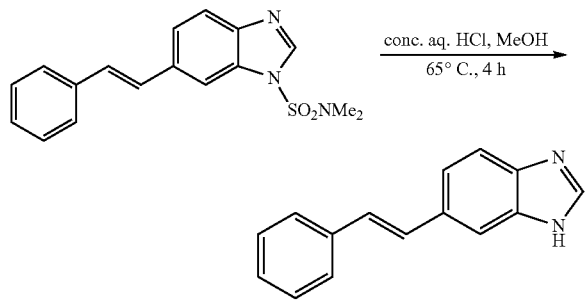

6-Styryl-1-(N,N-dimethylsulfamoyl)-benzimidazole (170 mg, 0.52 mmol, 1.0 eq.) was dissolved in MeOH (10 mL) in a 25 mL round bottom flask equipped with a magnetic stir bar. Concentrated aq. HCl (200 µL) was added, and the reaction mixture was heated at reflux for 4 h. Upon cooling to room temperature, the pH was adjusted to ~12 using a 1% KOH in MeOH solution. The solvent was removed in vacuo, and the crude product was purified by flash silica gel chromatography using a mixture of acetone:hexanes (1:1) to afford 6-styryl-1H-benzimidazole (5) as a white solid (113 mg, 0.51 mmol, 99% yield).

The corresponding HCl salt of 5 was prepared for biological testing by dissolving 6-styryl-1H-benzimidazole (50 mg, 0.23 mmol, 1.0 eq.) in 1,4-dioxane (3 mL) and adding 4.0 M HCl in 1,4-dioxane (284 µL, 1.13 mmol, 5.0 eq.) The resulting precipitate was filtered and dried in vacuo at 50° C. to yield a white crystalline solid.

$^1$H NMR (300 MHz, Acetone-d6) δ 7.23 (m, 2H), 7.38 (m, 3H), 7.55 (dd, 1H, J=8.5, 1.5 Hz), 7.62 (m, 3H), 7.83 (s, 1H), 8.19 (s, 1H) 11.54 (bs, 1H); $^{13}$C NMR (75 MHz, DMSO-d6) δ 112.0, 114.6, 124.3, 126.6, 127.6, 127.9, 128.7, 129.6, 130.0, 131.3, 135.4, 136.7, 140.4; ESI-MS: calculated m/z [M+H]$^+$ 221.1074, observed m/z 221.1080.

M. Stilbene (6), 2-aminobenzimidazole (2-ABI; 7), 2-aminoimidazole (2-AI; 8), and Guanidine (9)

These compounds were purchased from commercial sources. 2-ABI (7) and 2-AI (8) were converted to the corresponding HCl salts for biological testing; guanidine (9) was purchased as the HCl salt.

N. 5-Iodo-2-aminobenzimidazole (10)

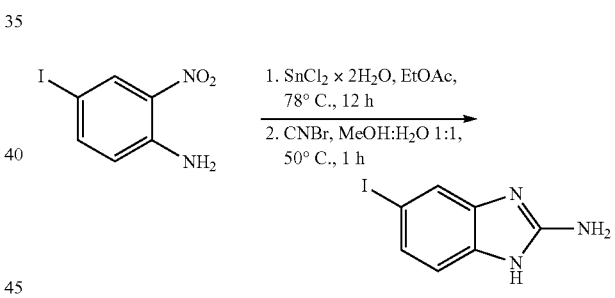

4-Iodo-2-nitroaniline (440 mg, 1.67 mmol, 1.0 eq.) was dissolved in EtOAc (50 mL) in a 100 mL round bottom flask at room temperature, and SnCl$_2$.2H$_2$O (1.88 g, 8.33 mmol, 5.0 eq.) was added. The reaction mixture was stirred at reflux for 12 h and extracted upon cooling to room temperature with saturated aq. NaHCO$_3$ (3×30 mL). The combined aqueous layers were washed with EtOAc (2×30 mL). The resulting organic layers were combined and dried over MgSO$_4$, and the solvent was removed in vacuo.

The 4-iodo-1,2-phenylenediamine intermediate was dissolved in a 1:1 mixture of MeOH:water (30 mL), and CNBr (530 mg, 5.00 mmol, 3.0 eq.) was added. The reaction mixture was stirred at 50° C. for 1 h, after which MeOH was removed in vacuo. The remaining slurry was basified (to pH ~8) using 1.0 M aq. NaOH and extracted with EtOAc (3×30 mL). The combined organic fractions were washed with water (2×30 mL), brine (30 mL), dried over MgSO$_4$ and concentrated in vacuo to afford 5-iodo-2-aminobenzimidazole (10) as a light brown solid (285 mg, 1.10 mmol, 66% yield). The corresponding HCl salt was prepared for biological testing by dissolving 5-iodo-2-aminobenzimidazole (10, 95 mg, 0.37 mmol, 1.0 eq.) in 1,4-dioxane (4 mL) and adding 4.0 M HCl in 1,4-dioxane (458 μL, 1.83 mmol, 5.0 eq.) The resulting precipitate was filtered and dried in vacuo at 50° C. to yield a light brown crystalline solid.

$^1$H NMR (300 MHz, DMSO-d6) δ 7.20 (d, 1H, J=6.1 Hz), 7.48 (d, 1H, J=5.6 Hz), 7.69 (s, 1H), 8.74 (s, 2H), 12.80 (bs, 2H); $^{13}$C NMR (75 MHz, DMSO-d6) δ 85.7, 113.4, 119.4, 129.3, 131.2, 131.3, 150.3; ESI-MS: calculated m/z [M+H]$^+$ 259.9680, observed m/z 259.9677.

Representative Procedures for the Synthesis of 2-ABI Derivatives 11-15, 17-22, and 24

O. 5-Bromo-2-aminobenzimidazole (11)

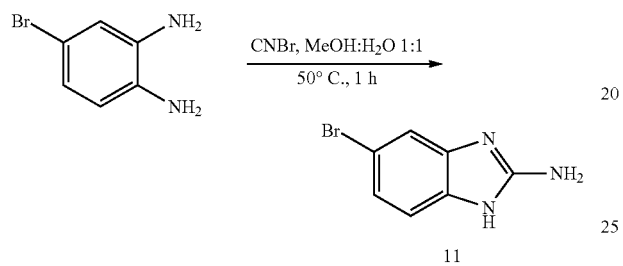

11

5-Bromo-2-aminobenzimidazole (11) was synthesized according to a modified version of a reported procedure. [31] In brief, 4-bromo-1,2-diaminobenzene (1.0 g, 5.35 mmol, 1.0 eq.) was dissolved in a 1:1 mixture of MeOH (40 mL) and water (40 mL) in a 250 mL round bottom flask. The reaction mixture was treated with CNBr (1.7 g, 16.04 mmol, 3.0 eq.) and heated at 50° C. for 1 h. After cooling to room temperature, the MeOH was removed in vacuo, and the remaining mixture was basified with 1.0 M aq. NaOH (to pH=8.0) and extracted with EtOAc (3×30 mL). The combined organic fractions were washed with water (2×50 mL), brine (50 mL), dried over MgSO$_4$ and concentrated in vacuo to afford 5-bromo-2-aminobenzimidazole (11) as a red solid (1.07 g, 5.05 mmol, 94% yield).

The corresponding HCl salt of 11 was prepared for biological testing by dissolving 5-bromo-2-aminobenzimidazole (11, 100 mg, 0.47 mmol, 1.0 eq.) in 1,4-dioxane (5 mL) and adding 4.0 M HCl in 1,4-dioxane (589 μL, 2.36 mmol, 5.0 eq.) The resulting precipitate was filtered and dried in vacuo at 50° C. to yield a red crystalline solid.

$^1$H NMR (300 MHz, DMSO-d6) δ 7.32 (dd, 1H, J=8.4, 0.6 Hz), 7.36 (dd, 1H, J=8.4, 1.7 Hz), 7.55 (dd, 1H, J=1.7, 0.6 Hz), 8.72 (s, 2H), 12.77 (bs, 2H); $^{13}$C NMR (75 MHz, DMSO-d6) δ 113.1, 114.1, 114.5, 125.6, 129.1, 131.2, 150.9; ESI-MS: calculated m/z [M+H]$^+$ 211.9818, observed m/z 211.9811.

P. 5-Chloro-2-aminobenzimidazole (12)

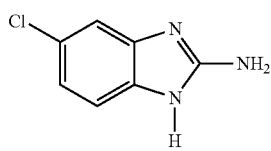

12

5-Chloro-2-aminobenzimidazole (12) was synthesize as described in Example 1-O employing 4-chloro-1,2-diaminobenzene and isolated as a purple solid (964 mg, 5.75 mmol, 82% yield) and converted to the corresponding HCl salt for biological testing. $^1$H NMR (300 MHz, DMSO-d6) δ 7.25 (dd, 1H, J=8.5, 1.9 Hz), 7.36 (d, 1H, J=8.5 Hz), 7.41 (d, 1H, J=1.9 Hz), 8.59 (s, 2H), 12.55 (bs, 2H); $^{13}$C NMR (75 MHz, DMSO-d6) δ 111.3, 112.7, 122.9, 127.0, 128.6, 130.7, 150.9; ESI-MS: calculated m/z [M+H]$^+$ 168.0323, observed m/z 168.0320.

Q. 5-Fluoro-2-aminobenzimidazole (13)

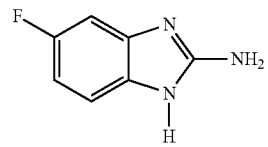

13

5-Fluoro-2-aminobenzimidazole (13) was synthesize as described in Example 1-O employing 4-fluoro-1,2-diaminobenzene and isolated as a light brown solid (1.07 g, 7.06 mmol, 89% yield) and converted to the corresponding HCl salt for biological testing. $^1$H NMR (300 MHz, DMSO-d6) δ 7.04 (m, 1H), 7.24 (dd, 1H, J=8.8, 2.5 Hz), 7.36 (dd, 1H, J=8.8, 4.7 Hz), 8.66 (s, 2H), 12.73 (bs, 2H); $^{13}$C NMR (75 MHz, DMSO-d6) δ 99.1, 109.9 (d, J=24 Hz), 112.3, 126.2, 130.3 (d, J=13 Hz), 151.3, 158.5 (d, J=237 Hz); ESI-MS: calculated m/z [M+H]$^+$ 152.0619, observed m/z 152.0617.

R. 5-Benzoyl-2-aminobenzimidazole (14)

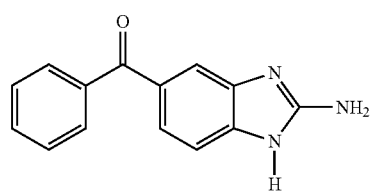

14

5-Benzoyl-2-aminobenzimidazole (14) was synthesize as described in Example 1-O employing 4-benzoyl-1,2-diaminobenzene and isolated as a light beige solid (1.03 g, 4.33 mmol, 92% yield) and converted to the corresponding HCl salt for biological testing. $^1$H NMR (300 MHz, DMSO-d6) δ 7.62 (m, 8H), 8.86 (s, 2H), 12.89 (bs, 2H); $^{13}$C NMR (75 MHz, DMSO-d6) δ 111.1, 113.1, 125.6, 128.5, 129.4, 129.8, 131.7, 132.3, 133.3, 137.5, 151.6, 194.8; ESI-MS: calculated m/z [M+H]$^+$ 238.0975, observed m/z 238.0979.

S. 5-Carboxylic acid methyl ester-2-aminobenzimidazole (15)

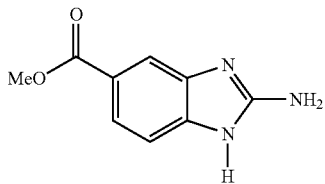

15

5-Carboxylic acid methyl ester-2-aminobenzimidazole (15) was synthesize as described in Example 1-0 employing 4-carboxylic acid methyl ester-1,2-diaminobenzene and isolated as a light beige solid (1.09 g, 5.71 mmol, 95% yield) and converted to the corresponding HCl salt for biological testing. $^1$H NMR (300 MHz, DMSO-d6) δ 3.86 (s, 3H), 7.46 (d, 1H, J=8.4 Hz), 7.83 (dd, 1H, J=8.4, 1.2 Hz), 7.92 (d, 1H, J=1.2 Hz), 8.85 (s, 2H), 12.95 (bs, 2H); $^{13}$C NMR (75 MHz, DMSO-d6) δ 52.2, 111.2, 112.2, 124.1, 124.5, 129.8, 133.5, 151.5, 165.9; EI-MS: calculated m/z [M]$^+$ 191.0690, observed m/z 191.0694.

T. 5-Cyano-2-aminobenzimidazole (17)

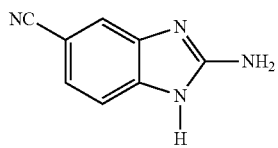

17

5-Cyano-2-aminobenzimidazole (17) was synthesize as described in Example 1-0 employing 4-cyano-1,2-diaminobenzene and isolated as a light brown solid (1.03 g, 6.53 mmol, 87% yield) and converted to the corresponding HCl salt for biological testing. $^1$H NMR (300 MHz, DMSO-d6) δ 7.52 (dd, 1H, J=8.3, 0.6 Hz), 7.65 (m, 1H), 7.80 (Dd, 1H, J=1.5, 0.4 Hz), 8.98 (s, 2H), 13.08 (bs, 2H); $^{13}$C NMR (75 MHz, DMSO-d6) δ 104.8, 112.4, 115.1, 119.1, 127.5, 130.0, 133.5, 151.8; ESI-MS: calculated m/z [M+H]$^+$159.0666, observed m/z 159.0662.

U. 5-Nitro-2-aminobenzimidazole (18)

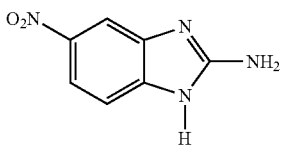

18

5-Nitro-2-aminobenzimidazole (18) was synthesize as described in Example 1-0 employing 4-nitro-1,2-diaminobenzene and isolated as a yellow solid (3.28 g, 18.4 mmol, 94% yield) and converted to the corresponding HCl salt for biological testing. $^1$H NMR (300 MHz, DMSO-d6) δ 7.54 (dd, 1H, J=8.7, 0.4 Hz), 8.13 (dd, 1H, J=8.7, 2.3 Hz), 8.18 (m, 1H), 9.03 (s, 2H), 13.12 (bs, 2H); $^{13}$C NMR (75 MHz, DMSO-d6) δ 107.2, 111.5, 119.3, 130.1, 135.2, 142.9, 152.4; ESI-MS: calculated m/z [M+H]$^+$ 179.0564, observed m/z 179.0570.

V. 4-Methyl-2-aminobenzimidazole (19)

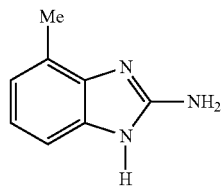

19

4-Methyl-2-aminobenzimidazole (19) was synthesize as described in Example 1-0 employing 3-methyl-1,2-diaminobenzene and isolated as a light orange solid (1.16 g, 7.86 mmol, 96% yield) and converted to the corresponding HCl salt for biological testing. $^1$H NMR (300 MHz, DMSO-d6) δ 3.73 (s, 3H), 6.76 (dd, 1H, J=8.7, 2.4 Hz), 6.93 (d, 1H, J=2.3 Hz), 7.24 (d, 1H, J=8.7 Hz), 8.44 (s, 2H), 12.52 (bs, 2H); $^{13}$C NMR (75 MHz, DMSO-d6) δ 16.4, 108.9, 121.2, 123.0, 124.0, 128.6, 129.3, 150.7; ESI-MS: calculated m/z [M+H]$^+$ 148.0870, observed m/z 148.0866.

W. 5-Methyl-2-aminobenzimidazole (20)

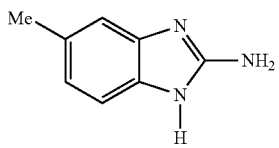

20

5-Methyl-2-aminobenzimidazole (20) was synthesize as described in Example 1-O employing 4-methyl-1,2-diaminobenzene and isolated as a brown solid (1.12 g, 7.61 mmol, 93% yield). Several methods failed to produce a corresponding HCl salt; therefore, 5-methyl-2-aminobenzimidazole (20) underwent biological evaluation as the non-HCl salt. We note that both the HCl salt and non-HCl version of 2-aminobenzimidazole gave identical values for inhibitory biofilm growth assays (data not shown). $^1$H NMR (300 MHz, DMSO-d6) δ 2.30 (s, 3H), 6.12 (bs, 2H), 6.67 (m, 1H), 6.91 (dd, 1H, J=1.6, 0.6 Hz), 6.97 (d, 1H, J=8.0 Hz); $^{13}$C NMR (75 MHz, DMSO-d6) δ 21.2, 111.1, 112.0, 120.1, 127.9, 136.1, 138.5, 155.0; ESI-MS: calculated m/z [M+H]$^+$ 148.0870, observed m/z 148.0867.

X. 5,6-Dimethyl-2-aminobenzimidazole (21)

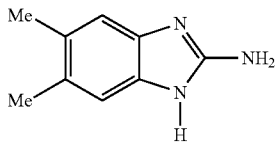

21

5,6-Dimethyl-2-aminobenzimidazole (21) was synthesize as described in Example 1-O employing 4,5-dimethyl-1,2-diaminobenzene and isolated as a light brown solid (1.14 g, 7.05 mmol, 96% yield) and converted to the corresponding HCl salt for biological testing. $^1$H NMR (300 MHz, DMSO-d6) δ 2.25 (s, 6H), 7.14 (s, 2H), 8.37 (s, 2H), 12.47 (bs, 2H); $^{13}$C NMR (75 MHz, DMSO-d6) δ 19.6, 111.8, 127.7, 131.1, 150.1; EI-MS: calculated m/z [M]$^+$ 161.0948, observed m/z 161.0948.

Y. 5-Methoxy-2-aminobenzimidazole (22)

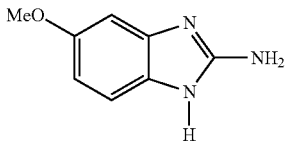

5-Methoxy-2-aminobenzimidazole (22) was synthesize as described in Example 1-0 employing 4-methoxy-1,2-diaminobenzene and isolated as a white solid (696 mg, 4.26 mmol, 90% yield) and converted to the corresponding HCl salt for biological testing. $^1$H NMR (300 MHz, DMSO-d6) δ 3.75 (s, 3H), 6.78 (dd, 1H, J=8.7, 2.4 Hz), 6.95 (d, 1H, J=2.3 Hz), 7.27 (d, 1H, J=8.7 Hz), 8.47 (s, 2H), 12.55 (bs, 2H); $^{13}$C NMR (75 MHz, DMSO-d6) δ 55.6, 96.8, 109.9, 111.9, 123.4, 130.4, 150.6, 155.9; ESI-MS: calculated m/z [M+H]$^+$ 164.0819, observed m/z 164.0817.

Z. 2-Amino-1H-naphtho[2,3-d]imidazole (24)

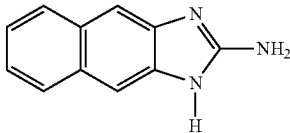

2-Amino-1H-naphtho[2,3-d]imidazole (24) was synthesize as described in Example 1-0 employing 1,2-diaminonaphthylene and isolated as a light brown solid (104 mg, 0.56 mmol, 93% yield) and converted to the corresponding HCl salt for biological testing. $^1$H NMR (300 MHz, DMSO-d6) δ 7.42 (m, 2H), 7.80 (s, 4H), 7.96 (m, 2H), 8.93 (s, 2H), 12.80 (bs, 2H); $^{13}$C NMR (75 MHz, DMSO-d6) δ 107.3, 124.5, 127.5, 129.8, 130.3, 152.8; ESI-MS: calculated m/z [M+H]$^+$ 184.0870, observed m/z 184.0866.

AA. 5-Carboxylic acid-2-aminobenzimidazole (16)

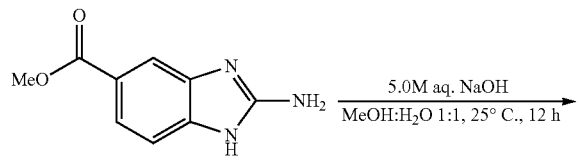

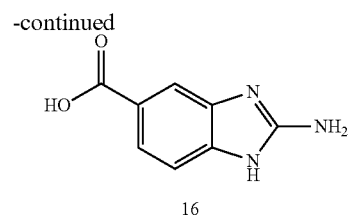

5-Carboxylic acid methyl ester-2-aminobenzimidazole (350 mg, 1.83 mmol, 1.0 eq, 15) was dissolved in a 1:1 mixture of MeOH (10 mL) and water (10 mL) in a 100 mL round bottom flask, and treated with 5.0 M aq. NaOH (10 mL). The reaction mixture was stirred for 12 h at rt, after which the MeOH was removed in vacuo. The aqueous solution was cooled to 0° C., and concentrated aq. HCl was added until pH ~2 was reached. The resulting precipitate was filtered and dried in vacuo at 50° C. to afford the HCl salt of 5-carboxylic acid-2-aminobenzimidazole (16) as a light brown crystalline solid (356 mg, 1.67 mmol, 91% yield).

$^1$H NMR (300 MHz, DMSO-d6) δ 7.45 (d, 1H, J=8.3 Hz), 7.81 (dd, 1H, J=8.4, 1.5 Hz), 7.92 (d, 1H, J=1.4 Hz), 8.90 (s, 2H), 12.99 (bs, 2H); $^{13}$C NMR (75 MHz, DMSO-d6) δ 111.1, 112.5, 124.7, 125.5, 129.8, 133.2, 151.5, 167.0; EI-MS: calculated m/z [M]$^+$ 177.0533, observed m/z 177.0536.

BB. 2,5-Diaminobenzimidazole (23)

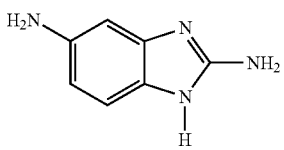

The dihydrochloride salt of 2,5-diaminobenzimidazole (23) was synthesized according to a reported procedure [39] and isolated as a light brown crystalline solid (76 mg, 0.34 mmol, 81% yield). $^1$H NMR (300 MHz, DMSO-d6) δ 7.24 (dd, 1H, J=8.5, 1.7 Hz), 7.44 (d, 1H, J=8.4 Hz), 7.52 (d, 1H, J=1.5 Hz), 8.80 (s, 2H), 11.54 (bs, 4H); $^{13}$C NMR (75 MHz, DMSO-d6) δ 106.8, 112.1, 118.1, 127.0, 129.1, 130.1, 151.2; ESI-MS: calculated m/z [M+H]$^+$ 149.0822, observed m/z 149.0825.

General Experimental Information—Synthesis

All chemical reagents were purchased from commercial sources (Alfa-Aesar, Sigma-Aldrich, and Acros) and used without further purification. Solvents were purchased from commercial sources (Sigma-Aldrich and J. T. Baker) and used as obtained, with the exception of dichloromethane ($CH_2Cl_2$), which was distilled over calcium hydride immediately prior to use. Water was purified using a Millipore Analyzer Feed System. $^1$H NMR spectra were recorded in deuterated NMR solvents at 300 MHz on a Varian Mercury-300 spectrometer. Chemical shifts are reported in parts per million (ppm, δ) using corresponding solvents or tetramethylsilane (TMS) as a reference. Couplings are reported in hertz (Hz). Electrospray ionization (ESI) MS data were obtained using a Waters (Micromass) LCT™ system. This instrument uses a time-of-flight analyzer. Samples were dissolved in methanol and sprayed with a sample cone voltage of 20. Electron impact (EI) MS data were obtained using a Waters (Micromass) AutoSpec® system. UV spectra were recorded using a Varian Cary 50 UV-Vis spectrometer running Cary WinUV software.

Example 2: Biological Assays

A. General.

Standard solvents, salts, and media were purchased from commercial sources and used as received. The HCl salt of synthetic compounds were used for biological evaluation if available; however, control experiments indicated that the HCl salt and the non-HCl versions had identical biological activities (data not shown). All biological assays were performed in untreated, flat-bottomed polystyrene 96-well microtiter plates (Costar 3370).

Absorbance and fluorescence measurements were obtained using a BioTek Synergy 2 plate reader running Gen 5 1.05 software. Spectroscopic measurements were made in 200 μL of media in 96-well microtiter plates (path length of ~0.5 cm) unless otherwise noted. Bacterial growth was assessed by measuring the culture cell density according to absorbance at 600 nm ($OD_{600}$). Biofilm was quantified by crystal violet (CV) staining according to absorbance at 590 nm (A590). All reported CV measurements represent the amount of surface-attached (SA) biofilm at the bottom of the microtiter plate wells; the amount of air-liquid interface (Int) biofilm and total (Ttl) biofilm was also measured, but are not reported here. GFP fluorescence (FL500/540) was measured at an excitation wavelength of 500 nm (27 nm bandwidth) and emission wavelength of 540 nm (25 nm bandwidth) [sensitivity set to 65, optics position set to top 50% (excitation and emission min/max of 200/850)]. Electroporation was performed in a Bio-Rad electroporation cuvette (0.2 cm gap) using a Bio-Rad Gene Pulser XCell™ electroporator (2.5 kV, 25 uF, 200Ω). Colony Polymerase Chain Reactions (PCR) were performed using an Eppendorf Mastercycler® programmed as follows: 98° C., 5 min; 25 cycles [98° C. 30 sec; 66° C. 30 sec; 72° C. 30 sec]; 72° C., 5 min. PCR DNA products were analyzed by gel electrophoresis by applying 120 V for 1 h across 1% agarose gels in TAE buffer (Tris base/Acetic acid/EDTA).

Assay data were analyzed using Microsoft Office Excel 2007 and GraphPad Prism version 5.04 for Windows (GraphPad Software, Inc.) Data are shown as percent of the "no compound" positive control and represent the average and standard error (STE) of 3-6 replicate wells from a single trial; we note that replicate trials gave similar results as the single trials reported here. Half maximal inhibitory concentration ($IC_{50}$) values and half maximal dispersal concentration ($DC_{50}$) values were calculated using a sigmoidal curve fit (three parameters) in GraphPad Prism and are reported with a 95% confidence interval (95% CI).

B. Bacterial Strains and Plasmids.

The *Pseudomonas aeruginosa* strains PAO1, PAO-JP2, PAO-JP2/plasI-LVAgfp, and PAO-JP2/prhII-LVAgfp were provided by Professor Barbara Iglewski (University of Rochester). [40] The *Escherichia coli* strains XL1-Blue/pBKminiTn7-gfp2, SM10::λpir/pUX-BF13, and HB101/pRK600 were provided by Professor Søren Molin (Technical University of Denmark). [41, 42] The *E. coli* S17-1::λpir mating strain was provided by Professor Eric Strieter (University of Wisconsin-Madison). [43] Freezer stocks of bacterial strains were maintained at −80° C. in Luria Bertani (LB) medium and 20-50% glycerol. Bacterial samples were prepared from overnight cultures, which were inoculated with single colonies that were isolated by streaking a freezer stock on an LB/agar (1.5%) plate. All bacteria were grown at 37° C. and under static conditions, with the exception of overnight cultures that were shaken at 200 rpm. Plasmid DNA stocks were stored at −20° C. in sterile 18 MΩ $H_2O$.

C. Media and Solutions.

All glassware was cleaned with hot $H_2O$/alconox, EtOH, $dH_2O$, 1 N $HNO_3$ (to remove trace metals), and 18 MΩ $H_2O$. All solutions were prepared using 18 MΩ $H_2O$ to minimize trace metal contamination. All buffers and media were at approximate physiological pH 7.35 unless otherwise noted. Non-growth supporting solutions were either left untreated or sterilized by autoclave. For growth supporting solutions, glassware was sterilized by autoclave and final solution sterilization was completed by passing through a 0.22 μm PES (PolyEtherSulphone) membrane filter. Autoclaving of media for biofilm growth was avoided as high temperatures were observed to give undesired precipitation of salts and/or side reactions. Solutions were stored at rt indefinitely until depleted or sign of contamination.

LB medium was prepared to 2% (w/v) in 18 MΩ $H_2O$ per manufacturer's instructions. *P. aeruginosa* assays were performed in a supplemented M9 minimal medium designated here as M9+, which was optimized for the production of robust, quorum sensing (QS)-dependent SA biofilms as observed by CV staining in 96-well microtiter plates (data not shown). M9+ medium was adapted from the M9 minimal medium, which has the following composition: 47.7 mM $Na_2HPO_4 \cdot 7H_2O$, 21.7 mM $KH_2PO_4$, 8.6 mM NaCl, 18.7 mM $NH_4Cl$, 1 mM $MgSO_4$, 0.2% (w/v) glucose, and 0.5% (w/v) casamino acids (CAA). [40, 5] This medium was then supplemented with 0.1 mM $CaCl_2$, as recommended in other recipes for M9 minimal medium. Further medium optimization revealed that additional carbon sources (succinate, citrate, and glutamate) [44] at 0.2% (w/v) and 0.4% L-arginine (L-Arg) [45-47] were necessary to induce the formation of SA versus Int *P. aeruginosa* biofilms. The final composition of M9+ media contained 47.7 mM $Na_2HPO_4$, 21.7 mM $KH_2PO_4$, 8.6 mM NaCl, 18.7 mM $NH_4Cl$, 1 mM $MgSO_4$, 0.1 mM $CaCl_2$, 0.4% L-Arg, 0.5% CAA, 0.2% anhydrous α-D(+)-glucose, 0.2% sodium succinate dibasic hexahydrate, 0.2% citric acid monohydrate, and 0.2% L-glutamic acid monopotassium salt monohydrate.

Studies have shown Fe to be both essential and strictly regulated in *P. aeruginosa* biofilms. [10, 48-53] However, the present work found that addition of Fe salts proved problematic due to their ability to oxidize to insoluble forms and to precipitate with phosphates, even at room temperature or with low phosphate medias (e.g., in MM9, a M9 variant with a reduced phosphate concentration and an alternative buffer such as Tris). [54] Finally, a 95:5 mixture of M9+ media:LB media (mixed during inoculum preparation) yielded the greatest QS-dependence and reproducibility of SA biofilm growth, and was used in all assays in this study.

M9+ medium was prepared by combining components from separate stock solutions with the exception of L-Arg and CAA, which were added from solid stock upon each preparation. M9 buffer (47.7 mM $Na_2HPO_4$, 21.7 mM $KH_2PO_4$, 8.6 mM NaCl, and 18.7 mM $NH_4Cl$) was added from a 10× stock. Sugars (glucose, succinate, citrate, and glutamate) were added from filter sterilized 10% (w/v) stocks. $MgSO_4$ was added from a 200 mM stock, and $CaCl_2$ was added from a 20 mM stock.

Phosphate buffered saline (PBS; 10 mM $Na_2HPO_4$, 1.76 mM $KH_2PO_4$, 137 mM NaCl, and 2.7 mM KCl in 18 MΩ $H_2O$, pH 7.35) used for "washing" steps in microtiter plate biofilm assay was prepared by diluting 10-fold a 10×PBS stock. The CV solution used to stain *P. aeruginosa* biofilms was 0.1% (w/v) CV in 95:5 18 MΩ H$_2$O:EtOH and was prepared by diluting 10-fold a 1% CV in 18 MΩ stock.

Super Optimal broth with Catabolite repression (SOC medium) used to recover transformed cells after electroporation was prepared using the following recipe: 0.5% (w/v) yeast extract, 2% (w/v) tryptone, 10 mM NaCl, 2.5 mM KCl, 10 mM MgCl$_2$, 10 mM MgSO$_4$, and 20 mM glucose. Vogel-Bonner (VB) medium E used for *P. aeruginosa* selection was prepared as reported by Vogel et al. (0.811 mM MgSO$_4$, 9.52 mM citric acid, 57.4 mM K$_2$HPO$_4$, and 8.37 mM NaNH$_4$HPO$_4$). [55]

The mixture utilized for PCR was prepared in 18 MΩ H$_2$O to the following final concentrations: 0.5 U Phusion® High-Fidelity DNA Polymerase (New England Biolabs; NEB), 1× Phusion® HF buffer (NEB), 10 mM dNTPs (deoxyNucleoside TriPhosphates; NEB), and 0.5 µM primers Tn7-GlmS and Tn7R109 (Integrated DNA Technologies). PCR DNA products were analyzed by gel electrophoresis using agarose gels composed of 1% agarose and 1 µg/mL ethidium bromide in 1×TAE buffer (40 mM Tris base, 20 mM acetic acid, and 1 mM EDTA; pH 8.0). Electrophoresis samples were prepared in 6× loading buffer composed of 50% glycerol, 50 mM EDTA, and 0.05% bromophenol blue in 18 MΩ H$_2$O.

D. Crystal Violet Static Biofilm Assay Protocol.

A modified version of the widely used crystal violet (CV) microtiter plate biofilm assay, first described by Christensen et al. [56] and later popularized by O'Toole et al., [57] was used in this study and is described in detail below. [45]

Compounds to be evaluated for biofilm modulatory activity were added to the assay microtiter plates by means of a "solvent evaporation" delivery. This delivery method involves preparation of compound stock solutions, addition of stocks to microtiter plates at appropriate volumes to obtain target molar quantities per well, evaporation of the solvent, and re-solubilization of the compound in the final assay medium upon inoculum addition. This delivery method was adopted to avoid the biofilm inhibitory effects observed with an "organic solvent-to-solution" delivery method (e.g., DMSO-to-media; data not shown), which is more commonly done in small molecule screens. EtOH was chosen as the solvent for solvent evaporation delivery in this study based on the chemical resistance limitations of polystyrene microtiter plates. Prior to each experiment, EtOH stock solutions of compounds being evaluated were prepared, diluted, and added to microtiter plates at varied volumes to obtain a target final concentration per well upon inoculum addition. Plates were incubated at 37° C. to evaporate EtOH and sterilized in a Baker SterilGARD III Advance Biological Safety Cabinet by UV-C germicidal irradiation for 30 min (lids removed). [58] EtOH only was added to wells designated as "no compound" positive controls (Pos. Con.) and "no bacteria" negative controls (note, controls lacking bacteria yielded no significant staining in the CV assay (data not shown)). The outer wells were never used for test samples as evaporation and significant deviations in growth were observed; thus, outer wells were filled with sterile 18 MΩ H$_2$O to minimize these effects.

Bacterial samples for biofilm assessment were prepared by first streaking a freezer stock of *P. aeruginosa* PAO1 on an LB/agar plate and incubating at 37° C. for ~16 h. Single colonies were selected and used to inoculate LB medium (10 mL) in a 25 mL Erlenmeyer flask. The culture was grown on an incubator-shaker (200 rpm) at 37° C. for ~16 h to an OD$_{600}$ of ~1.0. Overnight cultures were gently decanted into falcon tubes to minimize transfer of biofilm produced during overnight growth. An inoculating culture was prepared by centrifuging an aliquot of overnight culture at 3,000 rpm for 10 min, removal of the supernatant, and then re-suspending the pellet in 95:5 M9+:LB at 10-fold the initial volume (effecting a 1-in-10 dilution; OD$_{600}$ ~0.1-0.2). Using a multi-channel pipette, this culture was added to test microtiter plates in 200 µL aliquots. The well contents were mixed using a 10 µL multi-channel pipette in a swirling motion; insoluble compound samples were noted and later excluded from the data set as needed.

Plates were covered with the provided lid and incubated statically at 37° C. for 12-24 h. Maximal biofilm formation is obtained at 24 h, after which the amount of biofilm declines unless fresh nutrients are provided. After incubation, the OD$_{600}$ was measured, and the bacterial suspension was removed by inverting and shaking the plate over a waste pan and then taping on a paper towel (process termed "dumping"). Non-biofilm associated biomaterial was removed by adding 225 µL PBS and dumping (process termed "washing") and then repeating this washing process. Biofilm was fixed to the microtiter plates by uncovering the plate and thermally dehydrating at 37° C. [45] Optimization studies demonstrated that fixing was essential and thermal dehydration at 37° C. was more effective than common chemical fixative methods (e.g., Bouin's fixative, glutaraldehyde, EtOH dehydration, or Carnoy's fixative; data not shown).

Dried biofilm was stained for 15 min at room temperature with a 200-µL aliquot of the CV staining solution. After 15 min, the stain was removed by dumping, and residual stain was removed by washing 1× with 200 µL PBS and 2× with 200 µL 18 MΩ H$_2$O. The plates were dried uncovered at 37° C., after which the plates were imaged with a digital camera on a white light trans-illuminator. The amount of CV retained by the biofilm was quantified by re-solubilizing the CV with 30% AcOH (process termed "de-staining") and measuring the absorbance at 590 nm; this value then directly correlates to the amount of biofilm in the well. [10] Optimization studies demonstrated that 30% AcOH was the most effective at re-solubilizing CV relative to other commonly used solvents (e.g., EtOH), and ~590 nm was the wavelength of maximal absorption (data not shown).

De-staining was completed in two steps in order to differentiate the amount of SA biofilm from the amount of Int biofilm. First, SA biofilm was quantified by adding 100 µL 30% AcOH, re-solubilizing by gentle pipetting, and then measuring the A590(SA). Second, the Int biofilm was quantified by removal of the first aliquot of AcOH via pipette, adding a second aliquot of 225 µL 30% AcOH, re-solubilizing the Int biofilm using a polypropylene 96-pin replicator (V&P Scientific) in a swirling motion, and then measuring the A590(Int). Pin replicators only transfer ~130 mL solvent, so the amount of sample loss during mixing is negligible. The Ttl biofilm was later calculated by summation of the A590 values of the SA and the Int biofilms; this summation is valid regardless of the difference in de-stain solvent volumes due to the fact that the difference in concentration is offset by an equivalent difference in path length. The final absorbance readings were corrected by subtracting the blank absorbance of the solvent and reported as a percent of the "no compound" positive control.

Example 3: Results of *P. aeruginosa* Biofilm Assay (Compounds 1, 2, and 4-24)

Figure 2:
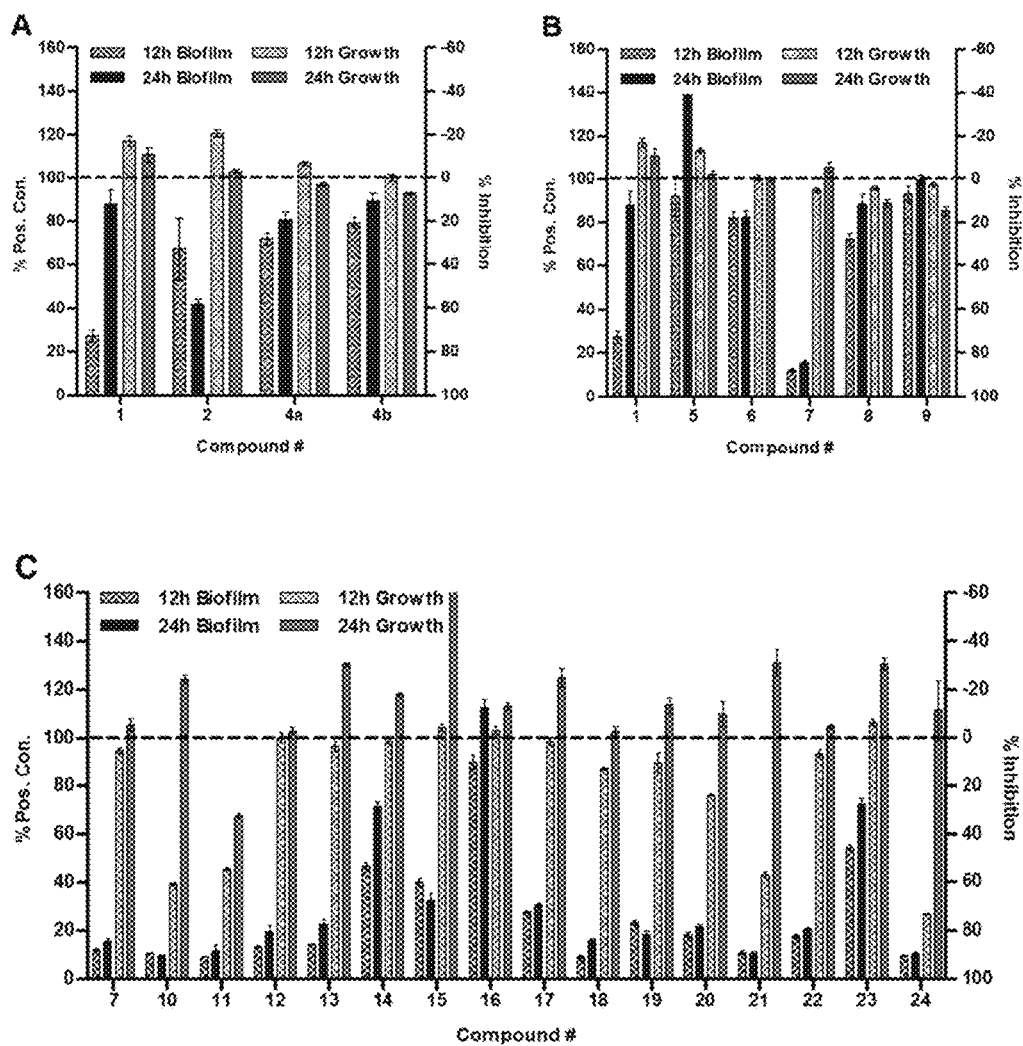
FIG. 2A-C illustrates *P. aeruginosa* microtiter plate biofilm assay data (bar graphs) for (A) compound 1, 2 and 4, (B) compounds 5-9 and compounds 10-24 at 500 microM.

Compounds were initially assessed for their *P. aeruginosa* biofilm modulatory activity at 500 µM using the CV assay described above. Test plates were prepared by making 1 mM EtOH stock solutions and adding 100 μL aliquots to the wells of 96-well microtiter plates. All compounds were tested in replicates of 6 wells and were assessed after 12 and 24 h of incubation. The assay data for compounds 1, 2, and 4-24 are shown in FIG. 2A-C.

Figure 3:
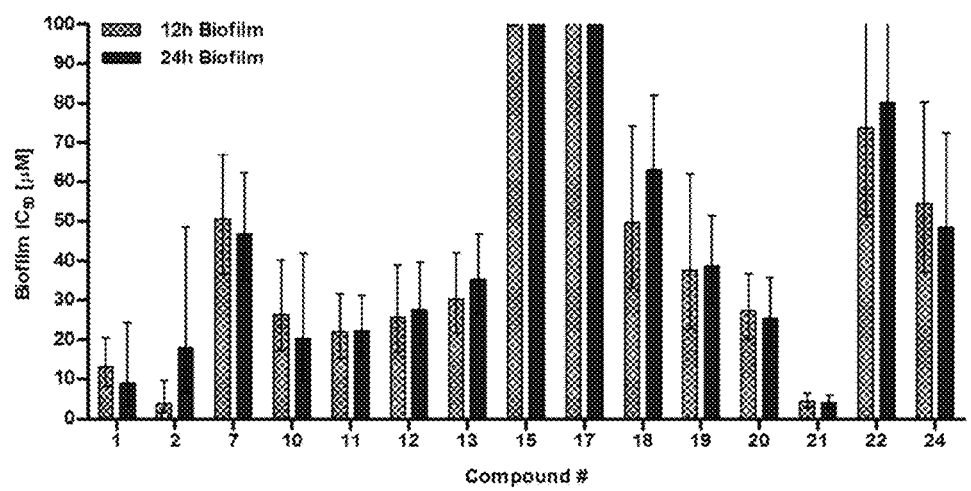
FIG. 3 is a graph of $IC_{50}$ values for selected compounds in the crystal violet *P. aeruginosa* biofilm assay. Error bars represent 95% CI.

Example 4: Dose-Response Analysis of Compounds on *P. aeruginosa* Biofilm Formation Compounds demonstrating significant biofilm inhibitory activity (>60%) in initial assays at 500 μM were submitted to dose-response analysis using an analogous CV biofilm assay. Compound stock solutions in EtOH were prepared at 5 mM and diluted in a 1-in-10 series to obtain additional EtOH stocks at 500, 50, 5, 0.5, and 0.05 μM. Stocks were added to 96-well microtiter plates in 126.5 or 40 μL aliquots to obtain a range of final concentrations that step from a half to a full order of magnitude between concentrations, respectively. The final well concentrations upon inoculum addition were as follows: $10^x$ μM where x=3.5, 3, 2.5, 2, 1.5, 1, 0, −1, or −2. All compounds were tested in replicates of 3 wells and were assessed after 12 and 24 h incubation. $IC_{50}$ values were calculated using a sigmoidal curve fit (three parameters) and are reported with a 95% CI. The assay results are summarized in Table 2 and FIG. 3. Dose-response curves and corresponding sigmoidal curve fits are not shown [see 64].

TABLE 2

$IC_{50}$ values for selected compounds in the CV *P. aeruginosa* biofilm assay.

| Compound | 12 h biofilm $IC_{50}$ [μM] | 95% CI [μM] | 24 h biofilm $IC_{50}$ [μM] | 95% CI [μM] |
|---|---|---|---|---|
| 1 | 13.0 | 8.2-20.5 | 8.9 | 3.3-24.4 |
| 2 | 3.8 | 1.5-9.7 | 18.0 | 6.6-48.6 |
| 7 | 50.5 | 36.8-67.0 | 46.8 | 35.1-62.4 |
| 10 | 26.3 | 17.2-40.2 | 20.3 | 9.8-41.9 |
| 11 | 22.0 | 15.4-31.6 | 22.2 | 15.8-31.3 |
| 12 | 25.7 | 17.0-38.9 | 27.5 | 19.1-39.7 |
| 13 | 30.2 | 21.7-42.0 | 35.2 | 26.6-46.7 |
| 15 | 186.0 | 99.8-346.8 | 139.3 | 106.8-181.7 |
| 17 | 199.4 | 130.9-303.6 | 175.2 | 116.8-262.7 |
| 18 | 49.6 | 33.1-74.3 | 63.1 | 48.4-82.2 |
| 19 | 37.6 | 22.8-62.0 | 38.7 | 29.1-51.4 |
| 20 | 27.3 | 20.2-36.8 | 25.4 | 18.0-35.8 |
| 21 | 4.3 | 2.8-6.5 | 4.0 | 2.7-5.9 |
| 22 | 73.8 | 51.2-106.5 | 80.1 | 62.9-102.2 |
| 24 | 54.5 | 37.0-80.4 | 48.3 | 32.2-72.5 |

Example 5: *P. aeruginosa* Biofilm Dispersion Assay Protocol and Dose-Response Analysis for 7 and 21 on Biofilm Dispersion Compounds 7 and 21 were evaluated for their ability to disperse preformed *P. aeruginosa* biofilms. For biofilm dispersion assessment, the static CV biofilm assay described above was modified in order to introduce compound to preformed biofilm for an additional incubation period. Solvent evaporation delivery of compound was not possible in this format; thus, stock solutions of compounds 7 and 21 were prepared in 95:5 M9+:LB media. Stocks of 7 and 21 were prepared at 3.16 mM and 1 mM, respectively (21 was insoluble at 3.16 mM). These stocks were diluted in series to obtain final concentrations as follows: $10^x$ μM where x=3.5 (7 only), 3, 2.5, 2, 1.5 (21 only), 1, 0, −1, or −2. Biofilms were allowed to form in microtiter plates in the absence of compound for 24 h, after which non-biofilm material was removed by dumping and washing as normal with sterile PBS. After the second washing, 200 μL of fresh 95:5 M9+:LB media containing compound at various concentrations was added to the wells, and the plates were incubated at 37° C. for an additional 24 h. One set of wells was left empty in order to assess the amount of biofilm present after the first 24 h incubation, while another set of wells was given media without compound to assess the amount of biofilm at 48 h. We observed similar amounts of biofilm after 48 h as after 24 h, suggesting that a maximal amount of biofilm is reached by 24 h and maintained with media replacement. After the second 24 h incubation, non-biofilm material was removed by dumping and washing 4× with PBS (the additional washing at 48 h was found necessary to completely remove detached Int biofilm that had settled over the SA biofilm; data not shown). Biofilm was fixed and quantified with CV as described above. The amount of dispersed biofilm was determined via comparison of the amount of biofilm at 48 h in the presence of compound versus the amount of biofilm in the "no compound" positive control at 24 h. A higher degree of error was often observed with this assay format due to the additional incubation and washing steps; thus, all compounds were tested in replicates of 6 wells.

Figure 4:
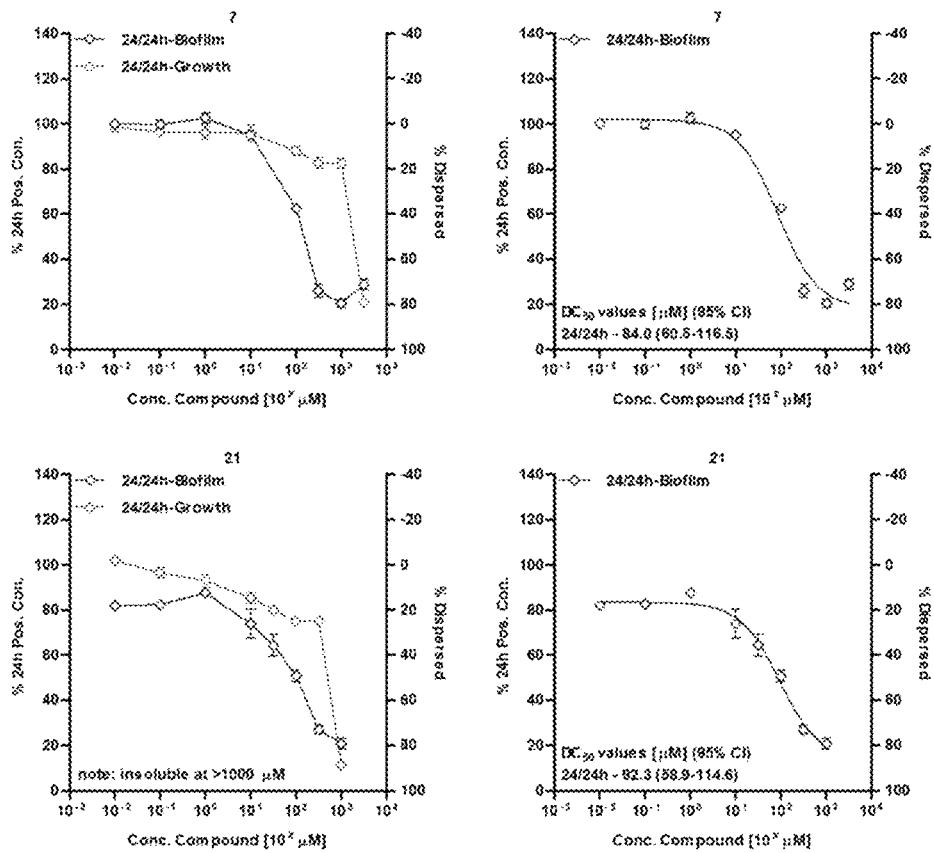
FIG. 4 illustrates *P. aeruginosa* biofilm dispersion and bacterial growth dose-response curves (left) and sigmoidal curve fits with DC50 values (right) for biofilm dispersion for compounds 7 (top) and 21 (bottom).

$DC_{50}$ values for biofilm dispersion by 7 and 21 were calculated using a sigmoidal curve fit (three parameters) and are reported with a 95% CI. The results are presented in FIG. 4, which shows that both 7 and 21 are able to disperse preformed biofilm up to ~80% without significantly affecting the final $OD_{600}$ measurement.

Figure 5:
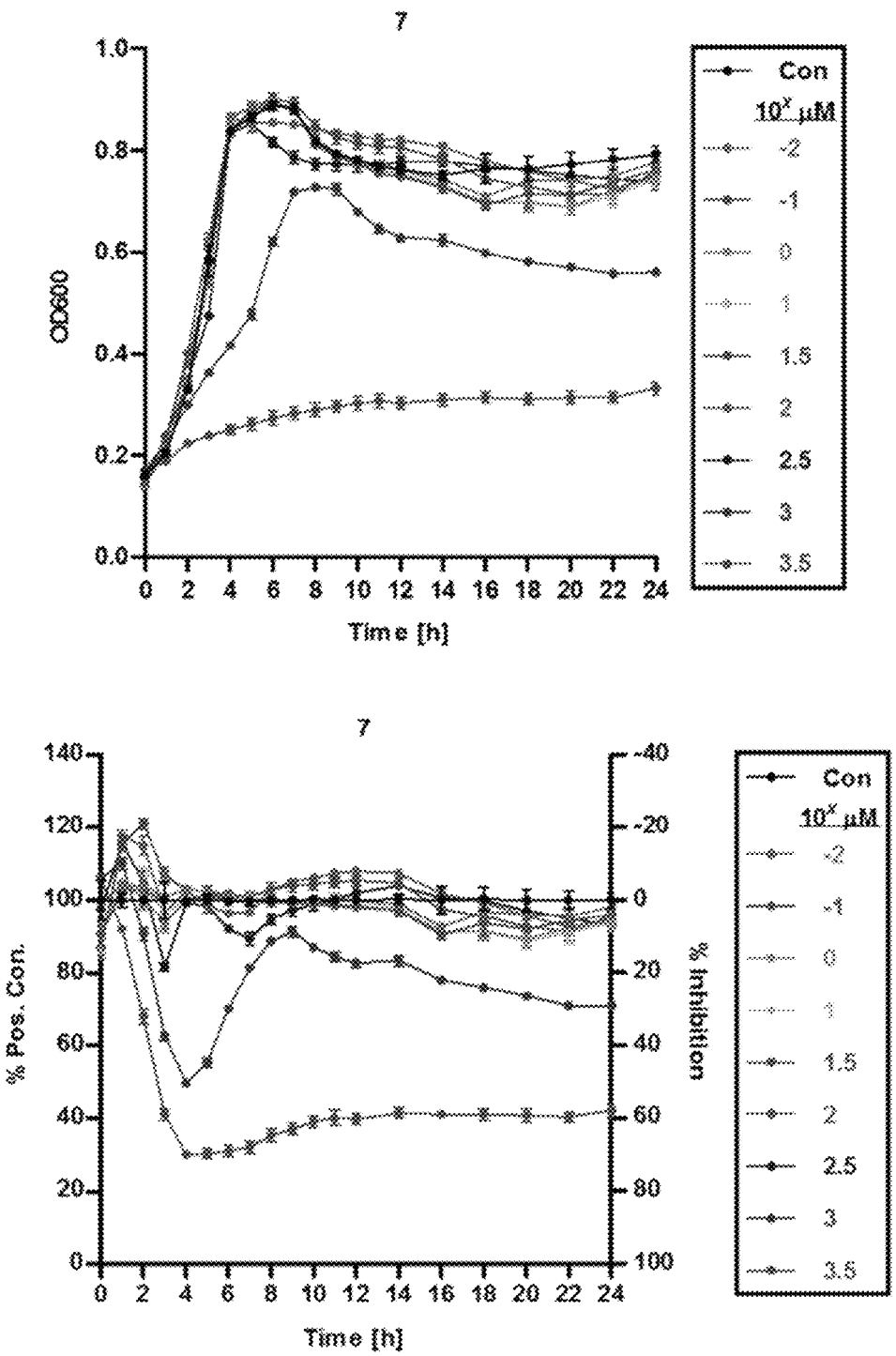
FIG. 5 illustrates *P. aeruginosa* growth curves in the presence of compound 7, where Con=positive control (no compound).
Figure 6:
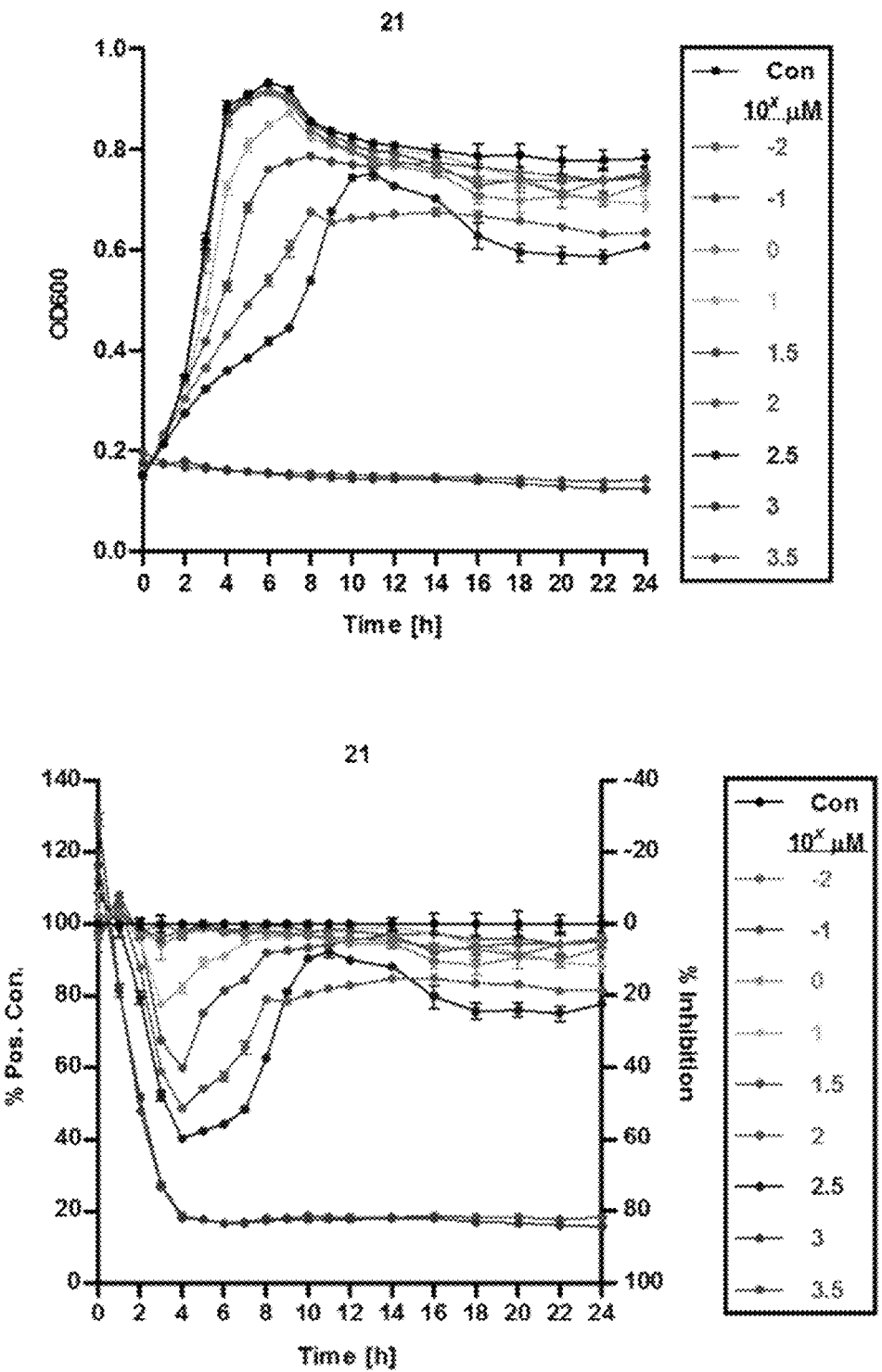
FIG. 6 illustrates *P. aeruginosa* growth curves in the presence of compound 21, where Con=positive control (no compound).

Example 6: Bacterial Growth Effects—Effects of Compounds 7 and 21 on *P. aeruginosa* Growth Over Time The effects of compounds 7 and 21 on *P. aeruginosa* growth were evaluated by monitoring the $OD_{600}$ as a function of time. Microtiter plates were prepared similar to biofilm dose-response analyses such that final well concentrations upon inoculum addition ranged from $10^x$ μM where x=3.5, 3, 2.5, 2, 1.5, 1, 0, −1, or −2. Compounds 7 and 21 were tested in replicates of 3 wells, and the $OD_{600}$ was measured every 1-2 h for 24 h. The results are shown in FIGS. 5 and 6, respectively.

With the exception of very high compound concentrations (1000 μM and higher), the growth curves show that there are minimal deviations from the positive control (less than 20% inhibition) in the presence of 7 or after 12 h in the presence of 21. Prior to 12 h, we do observe deviations of greater than 20% inhibition in the presence of 21 at concentrations as low as 10 μM, but these diminish by 12 h. Biofilm inhibition $IC_{50}$ values of 7 and 21 (47 and 4 μM respectively) are within the concentration ranges that show minimal deviations in growth, which suggests biofilm inhibition is not simply due to growth inhibition.

Example 7: Effect on Protein Synthesis

A. Preparation of *P. aeruginosa* Strain PAO1 Gen-Gfp.

Compounds 7 and 21 were tested for their effect on general protein synthesis in *P. aeruginosa*. In these assays a *P. aeruginosa* strain that constitutively produced GFP was employed. Hentzer et al. pursued a similar strategy to ascertain whether a halogenated furanone targeted the las QS system in *P. aeruginosa* specifically or simply inhibited general protein synthesis. [59]

The constitutively-expressing genomic (gen)-GFP strain, PAO1 gen-gfp, was prepared using the mini-Tn7 transposon system reported by Lambertsen et al. and Koch et al. to introduce the Tn7 element miniTn7-gfp2 into the neutral chromosomal site attTn7 in the PAO1 genome. [41,42] The Tn7 element miniTn7-gfp2 was chosen for these studies because it encodes for the same GFP variant, GFPmut3b, used in our QS reporters, discussed herein below. However, rather than being an unstable GFP under the control of the lasII or rhlI QS-dependent promoter as in the QS reporters, GFP is stable and under the control of the constitutive E. coli lac-promoter derivative $P_{A1/O4/O3}$. The use of this strain allows a comparison of QS-dependent and non-QS-dependent gene expression in the presence of 7 and 21.

Preparation of P. aeruginosa PAO1 gen-gfp.

The mini-Tn7 transposon delivery plasmid carrying the Tn7 element and the helper plasmid carrying the transposase genes were introduced into P. aeruginosa via mobilization by means of a four-parental mating. [41] The four strains in this mating were the recipient strain P. aeruginosa PAO1, the delivery strain E. coli XL1-Blue/pBKminiTn7-gfp2, the transposase helper strain E. coli SM10::λpir/pUX-BF13, and the conjugation helper strain E. coli HB101/pRK600 that is able to mobilize the other plasmids using the RP4/RK2 conjugation system. [41, 42] In brief, overnight cultures of each strain were prepared and sub-cultured in LB media with appropriate antibiotic (100 μg/mL ampicillin for pBKminiTn7-gfp2 and pUX-BF13, and 6 μg/mL chloramphenicol for pRK600). Samples of each sub-culture were mixed in a single spot on a sterile 0.22 μm hydrophilic PVDF filter (Millipore Durapore®) on an LB/agar plate and allowed to incubate for 24 h. The bacteria were then re-suspended in PBS, plated on VB/agar with 60 μg/mL gentamicin (Gm), and incubated at 37° C. overnight to select for PAO1 with the Tn7 insertion. Isolated colonies were used to grow overnights in LB medium plus 15 μg/mL Gm, from which final freezer stocks were prepared.

Isolated colonies were subjected to PCR using the unique set of Tn7 primers described by Lambertsen et al. to confirm the mini-Tn7 insertion. [41] The specific primers were the forward primer Tn7-GlmS (5'-AATCTGGCCAAGTCGGT-GAC-3') that anneals near the left end of the Tn7 insertion, and the reverse primer Tn7R109 (5'-CAGCATAACTG-GACTGATTTCAG-3') that anneals to the right end of the Tn7 insertion. Analysis of the PCR products by agarose gel electrophoresis indicated the presence of the expected 100-150 by fragment that confirms the mini-Tn7 genomic insertion (data not shown).

B. Growth, Biofilm, and Fluorescence Assays of P. aeruginosa PAO1 Gen-Gfp

Figure 7A:
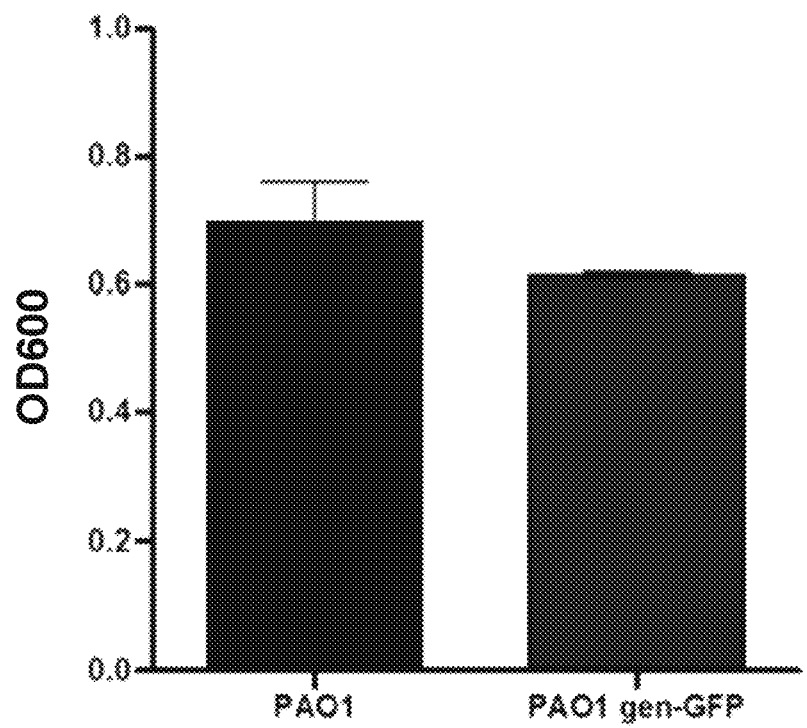
FIGS. 7A-7C illustrate a comparison of *P. aeruginosa* PAO1 and PAO1 gen-gfp growth (FIG. 7A), biofilm (FIG. 7B), and fluorescence (FIG. 7C) at 24 h.
Figure 7B:
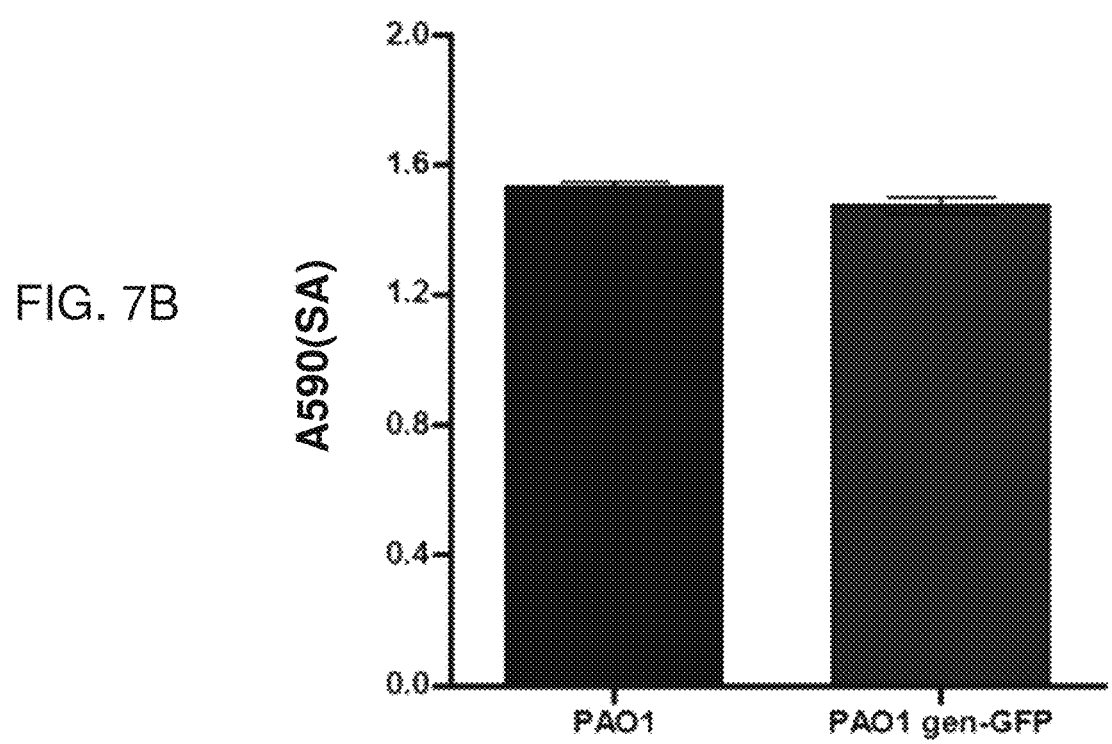
Figure 7C:
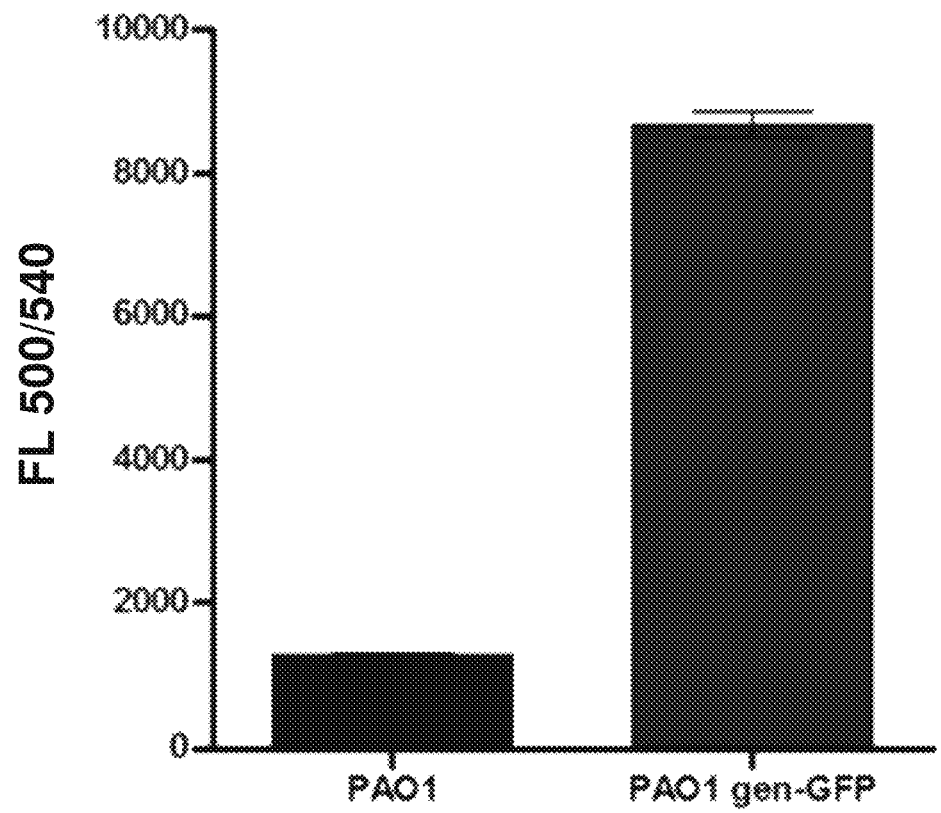

Compared to P. aeruginosa PAO1, P. aeruginosa PAO1 gen-gfp was expected to display similar growth and biofilm formation characteristics, yet exhibit significantly enhanced fluorescence. Using the same conditions as the static biofilm assay, bacterial growth, biofilm formation, and fluorescence of PAO1 gen-gfp at 24 h was assessed by measuring the $OD_{600}$, A590(SA), and FL500/540 respectively. Samples were tested in replicates of 3 wells, and the averaged data and STE are reported. The results are shown in FIGS. 7A-7C and demonstrate that P. aeruginosa PAO1 gen-gfp grows and produces biofilm similarly to PAO1, yet displays stronger fluorescence at 500/540 nm, as expected.

C. Dose-Response of 7 and 21 on GFP Production in P. aeruginosa PAO1 Gen-Gfp.

Figure 8:
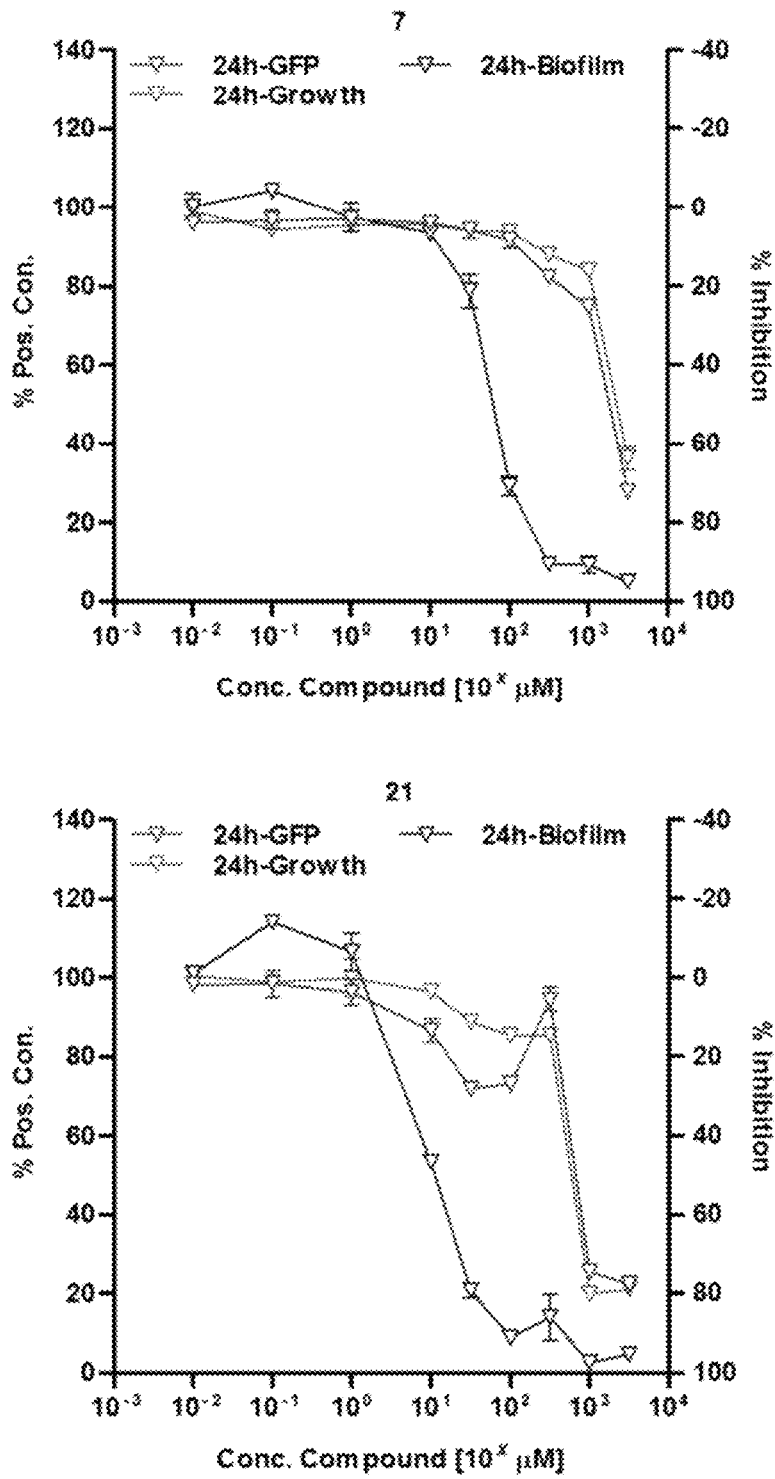
FIG. 8 illustrates *P. aeruginosa* PAO1 gen-gfp dose-response of compounds 7 (top) and 21 (bottom) at 24 h.

Compounds 7 and 21 were evaluated for their ability to affect constitutive GFP production in the P. aeruginosa PAO1 gen-gfp strain using the static biofilm assay conditions described above. Microtiter plates were prepared similar to biofilm dose-response analysis such that final well concentrations upon inoculum addition ranged from $10^x$ μM where x=−3.5, −3, −2.5, −2, −1.5, −1, 0, −1, or −2. Measurements of FL500/540 and $OD_{600}$ were made at 24 h, after which the samples were evaluated for biofilm formation using the CV procedure. Samples were tested in replicates of 3 wells, and the averaged data and STE are reported. The results are shown in FIG. 8. The fluorescence dose curves indicate that both 7 and 21 only inhibit the production of GFP at concentrations where bacterial growth is also inhibited, which indicates that biofilm inhibition is not due to inhibition of overall protein synthesis.

Example 8: Analysis of the Effects of Metals on Biofilm Inhibition

UV-Vis metal binding studies provided preliminary evidence that compound 7 is able to interact with certain metals (i.e., Cu(II), Fe(II), Fe(III), and Zn(II)) when combined at compound:metal ratios of approximately 1:1 (data not shown). The mechanism of P. aeruginosa biofilm inhibition by 7 could be due to metal sequestration. Recent work by Rogers et al. supports such a hypothesis, as they showed that a related 2-ABI analog (2-(2-amino-1H-benzo[d]imidazol-5-ylcarbamoyl)-3,4,5,6-tetrachlorobenzoic acid hydrochloride) was able to inhibit and disperse Gram-positive bacterial biofilms through a zinc-dependent mechanism. [22] Rogers et al. performed NMR metal binding studies that demonstrated that the $^1$H NMR spectrum of the 2-ABI analog was affected by the presence of Zn(II), suggesting an interaction between the 2-ABI and Zn(II) (compound:metal ratio not reported). More notably, the authors reported that the biofilm inhibitory activity of the 2-ABI analog was mitigated in a dose-dependent manner by the addition of $ZnCl_2$. The authors also reported that they did not observe diminished biofilm inhibitory activity of the 2-ABI analog by $FeSO_4$. Possible mitigating effects of metals on the inhibitory effect of compound 7 on P. aeruginosa biofilm growth was thus assessed. Our assay method is described in detail below.

Microtiter plates were first prepared by adding 50 μL aliquots of a 1 mM EtOH stock solution of 7 to each well in order to effect a final well concentration upon inoculum addition of 250 μM; this concentration was chosen as it is approximately the minimum concentration of 7 showing maximal biofilm inhibition. The EtOH was then removed by drying at 37° C., and the plates were sterilized. Directly prior to inoculation, 100 mM stock solutions of metals were freshly prepared in 18 MΩ $H_2O$ and diluted in series in a polypropylene 96-well microtiter plate (Costar 3879) to achieve stocks with the following concentrations: 100, 75, 50, 25, 12.5, 6.25, 1.25, 0.25, 0.05, and 0 mM. The choice of metals for evaluation was based on the results of the UV-Vis studies and included Cu(II)$SO_4$, Fe(II)$SO_4$.7$H_2O$, Fe(III)$Cl_3$.6$H_2O$, and Zn(II)$SO_4$.7$H_2O$. Using a 10 μL multi-channel pipette, 2 μL aliquots of the metal stock solutions were added to the side of wells, avoiding contact with dried 7 on the bottom of the well. Thus, upon addition of 200 μL inoculum and mixing, the metal concentration per well was diluted ~100-fold, resulting in the following final well concentrations and corresponding metal:7 ratios: 1000 (4:1), 750 (3:1), 500 (2:1), 250 (1:1), 125 (1:2), 62.5 (1:4), 12.5 (1:20), 2.5 (1:100), 0.5 (1:500), and 0 μM (0:1). The highest metal:7 ratio obtained was 4:1 (1000 μM metal to 250 μM 7), which was assumed to be sufficient to see any mitigating effect based on our UV-Vis studies. Controls containing metal only were also tested, as certain metals are known to have an effect on biofilm development (e.g., Fe). [19-25] All samples were tested in replicates of 3 wells and were assessed for biofilm production after 24 h incubation by CV staining and quantification.

Figure 9:
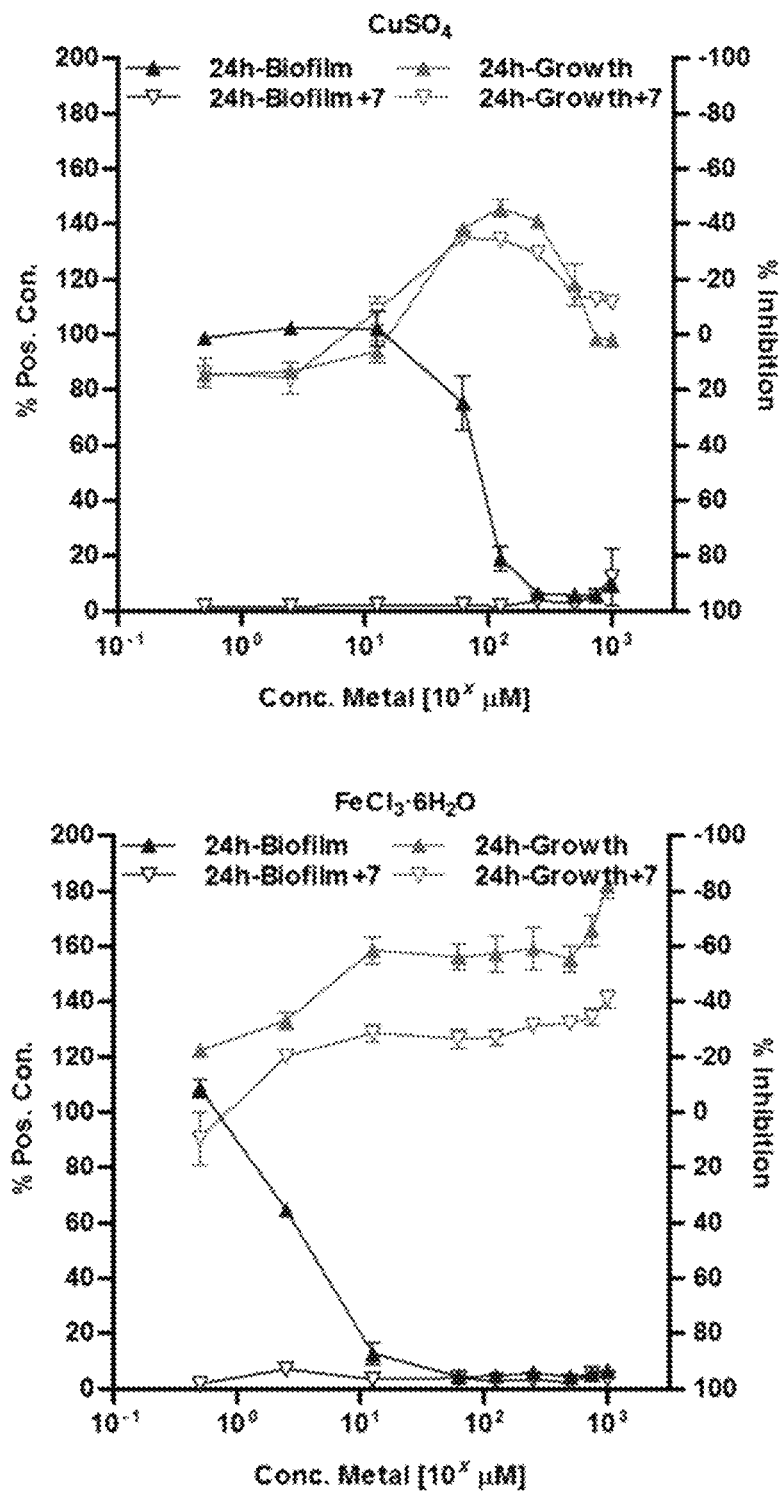
FIG. 9 illustrates *P. aeruginosa* biofilm formation and bacterial growth dose-response curves in the absence or presence of compound 7 (at 250 µM) and in the presence of $CuSO_4$, or $FeCl_3.6H_2O$.
Figure 10:
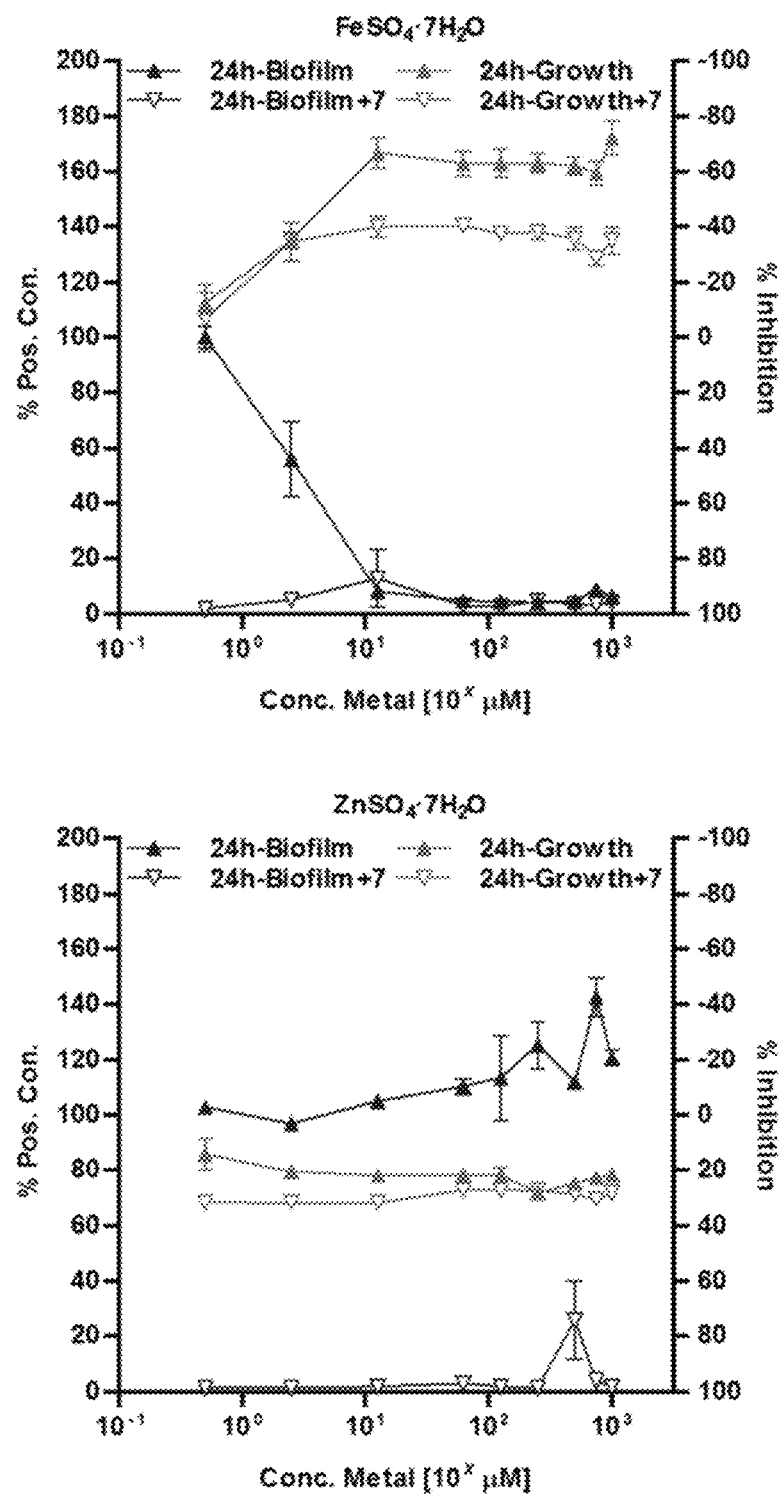
FIG. 10 illustrates *P. aeruginosa* biofilm formation and bacterial growth dose-response curves in the absence or presence of compound 7 (at 250 microM) and in the presence of $FeSO_4.7H_2O$, or $ZnSO_4.7H_2O$.

The results are shown in FIGS. 9 and 10 and demonstrate that none of the tested metals were able to mitigate the biofilm inhibitory activity of compound 7 in *P. aeruginosa*. These data indicate that the mechanism of biofilm inhibition via 7 is not due to metal sequestration. With the exception of Zn(II), the controls containing metal only (i.e., no compound 7) did exhibit some biofilm inhibitory response. Such an inhibitory effect has been reported in a number of studies, at least for Fe [10, 51] and is therefore not an unexpected observation.

Example 9: Effect on Quorum Sensing in *P. aeruginosa*

A. Preparation of *P. aeruginosa* Las and Rhl Reporter Strains.

To evaluate the activity of compounds 7 and 21 on QS in *P. aeruginosa*, we prepared two *P. aeruginosa* QS reporter strains: PAO1/plasI-LVAgfp and PAO1/prhII-LVAgfp. These strains contain the reporter plasmids plasI-LVAgfp and prhII-LVAgfp, respectively, which contain the lasII or rhII promoter sequences fused to LVAgfp. Binding of activated LasR or RhlR to these promoters induces GFP production, which can be quantified by fluorescence and is proportional to the level of LasR or RhlR activation. LVAgfp is an unstable form of GFP with an estimated half-life of 40-60 min, which allows for a more real-time analysis of gene expression (wild-type GFP has a half-life of greater than 1 day). [60] Further, this specific GFP is the variant GFPmut3b that has a shifted excitation maximum near 501 nm (wild-type GFP has an excitation maximum near 395 nm); emission maximum is similar to wild-type GFP at 511 nm (wild-type GFP has emission maximum near 508 nm). [61] Utilizing this GFP variant is key to detection over native fluorescent pigments that are produced in *P. aeruginosa* and excite near 400 nm and emit near 500 nm. [62] Preparation and analysis of the PAO1/plasI-LVAgfp and PAO1/prhII-LVAgfp reporters are outlined below.

Preparation of *P. aeruginosa* PAO1/plasI-LVAgfp and PAO1/prhII-LVAgfp.

QS reporter strains were prepared using the *E. coli* S17-1::λpir mobilizing strain first described by Simon et al. and briefly described here. [43] First, the reporter plasmids were isolated from the strains PAO-JP2/plasI-LVAgfp and PAO-JP2/prhII-LVAgfp by standard alkaline lysis and isopropyl alcohol precipitation. [63] Growth medium throughout plasmid isolation was supplemented with 300 μg/mL carbenicillin (Garb) for plasmid maintenance. Next, the isolated plasmids were transformed into the *E. coli* S17-1::λpir mating strain via standard electroporation methods. [63] The electroporated suspension was recovered in SOC media and plated on LB/agar plates with 300 μg/mL Garb to isolate transformed colonies. Thereafter, the plasmids were mobilized into PAO1 by mating with the *E. coli* 517-1::λpir mating strain carrying the respective plasmid. The mating was performed in a similar manner to that described above for the preparation of PAO1 gen-gfp. In brief, overnight cultures of each strain were prepared in LB (with 100 μg/mL Carb for *E. coli* 517-1::λpir), concentrated, and mixed in a single spot on a 0.22 μm nitrocellulose membrane (Millipore; cut to ~0.5 in diameter circle and autoclaved) on an LB/agar plate. After 24 h incubation, the bacteria were re-suspended in 1×M9 buffer, plated on VB/agar with 100 μg/mL Carb, and incubated overnight to select for PAO1 with the QS reporter plasmids. Isolated colonies were used to grow overnights in LB medium plus 300 μg/mL Carb from which final freezer stocks were prepared.

Growth, Biofilm, and Fluorescence Assays of *P. aeruginosa* PAO1/plasI-LVAgfp and PAO1/prhII-LVAgfp.

Figure 11:
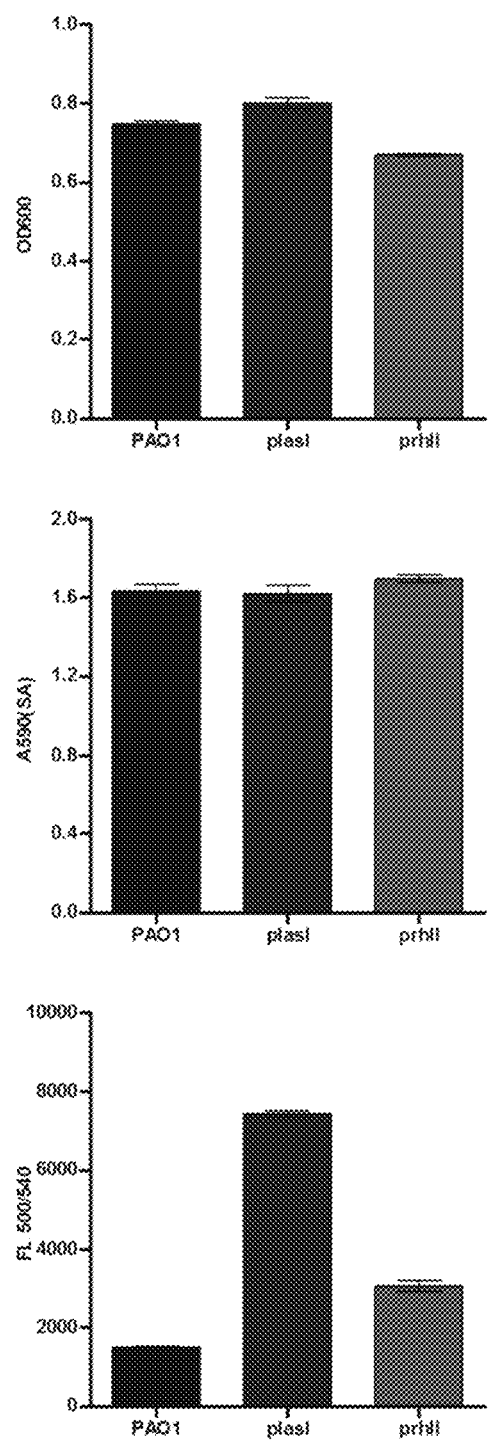
FIG. 11 illustrates *P. aeruginosa* PAO1, PAO1/plasI-LVAgfp and PAO1/prhII-LVAgfp growth (top), biofilm (center), and fluorescence (bottom) at 24 h.
Figure 12:
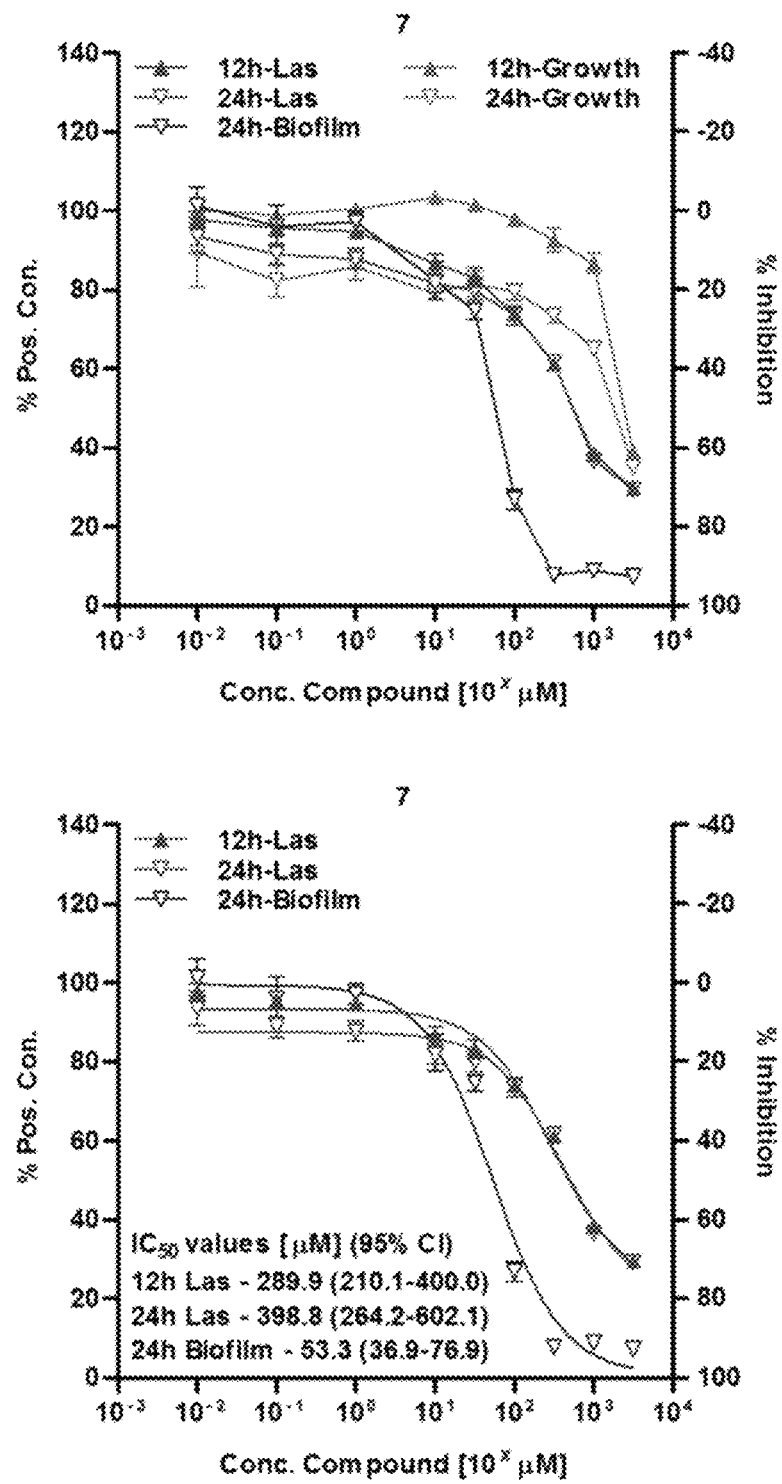
FIG. 12 illustrates *P. aeruginosa* PAO1/plasI-LVAgfp Las inhibition, biofilm inhibition, and bacterial growth dose-response curves (top) and sigmoidal curve fits with $IC_{50}$ values (bottom) for compound 7.
Figure 13:
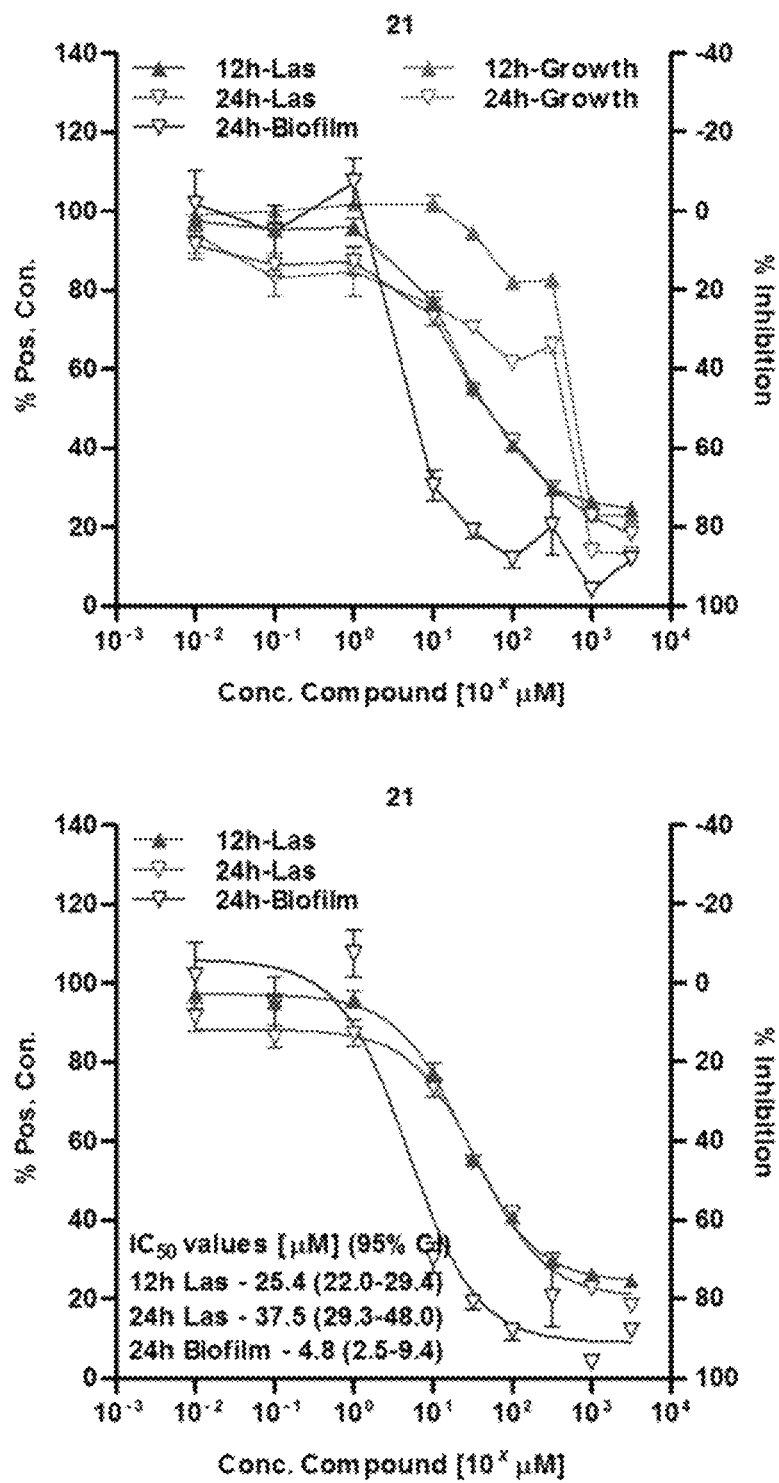
FIG. 13 illustrates *P. aeruginosa* PAO1/plasI-LVAgfp Las inhibition, biofilm inhibition, and bacterial growth dose-response curves (top) and sigmoidal curve fits with $IC_{50}$ values (bottom) for compound 21.
Figure 14:
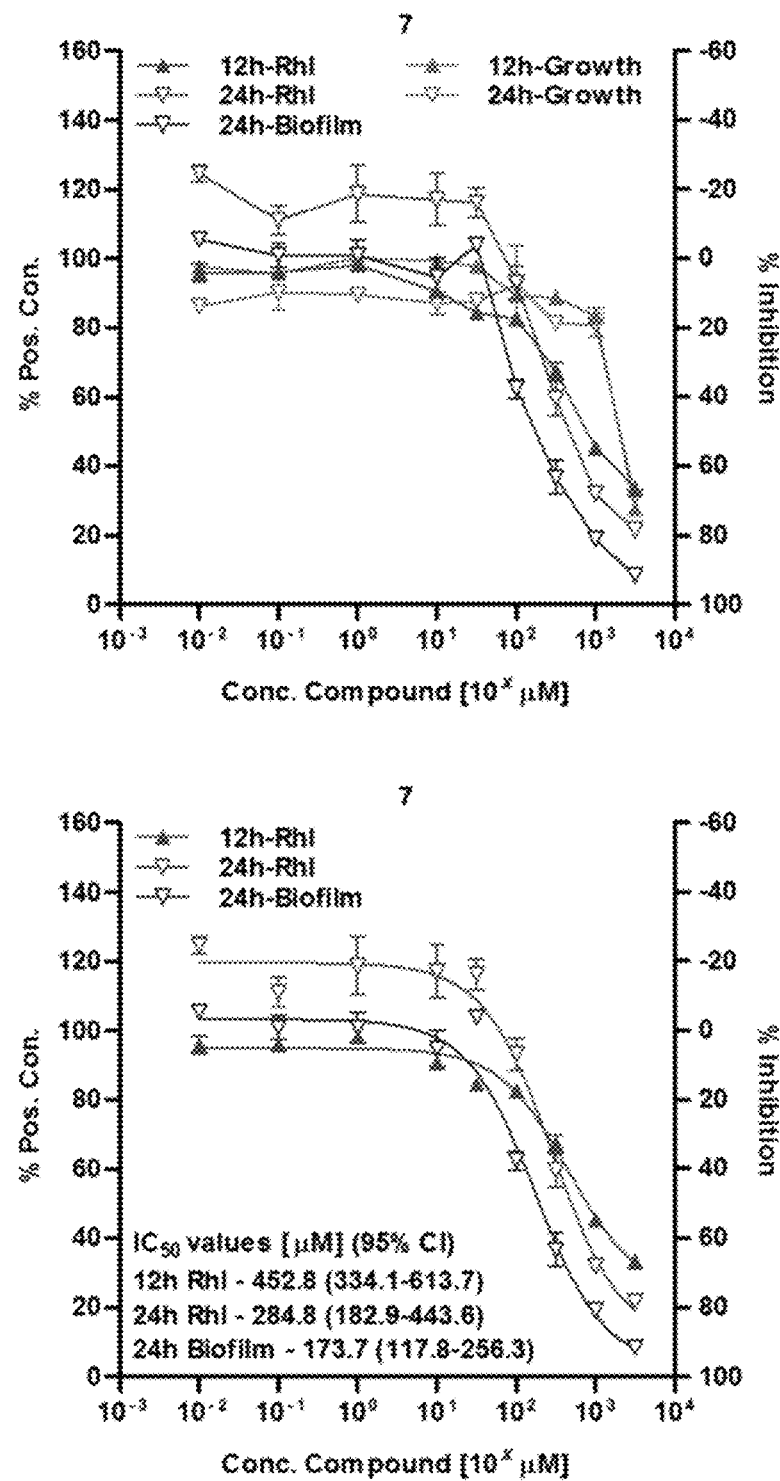
FIG. 14 illustrates *P. aeruginosa* PAO1/prhII-LVAgfp Rhl inhibition, biofilm inhibition, and bacterial growth dose-response curves (top) and sigmoidal curve fits with $IC_{50}$ values (bottom) for compound 7.
Figure 15:
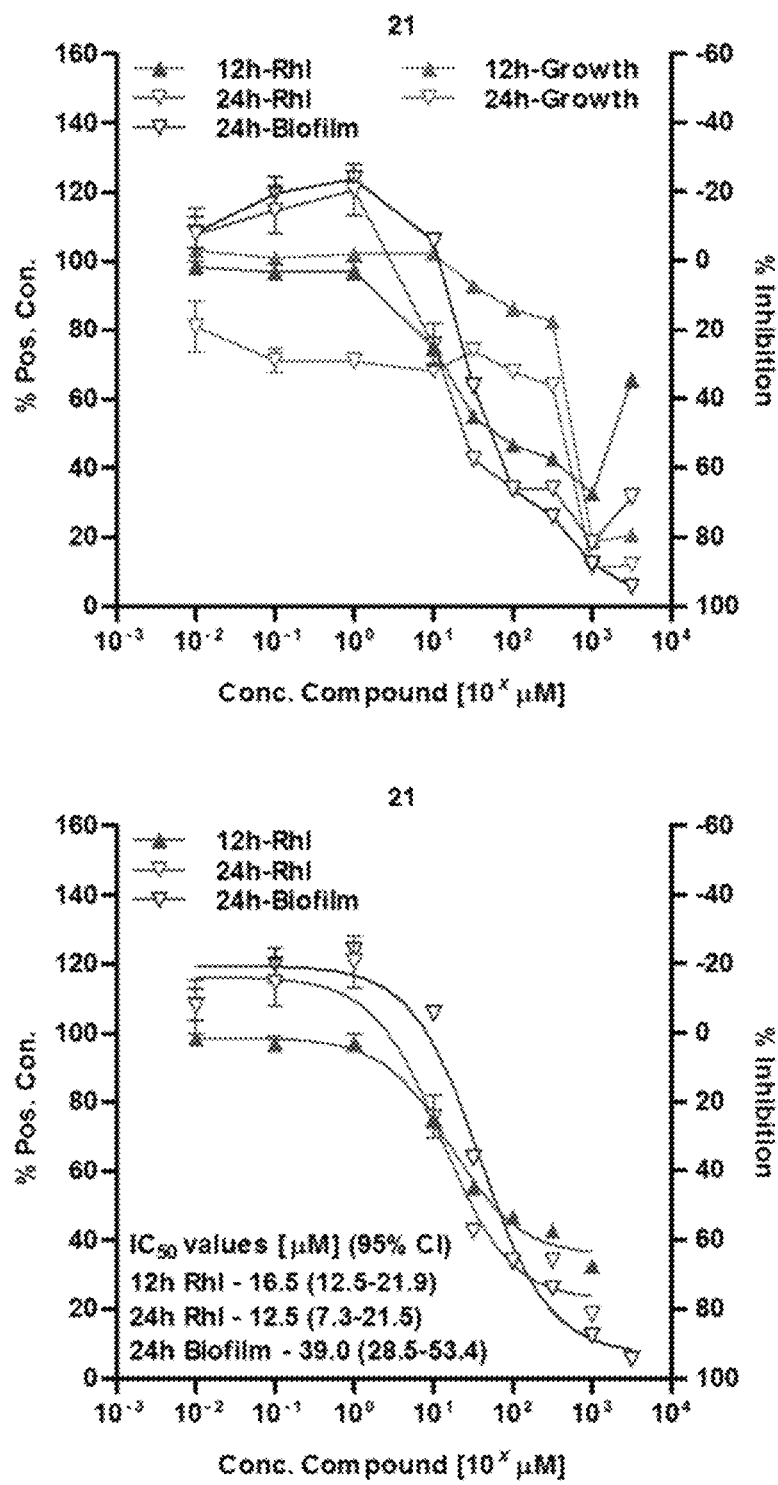
FIG. 15 illustrates *P. aeruginosa* PAO1/prhII-LVAgfp Rhl inhibition, biofilm inhibition, and bacterial growth dose-response curves (top) and sigmoidal curve fits with $IC_{50}$ values (bottom) for compound 21.

Compared to PAO1, the reporter strains were expected to display similar growth and biofilm formation characteristics, yet exhibit significantly enhanced fluorescence. Using the same conditions as the static biofilm assay (with the exception that freezer stocks were streaked on LB/agar with 300 μg/mL Carb), bacterial growth, biofilm formation, and fluorescence of the reporter strains was assessed at 24 h by measuring the $OD_{600}$, A590(SA), and FL500/540 respectively. Antibiotics were not used in the overnight or inoculation cultures due to their observed modest inhibitory effects on growth and biofilm formation. Samples were tested in replicates of 3 wells and the average and STE are reported. The results are shown in FIG. 11 and demonstrate that the two reporter strains grow and produce biofilm similarly to PAO1, yet as expected display greater fluorescence at 500/540 nm (albeit at lower levels in the case of PAO1/prhII-LVAgfpl). In time-dependent growth studies, the rhII reporter showed a slight deviation in growth from PAO1 before 12 h, suggesting that the presence of an additional rhII promoter may disrupt normal growth (data not shown).

B. Dose-Response of 7 and 21 on *P. aeruginosa* Las and Rhl Activities

Compounds 7 and 21 were evaluated for their ability to modulate the Las and Rhl systems using the *P. aeruginosa* PAO1/plasI-LVAgfp and PAO1/prhII-LVAgfp reporters. We used the same exact setup as the static biofilm assay in 96-well microtiter plates for *P. aeruginosa* with the exception that freezer stocks were streaked on LB/agar with 300 μg/mL Carb. Microtiter plates were prepared similar to dose-response analysis such that final well concentrations upon inoculum addition ranged from $10^x$ μM where x=3.5, 3, 2.5, 2, 1.5, 1, 0, −1, or −2. Measurements of FL500/540 and $OD_{600}$ were made at 12 and 24 h, and after 24 h the samples were evaluated for biofilm formation using the CV procedure. Samples were tested in replicates of 3 wells and the average and STE are reported. The $IC_{50}$ values for Las or Rhl inhibition and biofilm inhibition was determined using a sigmoidal curve fit (three parameters) and are reported with a 95% Cl. The results are presented in FIGS. 12, 13, 14 and 15 for PAO1/plasI-LVAgfp and PAO1/prhII-LVAgfp, respectively.

The fluorescence dose curves indicate that both 7 and 21 are able to inhibit both the Las- and Rhl-QS systems. Analogous to the potencies on biofilm inhibition, 21 shows greater potency (i.e., lower $IC_{50}$ values) than 7 against Las and Rhl. Further, both compounds show greater potency at inhibiting biofilm than inhibiting Las- or Rhl-QS with the exception of 21 in PAO1/prhII-LVAgfp, which shows slightly greater inhibitory activity on Rhl than on biofilm formation. However, biofilm $IC_{50}$ values in PAO1/prhII-LVAgfp were higher than those observed in wild-type PAO1, suggesting the rhII reporter strain may grow differently. This trend is consistent with time dependent growth studies that show that the growth of PAO1/prhII-LVAgfp deviates slightly from PAO1 before 12 h (data not shown).

Example 10: Controlled Release from Polymer-Coated Surfaces

Controlled Release of compounds of this invention was exemplified by controlled release of Dimethyl-2-aminobenzimidazole (DMABI, compound 21).

Film Fabrication and Characterization of DMABI Release Profiles

Solvent-cast films of poly(lactide-co-glycolide) (PLG) were used as a model matrix. PLG is a well-known biocompatible, biodegradable, and FDA-approved polymer that has been used for the encapsulation and release of many other small molecule agents [65-70], and the structure of this polymer can be varied to exert a broad range of control over the rates at which small molecules can be released (e.g., over periods ranging from several days to weeks or months) [70]. In the experiments in this example, films fabricated from PLG having a 50:50 ratio of lactide to glycolide repeat units were used.

Figure 16:
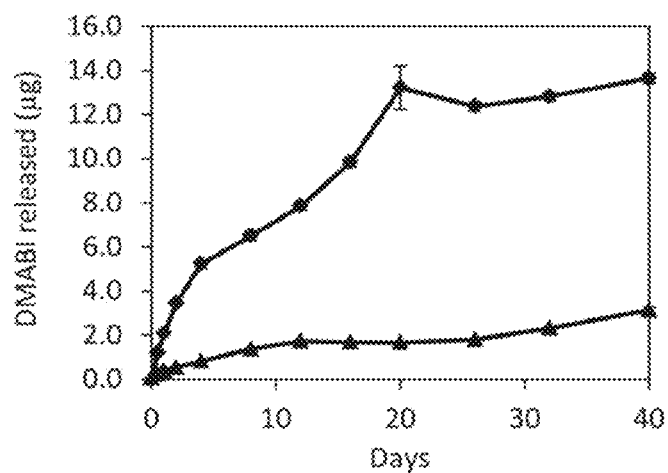
FIG. 16 illustrates a plot of release vs. time for two solvent-cast PLG films loaded with compound 21 [initial loadings of 4.1 µg (triangles) and 16.3 µg (diamonds)] incubated in M9 buffer (pH 7.35) at 37° C. Each data point represents the average of 4 replicate wells; error bars are STE.

A series of experiments were performed to characterize the loading and release of 21 from PLG films that were solvent-cast in the wells of glass-coated 96-well microtiter plates. This microtiter plate platform was designed to facilitate the subsequent evaluation of these materials in bacterial biofilm assays described below. The use of solvent-casting methods provides precise and convenient control over the total amounts of compounds loaded into each film. FIG. 16 shows the release profiles of PLG films containing either 0.1 μmol (16.3 μg; closed diamonds) or 0.025 μmol (4.1 μg; closed triangles) of 21 upon incubation in M9 buffer at 37° C. Inspection of these data reveals that 21 was released from the films over a period of at least 40 days, at which point ~80% of the compound initially loaded into the films was released. Further inspection reveals release to be gradual and to proceed without substantial burst release or the presence of an initial lag phase. Additional experiments demonstrated that compound 21-loaded films solvent-cast in the wells of polypropylene microtiter plates or on the surfaces of planar glass substrates exhibited similar extended release profiles (see FIG. 17). The results in FIG. 17 demonstrate that the release profiles of these films are, in general, similar and that they are not influenced significantly by differences in the underlying substrates or small variations in film fabrication procedures. While many different approaches can be used to vary or tune the rates at which a compound such as compound 21 can be released from these films (or from films fabricated using a range of other degradable or non-degradable polymers), the release profiles shown in Figure X1 were sufficient to provide surface-mediated biofilm inhibition Release of DMABI from Film-Coated Surfaces Inhibits Formation of *P. aeruginosa* Biofilms Films loaded with compound 21 are shown to prevent the formation of biofilms in the opportunistic and clinically relevant pathogen *P. aeruginosa* using a standard static biofilm growth assay. Although the $IC_{50}$ of compound 21 for biofilm inhibition when added exogenously to solution is 4.0 μM, the range of loadings required to inhibit initial or longer-term biofilm growth in these release-based experiments was not known. To determine this range, a series of films with 18 different initial loadings of compound 21 ranging from 0.001 to 0.4 μmol per well in the bottoms of polypropylene microtiter plates (shown schematically in FIG. 18A). These experiments were conducted using two identical sets of films: one set was incubated in the presence of *P. aeruginosa* in a modified M9 media and the other was incubated in M9 buffer in the absence of bacteria (as a negative control, and to facilitate characterization of the amount of compound 21 released at relevant time points, as described above). The amounts of biofilm growth on the bottoms of film-coated wells and at the air/water interface in each well (FIG. 18A), two measures used frequently to characterize biofilm growth in static culture, were quantified after 24 hr by staining the resulting biomass with crystal violet.

Figure 18:
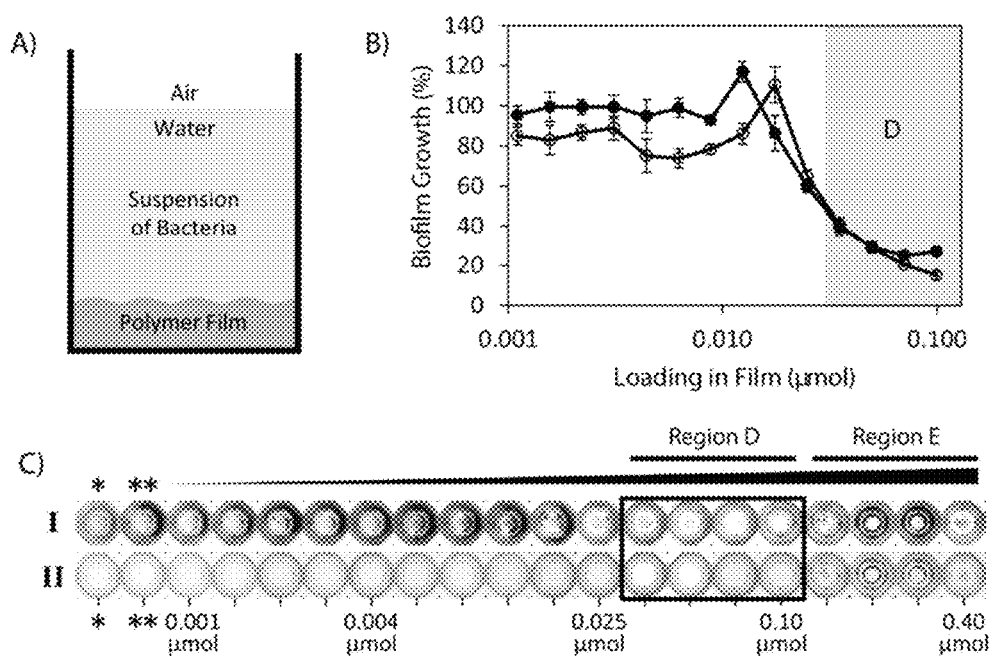
FIG. 18 (A-C) illustrates experiments for characterization of biofilm growth in coated wells. (A) Is a schematic illustration showing the experimental setup for characterization of biofilm growth in PLG-coated wells. Compound 21 was loaded in PLG films solvent-cast on the bottom surface of each well of a microtiter plate and incubated for 24 hours in the presence of a suspension of bacteria. (B) Is a plot of biofilm growth (as a percentage of growth measured in control wells containing PLG films that did not contain compound 21) as a function of initial compound 21 loading. Biofilm growth was characterized and quantified on the bottoms of film-coated wells (closed circles) and at the air/water interface in each well (open circles). (C) Presents digital pictures of film-coated wells fabricated to contain 18 different loadings ranging from 0.001 to 0.40 micromol compound 21 after 24 hours of incubation in the presence of bacteria. Key loading values are labeled; a complete list of all loadings used is included in Table 3. Images shown are of wells after staining of biomass with crystal violet (Row I) and after subsequent de-staining to remove crystal violet (Row II). Results arising from these staining and de-staining procedures were used to quantify amounts of biofilm growth and calculate the results shown in (B). Pictures of wells used as controls containing no polymer coating (bare wells, *) or a polymer coating that did not contain DMABI (PLG only, **) are included for comparison.

FIG. 18B shows a plot of percent biofilm growth (as a function of initial compound 21 loading, and relative to growth in wells containing control films that did not contain 21) on the bottoms of film-coated wells (closed circles) and at the air/water interface in each well (open circles). Films with compound 21 loadings at or below 0.025 μmol per well did not substantially influence the growth of biofilms (i.e., less than 50% inhibition) in either of these locations over this 24-hour incubation period. Films containing higher loadings (0.035 to 0.1 μmol DMABI; Region D) inhibited biofilm formation at both of these interfaces substantially (i.e., greater than 50% inhibition, with a maximum inhibition of up to 85%). Differences in biofilm growth on film-coated well bottoms were also evident by visual inspection of crystal violet-stained wells, as shown in FIG. 18C. The presence and intensity of blue stain in Row I indicates the presence and relative amount of biofilm in each well. Row 2 shows images of the same wells in Row I after the de-staining procedure used to extract crystal violet and obtain the quantitative results shown in FIG. 18B.

Figure 17:
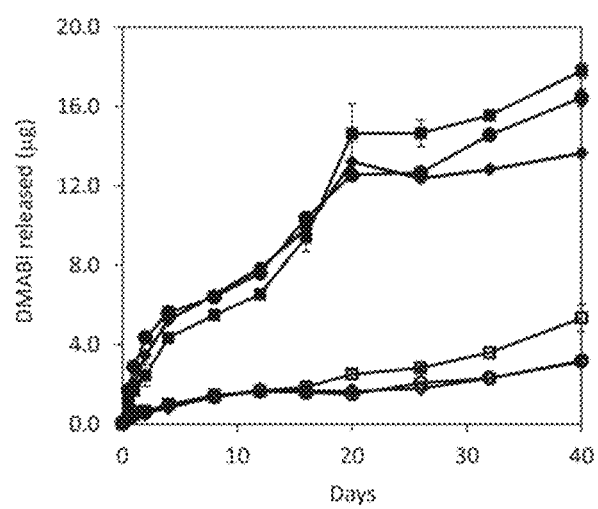
FIG. 17 illustrates a plot of release vs. time for compound 21-loaded PLG films solvent-cast on glass slides (squares) or in the wells of polypropylene (circles) or glass-coated (diamonds) 96-well microtiter plates. All films were fabricated to contain initial compound 21 loadings of either 4.1 µg (open markers) or 16.3 µg (closed markers). Films were incubated in M9 buffer (pH 7.35) at 37° C. and released compound 21 was quantified by monitoring UV absorbance. Each data point represents the average for 2-4 replicate wells; error bars are STE.

The results shown in FIG. 17 demonstrate that the compound is released in a form that is bioactive and at levels that are sufficient to strongly inhibit the formation of *P. aeruginosa* biofilms on surfaces coated with a polymer that otherwise supports robust biofilm growth. This approach can be used to inhibit biofilm growth not only on film-covered surfaces, but also in other environments and locations (e.g., at the air/water interface) that are adjacent to film-coated surfaces, but that are not themselves coated. The similarity of the loading/response profiles for biofilm inhibition at these two different locations (FIG. 18B) indicates that compound 21 and compounds of the invention prevent the formation of biofilm on polymer-coated surfaces through a mechanism that involves the interaction of bacteria with released (i.e., soluble) compound, as opposed to alternate mechanisms that, for example, could depend exclusively upon surface-based interactions between bacteria and the active compound adsorbed to or presented locally at film-coated surfaces.

While the loaded films used in this example, do not result in substantial burst release (FIGS. 16 and 17), formulations containing loadings ranging from 0.035 to 0.1 μmol per well (FIG. 18C, Region D) release amounts of compound 21 that are sufficient to strongly inhibit biofilm formation over the first 24 hr of incubation. Characterization of compound release from otherwise identical films incubated in the absence of bacteria showed that films with loadings at or above 0.05 μmol yielded in-well molar solution concentrations of at least 15.0 μM within the first 6 hr of incubation, a concentration that is over three times the $IC_{50}$ of 4.0 μM reported for this agent. This is an important design consideration from a practical point of view, because a substantial lag phase (or the release of below-threshold concentrations of DMABI during this initial period) would provide bacteria a 'head start' with which to initiate significant levels of biofilm growth (e.g., as shown in FIGS. 18B and 18C for films with loadings below 0.035 μmol). Wells containing the four highest concentrations of compound 21 used here (i.e., loadings ranging from 0.14 to 0.4 μmol per well; Region E of Row I, FIG. 18C) adsorbed significantly more crystal violet than films of intermediate loading (e.g., from 0.035 to 0.1 μmol; Region D, as discussed above).

Inspection of the corresponding wells shown in Row II of FIG. 18C, however, reveals that a significant amount of crystal violet also remained in these samples after the de-staining procedure (in contrast to films at lower loadings, for which de-staining resulted in the removal of almost all visible stain). The presence of this residual stain prevented quantification of biofilm growth on the polymer films and at the air/water interfaces of these wells at these four highest loadings. The reasons for this residual staining are not completely understood, particularly because compound 21 is an inhibitor (and not an activator) of biofilm formation in *P. aeruginosa* at concentrations up to ~3.2 mM, a concentration that is significantly above those generated by the films used in this current investigation.

The occurrence of residual stain in films containing only the four highest mass fractions of compound 21 used here (i.e., loadings ranging from 0.14 to 0.4 μmol) suggests that residual staining could result from physicochemical changes in those films that enable more effective penetration of biofilm (e.g., a potential increase in porosity upon the release of compound 21, such that biofilm is more difficult to de-stain) and/or lead to more effective retention of stain by the polymer matrix itself. In support of this latter possibility, residual, non-specific staining was observed in otherwise identical high-loading films incubated in the absence of bacteria (data not shown). The intensity and uniformity of non-specific staining in these no-bacteria controls varied from experiment to experiment, but these observations reveal that films loaded at these higher mass fractions of compound 21 can also adsorb and retain crystal violet in ways that are independent of biofilm formation (and that are not observed for films with lower loadings of 21). A useful window of compound 21 concentrations exists (particularly, film loadings ranging from 0.035 to 0.1 μmol, FIG. 18B Region D) over which these films can be formulated to strongly inhibit biofilm formation on PLG-coated surfaces.

Inhibition of Biofilm Growth on Adjacent Uncoated Surfaces and Over Extended Periods The ability to inhibit biofilm growth at a variety of other locations (e.g., on the surfaces of other adjacent objects, etc.) using anti-biofilm coatings significantly expands the utility of such materials. An additional series of experiments were performed to characterize the ability of films loaded with compounds of this invention to inhibit the formation of *P. aeruginosa* biofilms on adjacent uncoated surfaces. The ability of these films to inhibit biofilm formation over periods of time extending beyond those used in the initial studies described above was also assessed. To permit periodic characterization of changes in biofilm growth over time, an experiment was designed using loaded PLG films solvent-cast onto the surfaces of planar glass substrates (cut to fit into the wells of a microtiter plate and attached to a plate lid to facilitate suspension in media during culture; see schematic in FIG. 19A). This approach allowed for the iterative insertion and removal of arrays of substrates coated with films containing different loadings of compounds being tested into multiple cultures of bacteria, as well as a practical and straightforward format for characterizing the inhibition of biofilm growth on the bottoms of uncoated plate wells. This approach was used to screen and characterize the ability of compound 21-loaded films (at 18 different loadings, ranging from 0.001 μmol to 0.4 μmol as used in the experiments described above) to inhibit biofilm formation over three discrete and successive 24-hr periods by periodically removing the film-coated substrates and then incubating them further in fresh cultures of bacteria.

Figure 19:
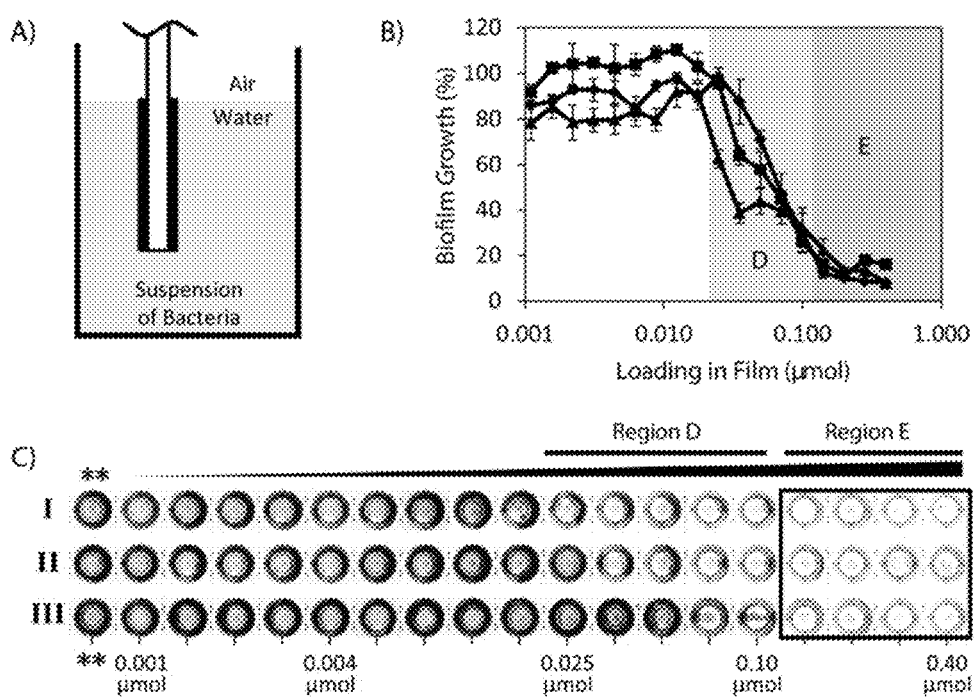
FIG. 19 (A-C) illustrates experiments for characterization of biofilm growth in uncoated wells using suspended film-coated substrates. (A) Is a schematic illustration showing the experimental setup for characterization of biofilm growth in uncoated wells using suspended film-coated substrates. Compound 21-containing PLG films cast on the surfaces of glass chips were suspended in suspensions of bacteria contained in the uncoated wells of a microtiter plate. (B) Plot of biofilm growth (as a percentage of growth measured in control wells containing PLG films that did not contain compound 21) as a function of initial DMABI loading. Films were fabricated to contain 18 different loadings of compound 21 ranging from 0.001 to 0.40 micromol; a complete list of all loadings used is included in Table 3. Biofilm growth was characterized and quantified on the bottoms of film-coated wells after three successive 24-hour challenges in the presence of bacteria. Data correspond to Challenge I (0-24 hours, closed triangles), Challenge II (24-48 hours, closed squares), and Challenge III (48-72 hours, closed diamonds). (C) Present digital pictures of crystal violet-stained biomass present in each well after each 24-hour challenge. Characterization of the amount of crystal violet in each of these wells (determined using a de-staining procedure) was used to quantify amounts of biofilm growth and calculate the results shown in (B). Pictures of control wells that contained chips coated with PLG only (no DMABI, **) are included for comparison.

FIG. 19B shows a plot of percent *P. aeruginosa* biofilm growth as function of DMABI loading for film-coated substrates subjected to three different 24-hr challenges in the presence of bacteria: Challenge I (over 0-24 hr, closed triangles), Challenge II (over 24-48 hr, closed squares), and Challenge III (over 48-72 hr, closed diamonds). Qualitative differences in biofilm growth during each of these challenges are also shown in the pictures of crystal violet-stained wells shown in FIG. 19C. The loading/response profiles for biofilm inhibition on the uncoated well bottoms during Challenge I were generally similar to those described above for data obtained using polymer-coated wells [e.g., an onset of biofilm inhibition at loadings at or above 0.025 μmol (see Regions D of FIGS. 19B and 19C) and up to ~90% inhibition of biofilm growth on uncoated well bottoms at the highest compound 21 loadings (Region E)]. These results also clearly demonstrate that films capable of strongly inhibiting biofilm growth during Challenge I were also able to strongly inhibit biofilm growth upon subsequent introduction to new cultures of bacteria in two additional 24-hr trials (Challenges II and III). For example, films containing loadings of compound 21 ranging from 0.14 to 0.40 μmol (Region E) continued to inhibit biofilm growth on these uncoated surfaces at levels up to ~90% during these two additional challenges (i.e., over a total of three days). Visual inspection of the crystal violet-stained and de-stained suspended release substrates used in these experiments revealed staining and residual staining trends that were analogous to those discussed above and shown in FIG. 2C for films on plate bottoms containing higher mass fractions of compound 21.

The data show that suspended films retain their anti-biofilm activities upon repeated introduction to fresh cultures of bacteria. These results are important because they underscore the ability of these films to promote the gradual and sustained release of useful amounts of these inhibitory compounds over time. Inhibition does not result simply from the release of the inhibitory compound upon the first introduction of the films to media. Closer inspection of the results in Regions D of FIGS. 19B and 19C, corresponding to films with intermediate compound 21 loadings (ranging from 0.025 to 0.10 μmol), reveals the onset and extent of inhibition in this loading range to shift and deteriorate from challenge to challenge. This trend indicates that while these films are able to strongly inhibit biofilm growth over an initial 24-hr period, that films having higher loading are more appropriate for applications that require longer-term inhibition.

Materials and Methods

Materials.

Reagent grade solvents, standard salts and media, and crystal violet were purchased from Sigma Aldrich (Milwaukee, Wis.), Fisher Scientific (Pittsburgh, Pa.), or other commercial sources and used without further purification unless otherwise noted. Poly(D,L-lactide-co-glycolide) (PLG, 50L: 50G, MW=12,000-16,000) and poly(L-lysine) hydrobromide (MW=100,000-140,000) were purchased from Polysciences (Warrington, Pa.). Dimethyl-2-aminobenzimidazole (DMABI, compound 21) was synthesized as described herein using a previously reported procedure [42]. The *P. aeruginosa* strain PAO1 used in biofilm assays was provided by Professor Barbara Iglewski (University of Rochester).

General Considerations.

All assays involving the use of *P. aeruginosa* were performed in a 95:5 mixture of M9+ media:LB media using M9+ medium with the following previously reported composition: 47.7 mM $Na_2HPO_4$, 21.7 mM $KH_2PO_4$, 8.6 mM NaCl, 18.7 mM $NH_4Cl$, 1 mM $MgSO_4$, 0.1 mM $CaCl_2$, 0.4% (w/v) L-Arg, 0.5% (w/v) casamino acids, 0.2% (w/v) anhydrous α-D(+)-glucose, 0.2% (w/v) sodium succinate dibasic hexahydrate, 0.2% (w/v) citric acid monohydrate, and 0.2% (w/v) L-glutamic acid monopotassium salt monohydrate [42]. All experiments that did not involve bacteria were performed in M9 buffer (47.7 mM $Na_2HPO_4$, 21.7 mM $KH_2PO_4$, 8.6 mM NaCl, and 18.7 mM $NH_4Cl$) to prevent contaminating growth and avoid interfering absorbance by other components of M9+ and LB. Phosphate-buffered saline (PBS) used for washing steps in microtiter plate biofilm assays was prepared with the following composition: 10 mM $Na_2HPO_4$, 1.76 mM $KH_2PO_4$, 137 mM NaCl, and 2.7 mM KCl. All solutions and buffers were prepared using 18 MΩ water to minimize trace metal contamination, and were used at pH ~7.35. All media solutions were sterilized by passing them through a 0.22 μm PES (PolyEtherSulfone) membrane filter into autoclaved glassware. All plate-based assays were performed in flat-bottomed 96-well microtiter plates made of either untreated polystyrene (Costar 3370), untreated polypropylene (Costar 3364), or glass-coated polypropylene (SUN-SRi 400 062). For assays performed in non-polystyrene plates, samples were later transferred to flat-bottomed polystyrene or quartz (Hellma) 96-well plates to permit characterization of absorbance using a plate reader. For release studies, microtiter plates were sealed using plate-sealing mats (Costar 3080) to prevent evaporation; plates were covered with standard lids for biofilm studies. Film-coated glass substrates used in these studies were fabricated on glass chips (e.g., 5 mm×7 mm) cut from larger microscope slides (Fisher Scientific) and, in the case of biofilm studies, were attached to the lids of microtiter plates (see text) using epoxy. All film-coated substrates and microtiter plates were sterilized directly before use by UV-C germicidal irradiation for 30 min in a Baker SterilGARD III Advance Biological Safety Cabinet. Absorbance measurements were acquired using a BioTek Synergy 2 plate reader running Gen 5 1.05 software. The wavelength of maximum absorption ($\lambda_{max}$) of DMABI in M9 buffer was determined to be 284 nm, at which the molar extinction coefficient (ε) of DMABI was 8880 A284/M/cm. Data were analyzed using Microsoft Office Excel 2007. Biofilm assay data are shown as a percentage of the positive control (i.e., growth on PLG films that did not contain DMABI) and represent the average and standard error (STE) of three replicate wells. Digital pictures were acquired using a Canon Power Shot S51S digital camera.

Fabrication of DMABI-Containing Films.

PLG films containing DMABI were fabricated on the surfaces of glass chips or the bottoms of the wells of solvent-resistant, 96-well plates using a solvent casting approach. Prior to fabrication, all surfaces were cleaned by rinsing with acetone, exposed to oxygen plasma for 5 min, soaked in a solution of poly(L-lysine) hydrobromide (1 mg/mL in 18 MO water) for 1 hr, and then dried in an oven at 60° C. for 1 hr. DMABI-loaded PLG films containing different specified amounts of DMABI were then fabricated by (1) preparing a series of different stock solutions containing DMABI and PLG (prepared in acetone, with each solution containing a constant concentration of PLG, but varying amounts of DMABI), and (2) depositing equal aliquots of these solutions onto both sides of glass chips or directly into the wells of 96-well plates via pipette. Evaporation of acetone from these films was achieved by either allowing film-coated substrates to stand at room temperature (for glass chips) or by heating them to ~30° C. on a hot plate (for microtiter plates) for 30 min. Film-coated substrates were then placed in a vacuum desiccator at room temperature for at least 12 h to remove any residual solvent prior to use in subsequent experiments. This procedure permitted the fabrication of a series of substrates coated with polymer films containing the same amount of PLG but different known concentrations of DMABI. A list of the volumes and concentrations of stock solutions used, as well as the volumes of the final casting solutions deposited for each of the experiments described below, can be found in Table 3.

TABLE 3

Preparation of PLG/DMABI stock solutions and details of film-casting parameters.

| Type of Experiment | DMABI stock conc. (mg/ml) | Volume stock soln. (μL)[1] | Conc. PLG (mg/ml) | Vol. of PLG stock soln. (mL) | Vol. of soln. cast (μL) | Final DMABI loading (μmol) |
|---|---|---|---|---|---|---|
| Preparation of film-coated substrates for long-term release experiments (e.g. FIGS. X1 and XS2) | 9.5 | 50<br>200 | 24 | 3.5 | 30 | 0.0025<br>0.010 |
| Preparation of film-coated substrates for use in biofilm assays (coated wells or coated glass slides; e.g., FIGS. X2 and X3) | 0.71 | 1815<br>1283<br>907<br>642<br>454<br>321<br>227<br>160<br>113<br>80.2<br>56.7<br>40.1<br>28.4<br>20.1<br>14.2<br>10.0<br>7.1<br>5.0 | 24<br>(well bottoms)<br>36<br>(glass slides) | 600<br>(well bottoms)<br>400<br>(glass slides) | 30<br>(well bottoms[2])<br>2 × 10<br>(glass slides[2]) | 0.40<br>0.28<br>0.20<br>0.14<br>0.10<br>0.071<br>0.050<br>0.035<br>0.025<br>0.018<br>0.013<br>0.0088<br>0.0063<br>0.0044<br>0.0031<br>0.0022<br>0.0016<br>0.0011 |

[1]These aliquots of DMABI solution were dried down and then reconstituted in the volumes of PLG stock solution indicated in Column 5 to give the final casting solutions used for film fabrication.
[2]Films on glass chips were cast from more concentrated solutions than those used to solvent cast films in well bottoms to permit greater control over spreading of the solution, and, thus the dimensions of the coated film. The resulting films, however, contained the same amounts of PLG and DMABI as the respective films cast in well bottoms.

Characterization of DMABI (21) Release Profiles.

The release of DMABI from film-coated substrates was characterized by incubating the films in M9 buffer and measuring changes in solution absorbance at 284 nm (the absorbance maximum of DMABI) as a function of time. For these experiments, 200 µL of buffer was added directly to the wells of a microtiter plate containing either film-coated bottoms or film-coated glass chips. The plates were sealed to prevent evaporation and incubated without shaking at 37° C. At pre-determined times, 100-µL aliquots were removed from 3-4 replicate wells and transferred to the wells of a 96-well quartz plate. Absorbance measurements were made (with path length correction to normalize to a 1 cm path length) in each well and corrected by solvent blank subtraction, and the molar extinction coefficient of DMABI (21) (ε=8880 A284/M/cm) was used to convert these values to molar concentrations of DMABI released per well.

Bacteriological Methods and Characterization of Biofilm Inhibition.

Figure 20:
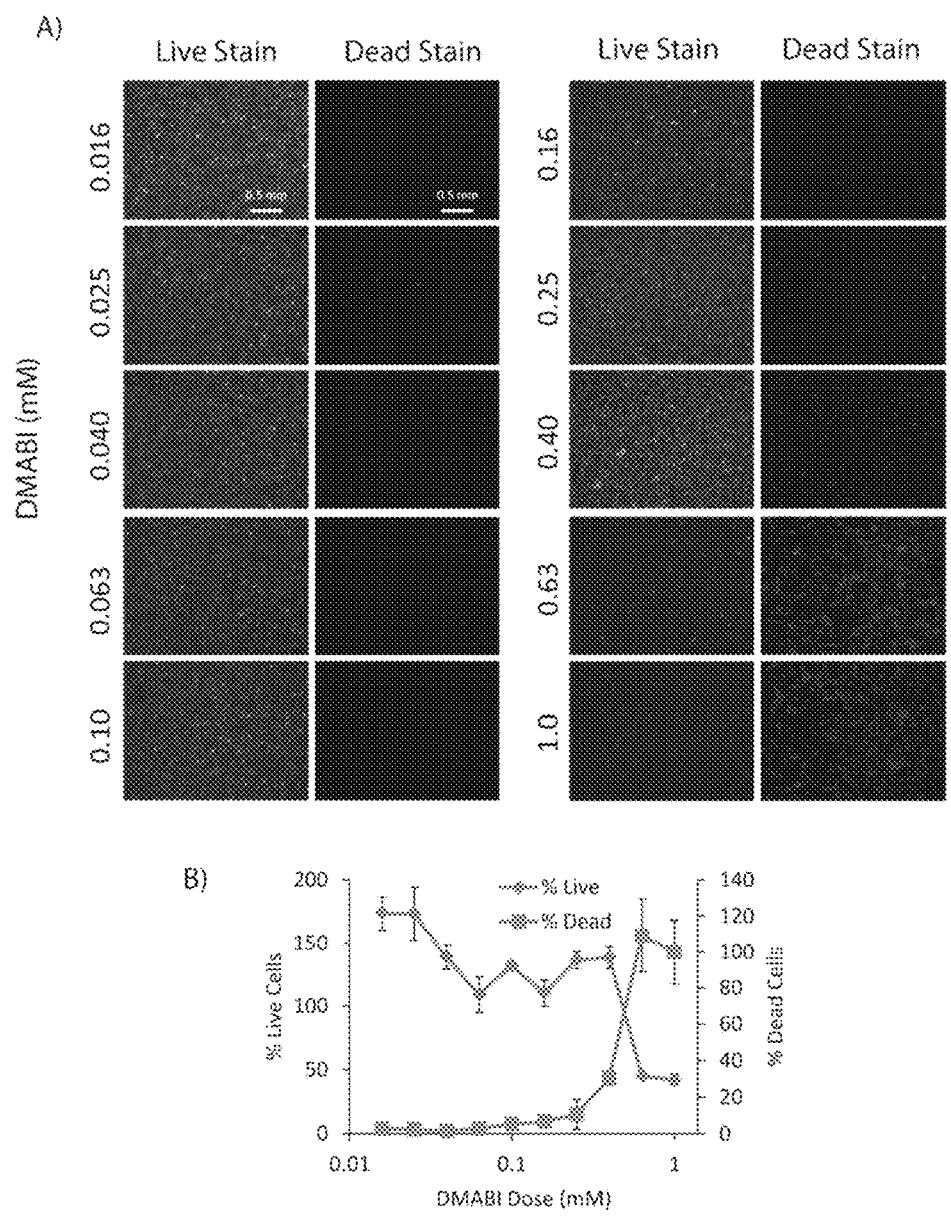
FIG. 20 illustrates results from Example 11. (A) Low magnification fluorescence microscopy images (4×) of COS-7 cells incubated in the presence of different concentrations of compound 21; cells were stained with Calcein AM (green) and ethidium homodimer (red) to identify live and dead cells, respectively, prior to imaging. (B) Plot of mean fluorescence intensity from the images of live and dead cells shown in (A), normalized to untreated (live) and methanol-treated (dead) controls.

The ability of film-coated substrates to inhibit the formation of bacterial biofilms was characterized using (i) films deposited directly on the bottoms of the wells of microtiter plates, and (ii) films deposited on glass chips and suspended from microtiter plate lids (see schematic illustrations in FIGS. 18A and 20A). For suspended-chip experiments, DMABI-loaded films were prepared in a manner identical to that reported above for chip-based release experiments, except that (i) films were cast on the bottom 7 mm of glass chips (5 mm×10 mm in size), and (ii) the uncoated ends of these slides were fixed to the undersides of standard-sized 96-well plate lids. The bioactivity of released DMABI was characterized using *P. aeruginosa* and the crystal violet (CV) static biofilm assay protocol described above. A bacterial inoculating culture was prepared by centrifuging an aliquot of an overnight culture ($OD_{600}$ of ~1.0; 0.5 cm path length) and re-suspending the pellet in 95:5 M9+:LB medium to an $OD_{600}$ of ~0.1-0.2. This culture was added to the wells of microtiter plates in 200-µL aliquots. As a no-bacteria negative control, an identical series of film-coated substrates was incubated in M9 buffer in the absence of *P. aeruginosa*. Plates were covered with a standard microtiter plate lid (for experiments using coated well bottoms) or a lid containing attached glass chips (for suspended-film experiments) and incubated statically at 37° C. for 24 h. After incubation, the bacterial suspension was removed by inverting the plate, and each well was washed twice with 225 µL of PBS to remove loosely bound material not associated with attached biofilm. For experiments in which suspended substrates were used, the substrates were washed twice by soaking in fresh PBS-filled wells for 30 seconds. Biofilms were fixed by placing uncovered plates and lids with suspended chips in a 37° C. oven and thermally dehydrating overnight. Substrates were then treated for 15 min at room temperature with a CV staining solution (200 µL per well; 0.1% (w/v) CV in 95:5 water to ethanol). The staining solution was then removed by inverting the plate and substrates were washed once with 200 µL of PBS and twice with 200 µL of 18 MO water. The plates and suspended chips were dried at 37° C. and then imaged on a white light trans-illuminator using a digital camera. The amount of CV retained by the biofilm was quantified by re-solubilizing (or "de-staining") the CV in 30% acetic acid and measuring the absorbance at 590 nm using a two-step process. To characterize the amount of biofilm at the well bottoms, 100 µL of 30% acetic acid was added to each well, gently pipetted to re-solubilize the CV, and then characterized by UV/visible spectrophotometry. After removal of the first aliquot of acetic acid, wells were then refilled with 225 µL of 30% acetic acid to characterize the amount of biofilm originally present at the air/water interface, as previously described above, see also [64]. Experiments to characterize the ability of film-coated substrates to inhibit biofilm over longer periods were performed in the following manner. After an initial 24-hr challenge in the presence of bacteria, suspended chips were washed twice as described above. Suspended chips were then subjected to two additional and successive 24-hr challenges by transferring them to the wells of new plates containing 200 µL of a fresh 1-in-10 inoculating culture of *P. aeruginosa*. These additional challenges, and procedures used to characterize extents of biofilm formation resulting from them, were performed using the methods described above.

Example 11: Characterization of the Cytotoxicity in Mammalian Cells

Experiments to characterize the toxicity of exemplary compound 21 in a model mammalian cell line were conducted by incubating COS-7 African Green Monkey kidney cells (American Type Culture Collection, Manassas, Va.), a fibroblast-like mammalian cell line, in the presence of varying amounts of compound 21 and characterizing resulting levels of cell death using a standard fluorescence-based live/dead assay. Cells were seeded in 96-well plates by adding 200 µL of a suspension containing 50,000 cells/mL in cell culture media (Gibco® DMEM supplemented with 10% (v/v) fetal bovine serum, 100 units/mL penicillin, and 100 µg/mL streptomycin) in individual wells of a black-walled, clear-bottomed 96-well cell culture plate (Costar 3603). Cells were incubated for 24 h at 37° C. to allow for cell attachment and growth, after which 150 µL of the media in each well was removed and replaced with media containing varying amounts of compound 21. Media with compound 21 was prepared beforehand by first dissolving 0.29 mg compound 21 in 1.349 mL media, and then making a 1:1.71 dilution series to give solutions that, after adding to cells, ranged in concentration from 0.016 to 1.0 mM compound 21 (see Figure XS1). Cells were incubated in the presence of compound 21 at 37° C. for another 24 hrs, after which 30 µL of a concentrated staining solution (10 µM Calcein AM and 10 µM ethidium homodimer) was added to each well and incubated at 37° C. for 30 min. Fluorescence microscopy images of the wells were acquired using an Olympus IX70 microscope and Metavue version 7.1.2.0 software package (Molecular Devices, Toronto, Canada). Images were analyzed using Image J 1.43u (National Institutes of Health; Washington, D.C.). Live and dead cell results were also analyzed by averaging the mean fluorescence from a minimum of six images taken from three replicate samples and normalized to untreated (live control) and methanol-treated (dead control) wells (see FIG. 20).

These results reveal that compound 21 is not substantially cytotoxic to COS-7 cells, under the conditions used in this assay, at concentrations below 0.25 mM. This concentration is well above the $IC_{50}$ of compound 21 (4 µM), providing a large window of concentrations over which compound 21 may be used as an active inhibitor of biofilm formation without significant cytotoxic effects on mammalian cells

REFERENCES (1) Hall-Stoodley, L.; Costerton, J. W.; Stoodley, P. Nat. Rev. Microbiol. 2004, 2, 95-108.

(2) Davies, D. Nat. Rev. Drug Disc. 2003, 2, 114-122.

(3) Flemming, H. C.; Wingender, J. Nat. Rev. Microbiol. 2010, 8, 623-633.
(4) Costerton, J. W.; Stewart, P. S.; Greenberg, E. P. Science 1999, 284, 1318-1322.
(5) Smith, K. M.; Bu, Y. G.; Suga, H. Chem. Biol. 2003, 10, 81-89.
(6) Musk, D. J.; Hergenrother, P. J. Curr. Med. Chem. 2006, 13, 2163-2177.
(7) Sintim, H. O.; Smith, J. A.; Wang, J.; Nakayama, S.; Yan, L. Future Med. Chem. 2010, 2, 1005-1035.
(8) Richards, J. J.; Melander, C. Anti-Infective Agents Med. Chem. 2009, 8, 295-314.
(9) Hentzer, M.; Riedel, K.; Rasmussen, T. B.; Heydorn, A.; Andersen, J. B.; Parsek, M. R.; Rice, S. A.; Eberl, L.; Molin, S.; Hoiby, N.; Kjelleberg, S.; Givskov, M. Microbiology 2002, 148, 87-102.
(10) Musk, D. J.; Banko, D. A.; Hergenrother, P. J. Chem. Biol. 2005, 12, 789-796.
(11) Geske, G. D.; Wezeman, R. J.; Siegel, A. P.; Blackwell, H. E. J. Am. Chem. Soc. 2005, 127, 12762-12763.
(12) Junker, L. M.; Clardy, J. Antimicrob. Agents Chemother. 2007, 51, 3582-3590.
(13) Kim, C.; Kim, J.; Park, H. Y.; Park, H. J.; Lee, J. H.; Kim, C. K.; Yoon, J. Appl. Microbiol. Biotechnol. 2008, 80, 37-47.
(14) Sambanthamoorthy, K.; Gokhale, A. A.; Lao, W. W.; Parashar, V.; Neiditch, M. B.; Semmelhack, M. F.; Lee, I.; Waters, C. M. Antimicrob. Agents Chemother. 2011, 55, 4369-4378.
(15) Davies, D. G.; Parsek, M. R.; Pearson, J. P.; Iglewski, B. H.; Costerton, J. W.; Greenberg, E. P. Science 1998, 280, 295-298.
(16) Tang, H. B.; DiMango, E.; Bryan, R.; Gambello, M.; Iglewski, B. H.; Goldberg, J. B.; Prince, A. Infect. Immun. 1996, 64, 37-43.
(17) Rumbaugh, K. P.; Griswold, J. A.; Hamood, A. N. Microbes Infect. 2000, 2, 1721-1731.
(18) Geske, G. D.; O'Neill, J. C.; Blackwell, H. E. Chem. Soc. Rev. 2008, 37, 1432-1447.
(19) Glansdorp, F. G.; Thomas, G. L.; Lee, J. J. K.; Dutton, J. M.; Salmond, G. P. C.; Welch, M.; Spring, D. R. Org. Biomol. Chem. 2004, 2, 3329-3336.
(20) Breitbach, A. S.; Broderick, A. H.; Jewell, C. M.; Gunasekaran, S.; Lin, Q.; Lynn, D. M.; Blackwell, H. E. Chem. Commun. 2011, 47, 370-372.
(21) Palmer, A. G.; Streng, E.; Blackwell, H. E. ACS Chem. Biol. 2011, in press.
(22) Rogers, S. A.; Huigens, R. W., 3rd; Melander, C. J. Am. Chem. Soc. 2009, 131, 9868-9869.
(23) Lee, J.-H.; Cho, M. H.; Lee, J. Environ. Microbiol. 2011, 13, 62-73.
(24) Fulghesu, L.; Giallorenzo, C.; Savoia, D. J. Chemotherapy 2007, 19, 388-391.
(25) Frei, R.; Blackwell, H. E. Chem.-Eur. J. 2010, 16, 2692-2695.
(26) Li, W. J.; Nelson, D. P.; Jensen, M. S.; Hoerrner, R. S.; Javadi, G. J.; Cai, D.; Larsen, R. D. Org. Lett. 2003, 5, 4835-4837.
(27) Ermolat'ev, D. S.; Van der Eycken, E. V. J. Org. Chem. 2008, 73, 6691-6697.
(28) Yang, J. S.; Liau, K. L.; Li, C. Y.; Chen, M. Y. J. Am. Chem. Soc. 2007, 129, 13183-13192.
(29) Sambanthamoorthy, K.; Gokhale, A. A.; Lao, W. W.; Parashar, V.; Neiditch, M. B.; Semmelhack, M. F.; Lee, I.; Waters, C. M. Antimicrob. Agents Chemother. 2011, 55, 4369-4378.
(30) WO 2010144686 (A1), 2010.
(31) Valdez, J.; Cedillo, R.; Hernandez-Campos, A.; Yepez, L.; Hernandez-Luis, F.; Navarrete-Vazquez, G.; Tapia, A.; Cortes, R.; Hernandez, M.; Castillo, R. Bioorg. Med. Chem. Lett. 2002, 12, 2221-2224.
(32) Grossman, T. H.; Mani, N.; Gross, C. H.; Parsons, J. D.; Hanzelka, B.; Muh, U.; Mullin, S.; Liao, Y. S.; Grillot, A. L.; Stamos, D.; Charifson, P. S. Antimicrob. Agents Chemother. 2006, 50, 1228-1237.
(33) Coldham, N. G.; Webber, M.; Woodward, M. J.; Piddock, L. J. V. J. Antimicrob. Chemother. 2010, 65, 1655-1663.
(34) Liu, C.; Worthington, R. J.; Melander, C.; Wu, H. Antimicrob. Agents Chemother. 2011, 55, 2679-2687.
(35) Flatt, A. K.; Dirk, S. M.; Henderson, J. C.; Shen, D. E.; Su, J.; Reed, M. A.; Tour, J. M. Tetrahedron 2003, 59, 8555-8570
(36) Goodacre, S. C.; Street, L. J.; Hallett, D. J.; Crawforth, J. M.; Kelly, S.; Owens, A. P.; Blackaby, W. P.; Lewis, R. T.; Stanley, J.; Smith, A. J.; Ferris, P.; Sohal, B.; Cook, S. M.; Pike, A.; Brown, N.; Wafford, K. A.; Marshall, G.; Castro, J. L.; Atack, J. R. J. Med. Chem. 2006, 49, 35-38.
(37) McNulty, J.; Das, P. Eur. J. Org. Chem. 2009, 4031-4035.
(38) Littke, A. F.; Fu, G. C. J. Am. Chem. Soc. 2001, 123, 6989-7000.
(39) Huigens, R. W.; Reyes, S.; Reed, C. S.; Bunders, C.; Rogers, S. A.; Steinhauer, A. T.; Melander, C. Bioorg. Med. Chem. 2010, 18, 663-674.
(40) De Kievit, T. R.; Gillis, R.; Marx, S.; Brown, C.; Iglewski, B. H. Appl. Environ. Microbiol. 2001, 67, 1865-1873.
(41) Lambertsen, L.; Sternberg, C.; Molin, S. Environ. Microbiol. 2004, 6, 726-732.
(42) Koch, B.; Jensen, L. E.; Nybroe, O. J. Microbiol. Methods 2001, 45, 187-195.
(43) Simon, R.; Priefer, U.; Puhler, A. Nat. Biotechnol. 1983, 1, 784-791.
(44) Shrout, J. D.; Chopp, D. L.; Just, C. L.; Hentzer, M.; Givskov, M.; Parsek, M. R. Mol. Microbiol. 2006, 62, 1264-1277.
(45) Merritt, J. H.; Kadouri, D. E.; O'Toole, G. A. In Curr. Protoc. Microbiol.; 2008/09/05 ed. 2005; Vol. Chapter 1, p Unit 1B1.
(46) Caiazza, N. C.; O'Toole, G. A. J. Bacteriol. 2004, 186, 4476-4485.
(47) Anderson, G. G.; Moreau-Marquis, S.; Stanton, B. A.; O'Toole, G. A. Infect. Immun. 2008, 76, 1423-1433.
(48) Banin, E.; Vasil, M. L.; Greenberg, E. P. P. Natl. Acad. Sci. USA 2005, 102, 11076-11081.
(49) Glick, R.; Gilmour, C.; Tremblay, J.; Satanower, S.; Avidan, O.; Deziel, E.; Greenberg, E. P.; Poole, K.; Banin, E. J. Bacteriol. 2010, 192, 2973-2980.
(50) Kim, E. J.; Wang, W.; Deckwer, W. D.; Zeng, A. P. Microbiology 2005, 151, 1127-1138.
(51) O'May, C. Y.; Sanderson, K.; Roddam, L. F.; Kirov, S. M.; Reid, D. W. J. Med. Microbiol. 2009, 58, 765-773.
(52) Patriquin, G. M.; Banin, E.; Gilmour, C.; Tuchman, R.; Greenberg, E. P.; Poole, K. J. Bacteriol. 2008, 190, 662-671.
(53) Yang, L.; Barken, K. B.; Skindersoe, M. E.; Christensen, A. B.; Givskov, M.; Tolker-Nielsen, T. Microbiology 2007, 153, 1318-1328.
(54) Schwyn, B.; Neilands, J. B. Anal. Biochem. 1987, 160, 47-56.
(55) Vogel, H. J.; Bonner, D. M. J. Biol. Chem. 1956, 218, 97-106.

(56) Christensen, G. D.; Simpson, W. A.; Younger, J. J.; Baddour, L. M.; Barrett, F. F.; Melton, D. M.; Beachey, E. H. J. Clin. Microbiol. 1985, 22, 996-1006.

(57) O'Toole, G. A.; Pratt, L. A.; Watnick, P. I.; Newman, D. K.; Weaver, V. B.; Kolter, R. Methods Enzymol. 1999, 310, 91-109.

(58) Meechan, P. J.; Wilson, C. Appl. Biosafety 2006, 11, 222-227.

(59) Hentzer, M.; Riedel, K.; Rasmussen, T. B.; Heydorn, A.; Andersen, J. B.; Parsek, M. R.; Rice, S. A.; Eberl, L.; Molin, S.; Hoiby, N.; Kjelleberg, S.; Givskov, M. Microbiology 2002, 148, 87-102.

(60) Andersen, J. B.; Sternberg, C.; Poulsen, L. K.; Bjorn, S. P.; Givskov, M.; Molin, S. Appl. Environ. Microbiol. 1998, 64, 2240-2246.

(61) Cormack, B. P.; Valdivia, R. H.; Falkow, S. Gene 1996, 173, 33-38.

(62) MacDonald, J. C.; Bishop, G. G. Biochim. Biophys. Acta 1984, 800, 11-20.

(63) Sambrook, J.; Russell, D. W. Molecular Cloning: A Laboratory Manual; 3rd ed.; Cold Spring Harbour Laboratory Press: New York, 2001.

(64) R. Frei, A. S. Breitbach, H. E. Blackwell, 2-Aminobenzimidazole Derivatives Strongly Inhibit and Disperse Pseudomonas aeruginosa Biofilms, Angew. Chem., Int. Ed., 51 (2012) 5226-5229.

(65) P. Wu, D. W. Grainger, Drug/device combinations for local drug therapies and infection prophylaxis, Biomaterials, 27 (2006) 2450-2467.

(66) J. M. Anderson, M. S. Shive, Biodegradation and biocompatibility of PLA and PLGA microspheres, Adv. Drug Delivery Rev., 28 (1997) 5-24.

(67) R. A. Jain, The manufacturing techniques of various drug loaded biodegradable poly(lactide-co-glycolide) (PLGA) devices, Biomaterials, 21 (2000) 2475-2490.

(68) G. Chen, T. Ushida, T. Tateishi, Scaffold Design for Tissue Engineering, Macromol Biosci, 2 (2002) 67-77.

(69) J. Panyam, V. Labhasetwar, Biodegradable nanoparticles for drug and gene delivery to cells and tissue, Adv. Drug Delivery Rev., 55 (2003) 329-347.

(70) S. Fredenberg, M. Wahlgren, M. Reslow, A. Axelsson, The mechanisms of drug release in poly(lactic-co-glycolic acid)-based drug delivery systems-A review, Int J Pharm, 415 (2011) 34-52.

We claim:

1. A method for inhibiting the formation of a biofilm or dispersing an already-formed biofilm of *Pseudomonas aeruginosa* which comprises the step of contacting the *Pseudomonas aeruginosa* or the biofilm thereof with an effective amount of one or more compounds selected from: 5-iodo-2-aminobenzimidazole; 5-bromo-2-aminobenzimidazole, 5-chloro-2-aminobenzimidazole, 5-fluoro-2-aminobenzimidazole, 5-nitro-2-aminobenzimidazole, 5-methyl-2-aminobenzimidazole, 4-methyl-2-aminobenzimidazole, 5,6-dimethyl-2-aminobenzimidazole, 5-methoxy-2-aminobenzimidazole, and 2-amino-1H-naphtho[2,3-d]imidazole.

2. The method of claim 1, wherein an already-formed biofilm of *Pseudomonas aeruginosa* is dispersed.

3. The method of claim 2, wherein the one or more compound is 5,6-dimethyl-2-aminobenzimidazole.

4. The method of claim 1, wherein the one or more compound is 5,6-dimethyl-2-aminobenzimidazole.

5. The method of claim 1, wherein the one or more compounds are selected from: 5-iodo-2-aminobenzimidazole; 5-bromo-2-aminobenzimidazole, 5-chloro-2-aminobenzimidazole, 5-fluoro-2-aminobenzimidazole, and 5-nitro-2-aminobenzimidazole.

6. The method of claim 5, wherein an already-formed biofilm of *Pseudomonas aeruginosa* is dispersed.

7. The method of claim 1, wherein the one or more compounds are selected from: 5-methyl-2-aminobenzimidazole, 4-methyl-2-aminobenzimidazole, 5,6-dimethyl-2-aminobenzimidazole, and 5-methoxy-2-aminobenzimidazole.

8. The method of claim 7, wherein an already-formed biofilm of *Pseudomonas aeruginosa* is dispersed.

9. The method of claim 1, wherein contacting includes release of the one or more compounds from a film, multilayer film, coating, hydrogel, microsphere or nanosphere.

* * * * *